(12) United States Patent
Miranda et al.

(10) Patent No.: US 10,213,445 B2
(45) Date of Patent: *Feb. 26, 2019

(54) COMPOSITIONS AND METHODS OF DIAZENIUMDIOLATE-BASED PRODRUGS FOR TREATING CANCER

(71) Applicants: ARIZONA BOARD OF REGENTS ON BEHALF OF THE UNIVERSITY OF ARIZONA, Tucson, AZ (US); The United States of America as Represented by the Secretary of the Department of Health and Human Services, Bethesda, MD (US)

(72) Inventors: Katrina M. Miranda, Tucson, AZ (US); David A. Wink, Bethesda, MD (US); Debashree Basudhar, Tucson, AZ (US)

(73) Assignees: Arizona Board of Regents on Behalf of the University of Arizona, a body corporate, Tucson, AZ (US); The United States of America as Represented by the Secretary of the Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/523,670

(22) PCT Filed: Nov. 6, 2015

(86) PCT No.: PCT/US2015/059428
§ 371 (c)(1),
(2) Date: May 1, 2017

(87) PCT Pub. No.: WO2016/073835
PCT Pub. Date: May 12, 2016

(65) Prior Publication Data
US 2017/0333456 A1    Nov. 23, 2017

Related U.S. Application Data

(60) Provisional application No. 62/075,936, filed on Nov. 6, 2014.

(51) Int. Cl.
| | | |
|---|---|---|
| *A61K 31/655* | (2006.01) | |
| *A61K 47/54* | (2017.01) | |
| *A61K 47/55* | (2017.01) | |
| *A61K 31/138* | (2006.01) | |

(52) U.S. Cl.
CPC .......... *A61K 31/655* (2013.01); *A61K 31/138* (2013.01); *A61K 47/54* (2017.08); *A61K 47/542* (2017.08); *A61K 47/55* (2017.08)

(58) Field of Classification Search
CPC .................................................. A61K 31/655
USPC ....................................................... 514/150
See application file for complete search history.

(56) References Cited

U.S. PATENT DOCUMENTS

| | | | | |
|---|---|---|---|---|
| 7,799,782 B2 * | 9/2010 | Munson | ............... | C07D 231/56 514/234.5 |
| 8,633,177 B2 * | 1/2014 | Miranda | ............... | C07D 231/16 514/150 |

FOREIGN PATENT DOCUMENTS

WO    WO2011/116336    *    9/2011

OTHER PUBLICATIONS

Basudhar et al., CAS: 159: 588357, 2013. (Year: 2013).*
Basudhar et al. CAS: 159: 588357, 2013.*

* cited by examiner

*Primary Examiner* — Rei Tsang Shiao
(74) *Attorney, Agent, or Firm* — Don D. Cha; Hamilton DeSanctis & Cha, LLP

(57) ABSTRACT

The present disclosure provides methods utilizing the diazeniumdiolate-based prodrugs for the treatment of cancer via various mechanisms and procedures. The disclosure also provides kits comprising the diazeniumdiolate-based prodrugs.

14 Claims, 18 Drawing Sheets

COMPOSITIONS AND METHODS OF DIAZENIUMDIOLATE-BASED PRODRUGS FOR TREATING CANCER

CROSS REFERENCE TO RELATED APPLICATIONS

This application is U.S. National Stage Application under 35 U.S.C. § 371 of PCT Patent Application No. PCT/US2015/059428, filed Nov. 6, 2015, which claims the benefit under 35 U.S.C. § 119(e) of U.S. Provisional Patent Application No. 62/075,936, filed Nov. 6, 2014, all of which are incorporated by reference in their entirety.

GOVERNMENT RIGHTS

This invention was made with government support under Grant No. R01-GM076247, awarded by NIH. The government has certain rights in the invention.

TECHNICAL FIELD

The invention relates to methods using compositions of diazeniumdiolate-based prodrugs for treating cancer. The invention also includes kits comprising compositions of diazeniumdiolate-based prodrugs.

BACKGROUND AND SUMMARY OF THE INVENTION

Despite the fact that there have been significant developments in anti-cancer technology, such as radiotherapy, chemotherapy and hormone therapy, cancer still remains the second leading cause of death following heart disease in the United States. Most often, cancer is treated with chemotherapy utilizing highly potent drugs. In many cases, these chemotherapeutic agents show a dose responsive effect, and cell killing is proportional to drug dose. A highly aggressive style of dosing is thus necessary to eradicate neoplasms. However, high-dose chemotherapy is hindered by poor selectivity for cancer cells and severe toxicity to normal cells. This lack of tumor-specific treatment is one of the many hurdles that needs to be overcome by current chemotherapy.

One solution to current chemotherapy limitations would be to deliver an effective concentration of anti-cancer agents to utilize various pathways resulting in cancer cell death. For example, induction of DNA damage, increasing oxidant levels, increasing apoptosis, decreasing angiogenesis, inhibiting metastasis, and/or decreasing glycolysis using anti-cancer agents may be beneficial for patients.

Another approach to overcoming current chemotherapeutic limitations would be to deliver a combination of a tumor-targeted drug with one or more chemotherapeutic agents where the toxicity profile of the tumor-targeted drug and the chemotherapeutic agent are different. A further modification of this approach is to use the tumor-targeted drug and the chemotherapeutic agent in the combination treatment in amounts of each lower than typically used when the tumor-targeted drug or the chemotherapeutic agent is used alone for treatment.

Recent attention has been given to nitric oxide (NO) derivatives (NO-NSAIDs) for the treatment of cancer. The role of NO in cancer is complicated in that NO production can be mutagenic yet can affect apoptosis, proliferation, migration, adhesion, angiogenesis and vascular permeability. Often, low levels of NO may be pro-tumorigenic, while production of higher, sustained levels of NO can have cytostatic and cytotoxic effects on cancer cells. However, expression of the inducible isoform of NO synthase (iNOS) has been reported in malignancies of the breast, prostate, lung, brain and colon. Detection of increased iNOS levels also predicts poor survival in estrogen receptor α-negative (ER(−)) breast cancer patients. Thus, inhibition of iNOS within cancer cells may be therapeutic while delivery of exogenous NO may initiate tumor regression in simulation of the immune system. NO donors may lead to chemo- and radiosensitization and to overcome drug resistance by tumor cells.

Therefore, there exists a need for new methods that utilize various pathways resulting in cancer cell death. Accordingly, the present disclosure provides methods of using diazeniumdiolate-based prodrugs for treating cancer, which exhibit desirable properties and provide related advantages for modifying cancer cells.

The present disclosure provides methods utilizing the diazeniumdiolate-based prodrugs for the treatment of cancer via various mechanisms and procedures. The disclosure also provides kits comprising the diazeniumdiolate-based prodrugs.

Any of the embodiments described in the following clause list are considered to be part of the invention and are non-limiting:

1. A method of inducing DNA damage of a cell, said method comprising the step of administering a compound of the formula (I) or a pharmaceutically acceptable salt thereof:

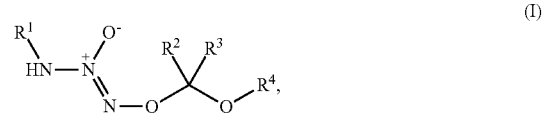

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is $-C(=O)R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the cell, wherein contacting the cell with the compound induces the DNA damage of the cell.

2. The method of clause 1, wherein the DNA damage comprises deamination of one or more base pairs in the cell.

3. The method of clause 1 or clause 2, wherein the DNA damage comprises cleavage of the DNA.

4. A method of binding to a thiol of a cellular protein, said method comprising the step of administering a compound of the formula (I) or a pharmaceutically acceptable salt thereof:

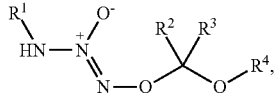

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to a cell comprising the cellular protein, wherein the compound binds to one or more thiols of the cellular protein.

5. The method of clause 4, wherein the binding is formed via HNO donation.

6. A method of increasing an oxidant level in a cell, said method comprising the step of administering a compound of the formula (I) or a pharmaceutically acceptable salt thereof:

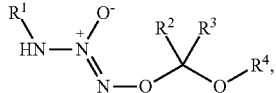

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the cell, wherein contacting the cell with the compound increases the oxidant level of the cell.

7. A method of increasing apoptosis of a population of cells, said method comprising the step of administering a compound of the formula (I) or a pharmaceutically acceptable salt thereof:

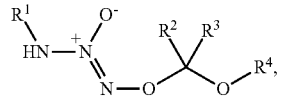

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the population of cells, wherein contacting the compound with the population of cells increases the occurrence of apoptosis in the population of cells.

8. The method of clause 7, wherein the apoptosis occurs via a caspase signaling cascade.

9. The method of clause 8, wherein the caspase is caspase-3.

10. A method of decreasing angiogenesis in a population of cells, said method comprising the step of administering a compound of the formula (I) or a pharmaceutically acceptable salt thereof:

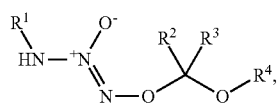

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the population of cells, wherein contacting the compound with the population of cells decreases the occurrence of angiogenesis in the population of cells.

11. A method of inhibiting metastasis of a cell, said method comprising the step of administering a compound of the formula (I) or a pharmaceutically acceptable salt thereof:

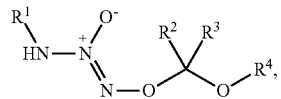

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the cell, wherein contacting the cell with the compound inhibits the metastasis of the cell.

12. A method of modifying a phenotype of a cell, said method comprising the step of contacting the cell with a compound of the formula (I) or a pharmaceutically acceptable salt thereof:

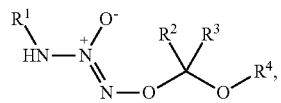

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the cell, wherein contacting the cell with the compound modifies the phenotype of the cell.

13. The method of any one of clauses 1 to 12, wherein the cell is a cancer cell.

14. The method of clause 13, wherein the cancer cell is a proliferating cancer cell.

15. The method of clause 13 or clause 14, wherein the cancer cell is located in an oxygenated region of a tumor.

16. The method of clause 13 or clause 14, wherein the cancer cell is located in a non-oxygenated region of a tumor.

17. A method of decreasing glycolysis in a mammal, said method comprising the step of administering a compound of the formula (I) or a pharmaceutically acceptable salt thereof:

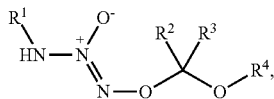

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, to the mammal, wherein the compound of the formula (I) or pharmaceutically acceptable salt thereof decreases glycolysis in the mammal.

18. The method of clause 17, wherein the decrease of glycolysis comprises an inhibition of GAPDH activity.

19 The method of clause 18, wherein the inhibition of GAPDH activity is associated with a cancer cell.

20. A method of treating cancer, said method comprising the step of administering a compound and a therapeutic agent to a mammal, wherein the compound is a compound of the formula (I) or a pharmaceutically acceptable salt thereof:

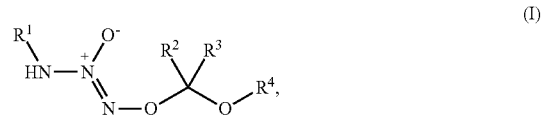

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity, wherein the compound of the formula (I) or pharmaceutically acceptable salt and the therapeutic agent are effective in treating cancer in the mammal.

21. The method of clause 20, wherein the cancer is selected from the group consisting of breast cancer, lung cancer, prostate cancer, bone cancer, skin cancer, melanoma, pancreatic cancer, liver cancer, colon cancer, colorectal cancer, stomach cancer, esophageal cancer, nasopharyngeal cancer, thyroid cancer, ovarian cancer, bladder cancer, uterine cancer, multiple myeloma, leukemia, lymphoma, melanoma, sarcoma, nasopharyngeal cancer, kidney cancer, testicular cancer, brain cancer, Hodgkin's disease and non-Hodgkin's lymphoma.

22. The method of clause 20, wherein the therapeutic agent is tamoxifen.

23. The method of clause 21, wherein the cancer is breast cancer and wherein the breast cancer is an estrogen receptor negative (ER(−)) breast cancer.

24. The method of any one of clauses 20 to 23, wherein the cancer is located in an oxygenated region of a tumor.

25. The method of any one of clauses 20 to 23, wherein the cancer is located in a non-oxygenated region of a tumor.

26. The method of any one of clauses 1 to 25, wherein the compound of the formula (I) or pharmaceutically acceptable salt thereof releases HNO at physiological pH.

27. The method of any one of clauses 1 to 26, wherein $R^1$ is optionally substituted $C_{1-12}$ alkyl, optionally substituted $C_{3-12}$ alkenyl, or optionally substituted $C_{3-8}$ cycloalkyl.

28. The method of any one of clauses 1 to 27, wherein $R^2$ and $R^3$ are the same or different and each is hydrogen, $C_{1-12}$ alkyl, aryl, or heteroaryl, each of which, other than hydrogen, is optionally substituted.

29. The method of any one of clauses 1 to 28, wherein $R^2$ and $R^3$ are hydrogen.

30. The method of any one of clauses 1 to 29, wherein $R^1$ is optionally substituted $C_{1-12}$ alkyl.

31. The method of any one of clauses 1 to 29, wherein $R^1$ is optionally substituted $C_{1-4}$ alkyl.

32. The method of any one of clauses 1 to 29, wherein $R^1$ is isopropyl.

33. The method of any one of clauses 1 to 32, wherein $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxycarbonyl, $C_{1-12}$ alkoxy-carbonyloxy, amido, amino, $C_{1-12}$ alkylamino, and di-$C_{1-12}$ alkyl-amino 34. The method of any one of clauses 1 to 33, wherein $R^5$ is an optionally substituted $C_{1-12}$ alkyl 35. The method of any one of clauses 1 to 34, wherein the compound of formula (I) is

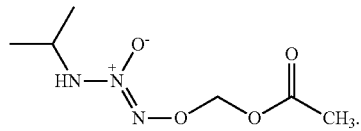

36. The method of any one of clauses 1 to 34, wherein $R^4$ is an NSAID moiety retaining its NSAID activity 37. The method of clause 36, wherein said NSAID moiety is a moiety of an NSAID selected from the group consisting of aspirin, propionic acid derivatives, acetic acid derivatives, sulphonanilides, licofelone, enolic acid derivatives, fenamic acid derivatives, and selective COX-2 inhibitors 38. The method of clause 36, wherein the NSAID is selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, licofenac, and mflumic acid 39. The method of any one of clauses 1 to 38, wherein the compound is selected from the group consisting of:

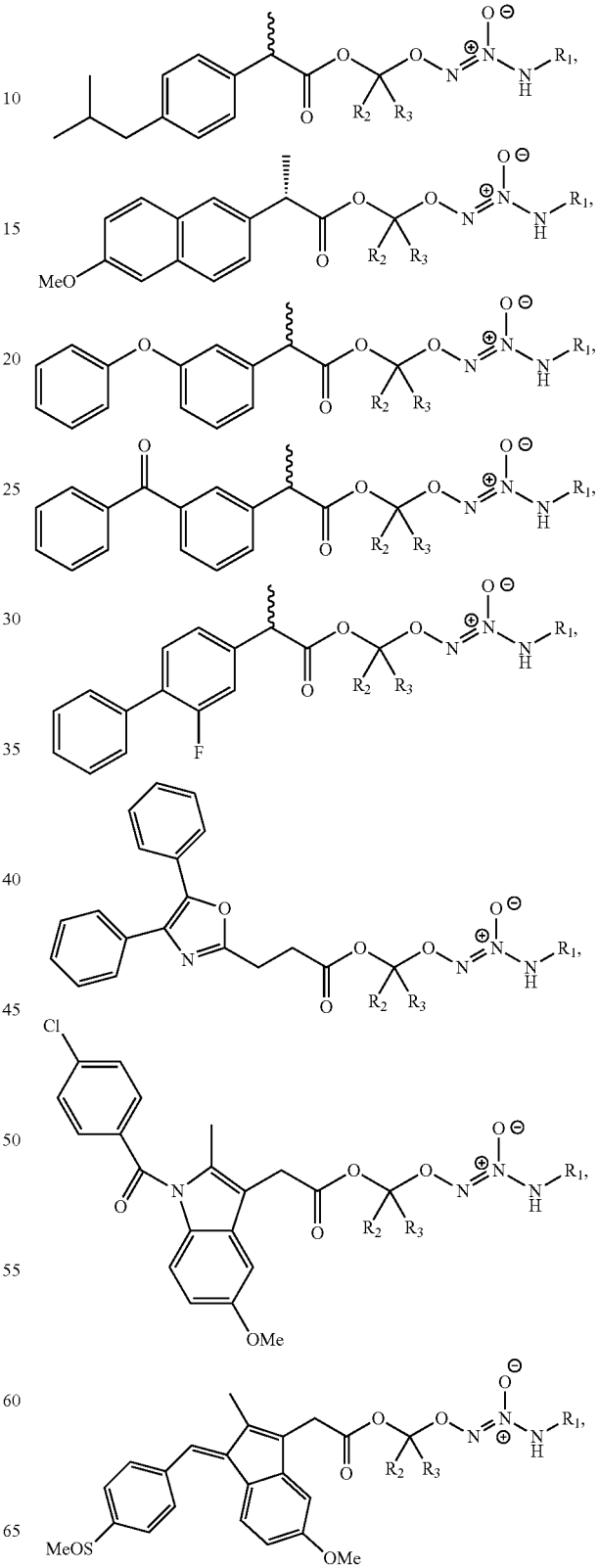

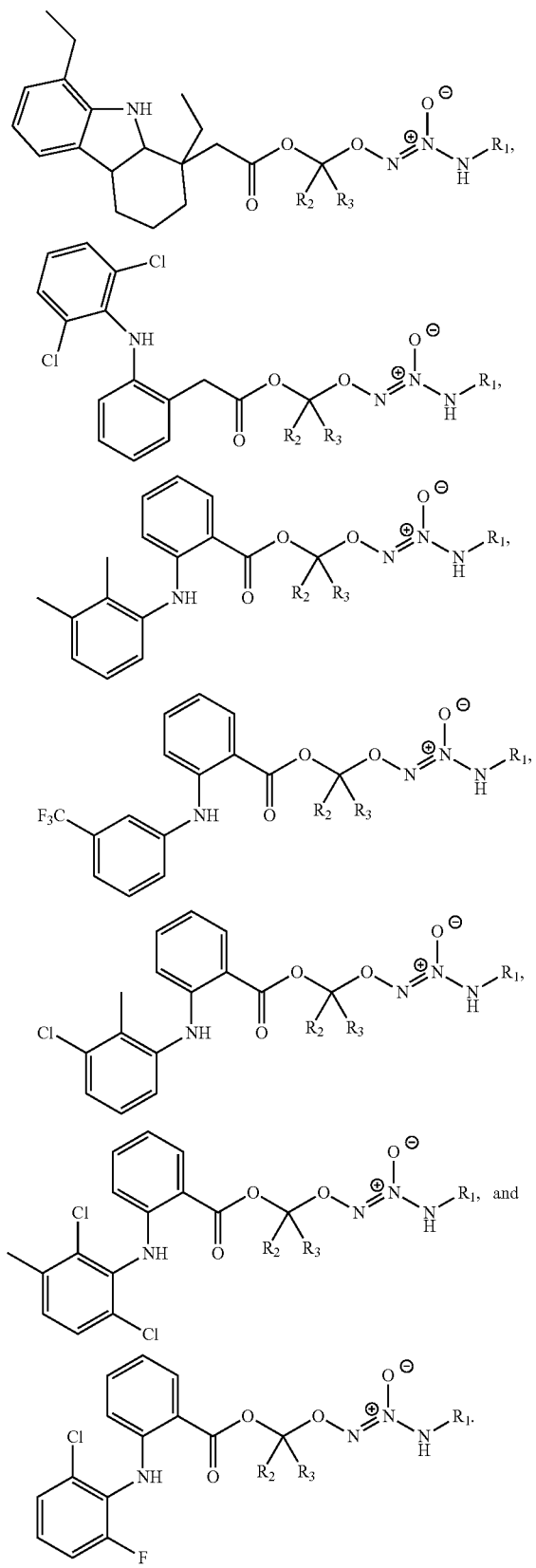

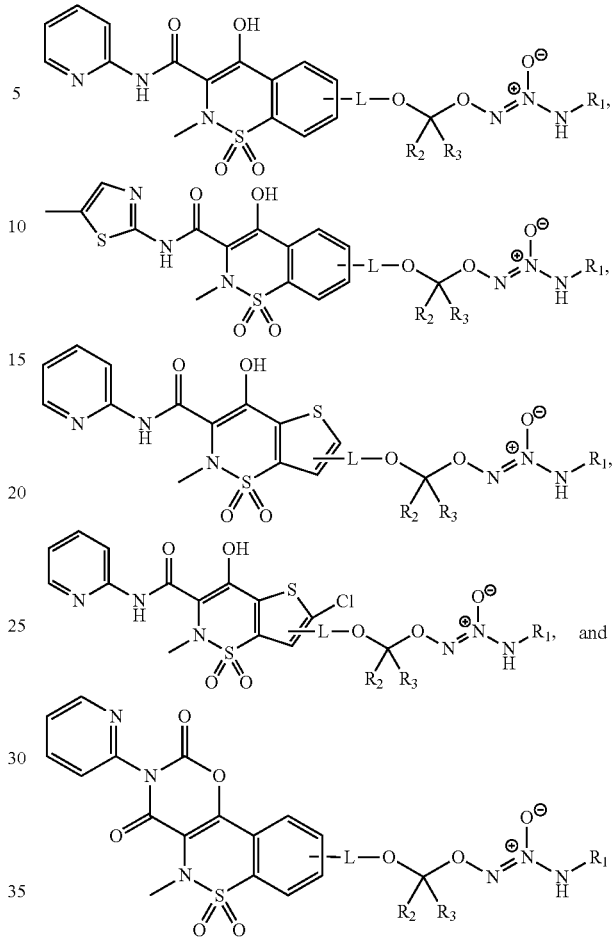

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound

40. The method of any one of clauses 1 to 38, wherein the compound selected from the group consisting of:

41. The method of any one of clauses 1 to 38, wherein the compound selected from the group consisting of:

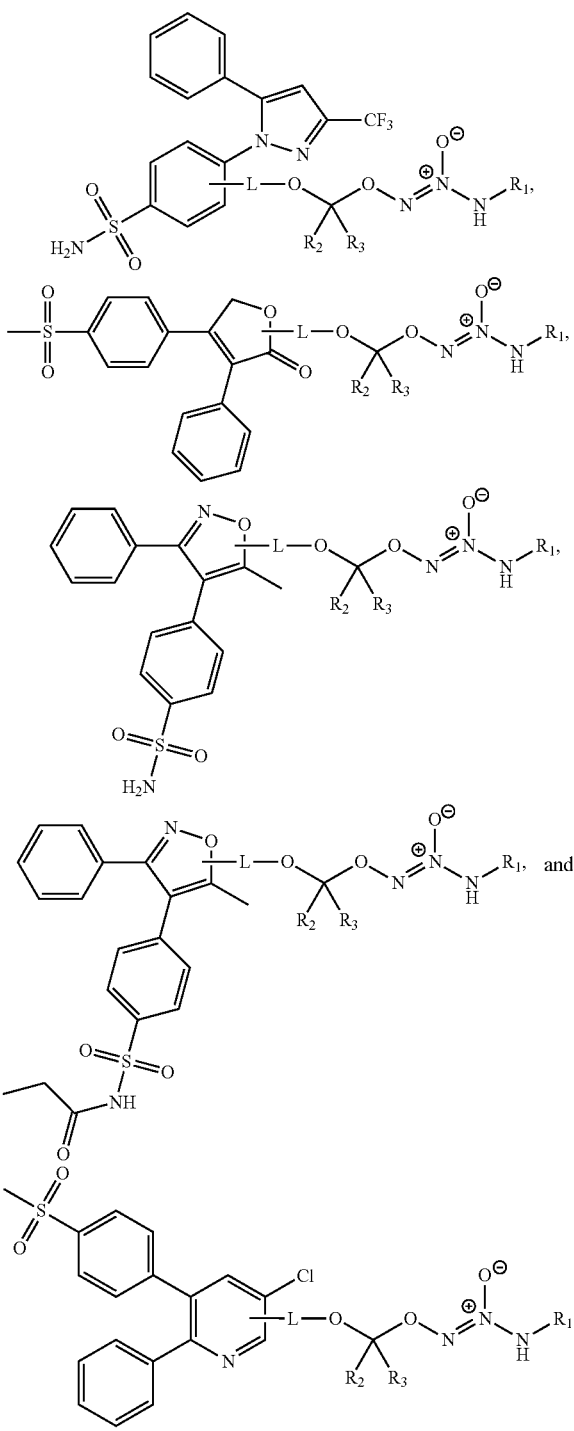

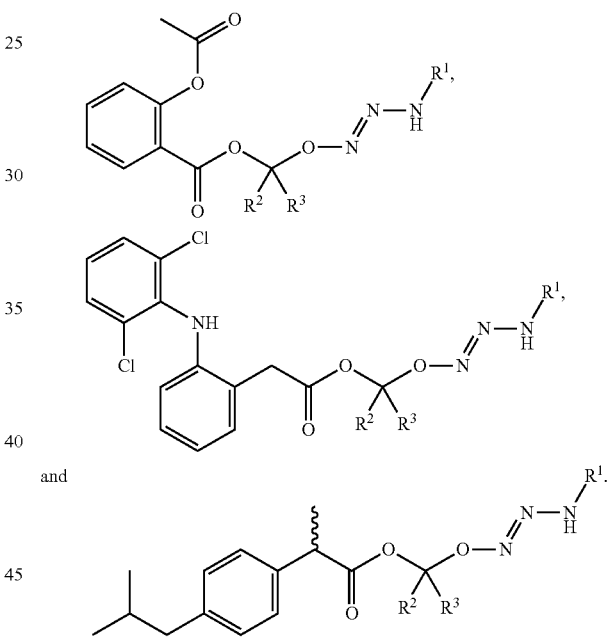

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound.

42. The method of any one of clauses 1 to 41, wherein the NSAID is selected from the group consisting of aspirin, ibuprofen, and diclofenac.

43. The method of any one of clauses 1 to 38, wherein the compound is selected from the group consisting of:

44. The method of any one of clauses 1 to 38, wherein the NSAID is aspirin or salicylic acid.

45. The method of any one of clauses 1 to 38, wherein the compound or salt is:

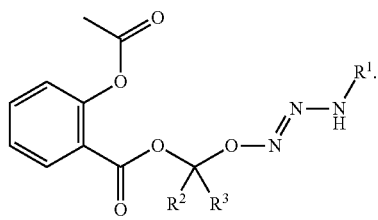

46. A kit comprising a compound of the formula (I) or a pharmaceutically acceptable salt thereof:

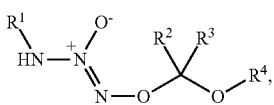

and a therapeutic agent,
wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity.

47. The kit of clause 46, wherein the therapeutic agent is tamoxifen.

48. A kit comprising a compound of the formula (I) or a pharmaceutically acceptable salt thereof:

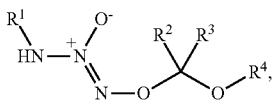

and instructions for the detection of one or more thiols in a cellular protein,
wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity.

49. The kit of any one of clauses 46 to 48, wherein the compound of the formula (I) or pharmaceutically acceptable salt thereof releases HNO at physiological pH.

50. The kit of any one of clauses 46 to 49, wherein $R^1$ is optionally substituted $C_{1-12}$ alkyl, optionally substituted $C_{3-12}$ alkenyl, or optionally substituted $C_{3-8}$ cycloalkyl.

51. The kit of any one of clauses 46 to 50, wherein $R^2$ and $R^3$ are the same or different and each is hydrogen, $C_{1-12}$ alkyl, aryl, or heteroaryl, each of which, other than hydrogen, is optionally substituted.

52. The kit of any one of clauses 46 to 51, wherein $R^2$ and $R^3$ are hydrogen.

53. The kit of any one of clauses 46 to 52, wherein $R^1$ is optionally substituted $C_{1-12}$ alkyl.

54. The kit of any one of clauses 46 to 52, wherein $R^1$ is optionally substituted $C_{1-4}$ alkyl.

55. The kit of any one of clauses 46 to 52, wherein $R^1$ is isopropyl.

56. The kit of any one of clauses 46 to 55, wherein $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino 57. The kit of any one of clauses 46 to 56, wherein $R^5$ is an optionally substituted $C_{1-12}$ alkyl 58. The kit of any one of clauses 46 to 57, wherein the compound of formula (I) is

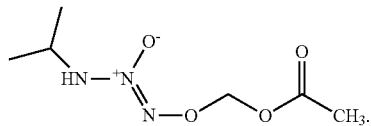

59. The kit of any one of clauses 46 to 57, wherein $R^4$ is an NSAID moiety retaining its NSAID activity 60. The kit of clause 59, wherein said NSAID moiety is a moiety of an NSAID selected from the group consisting of aspirin, propionic acid derivatives, acetic acid derivatives, sulphonanilides, licofelone, enolic acid derivatives, fenamic acid derivatives, and selective COX-2 inhibitors 61. The kit of clause 59, wherein the NSAID is selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, licofenac, and niflumic acid 62. The kit of any one of clauses 46 to 61, wherein the compound is selected from the group consisting of:

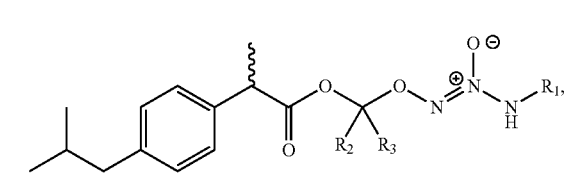

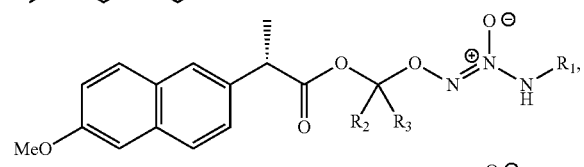

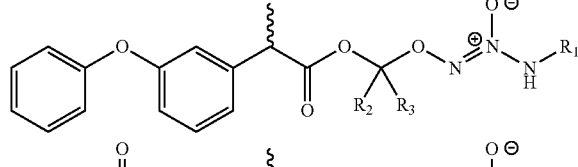

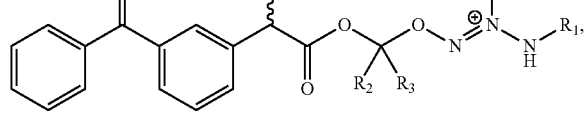

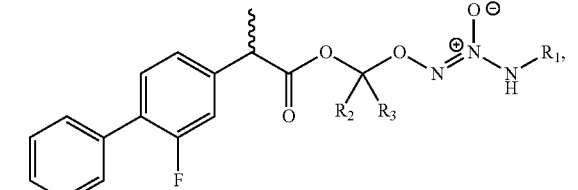

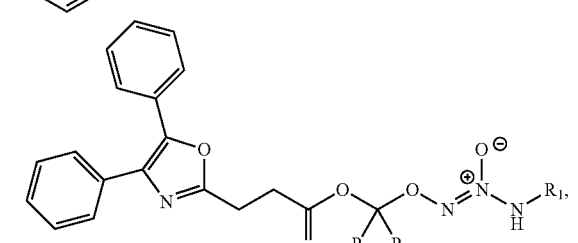

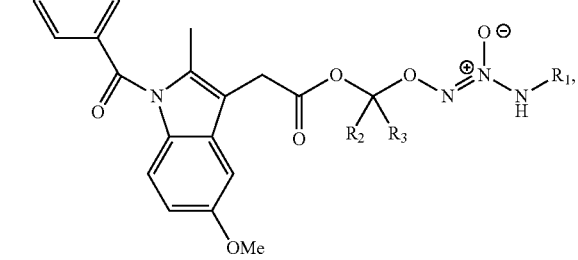

-continued

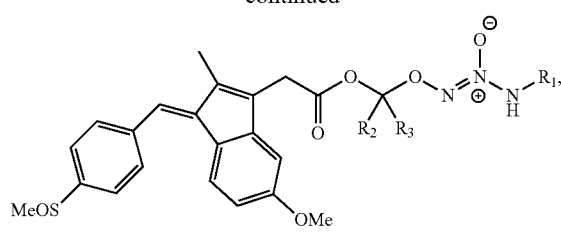

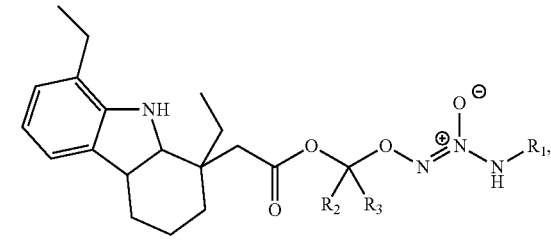

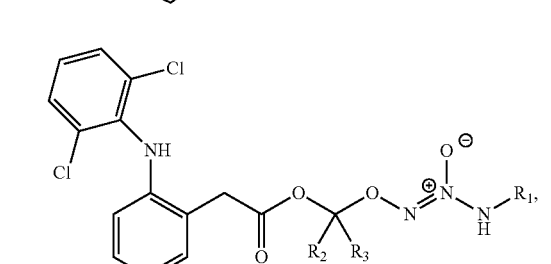

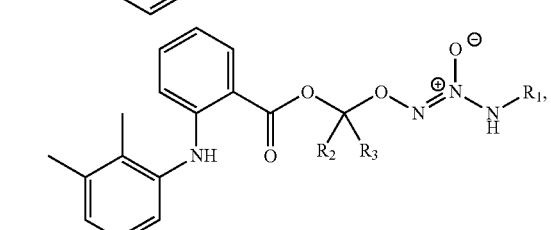

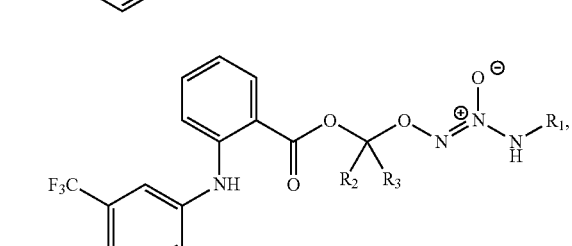

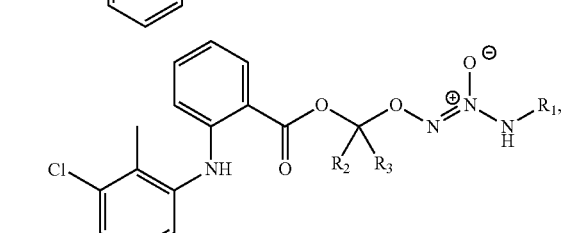

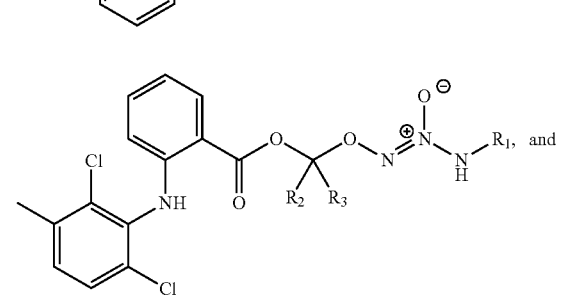

19

-continued

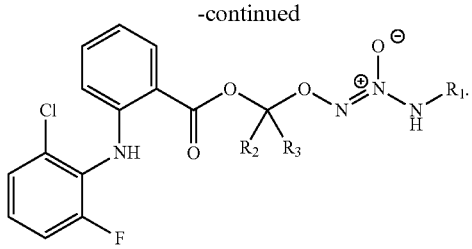

63. The kit of any one of clauses 46 to 57, wherein the compound selected from the group consisting of:

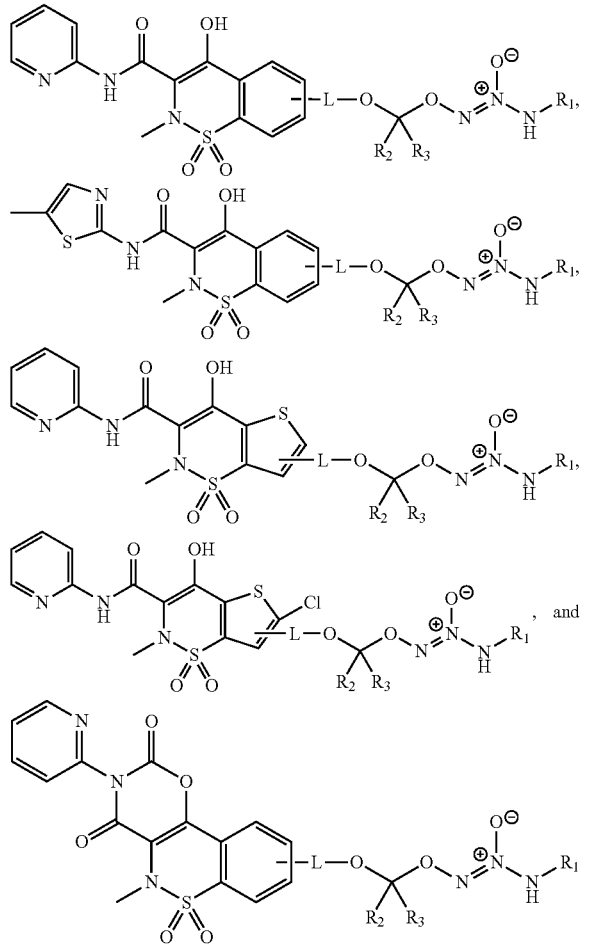

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of

20 halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound

64. The kit of any one of clauses 46 to 63, wherein the compound selected from the group consisting of:

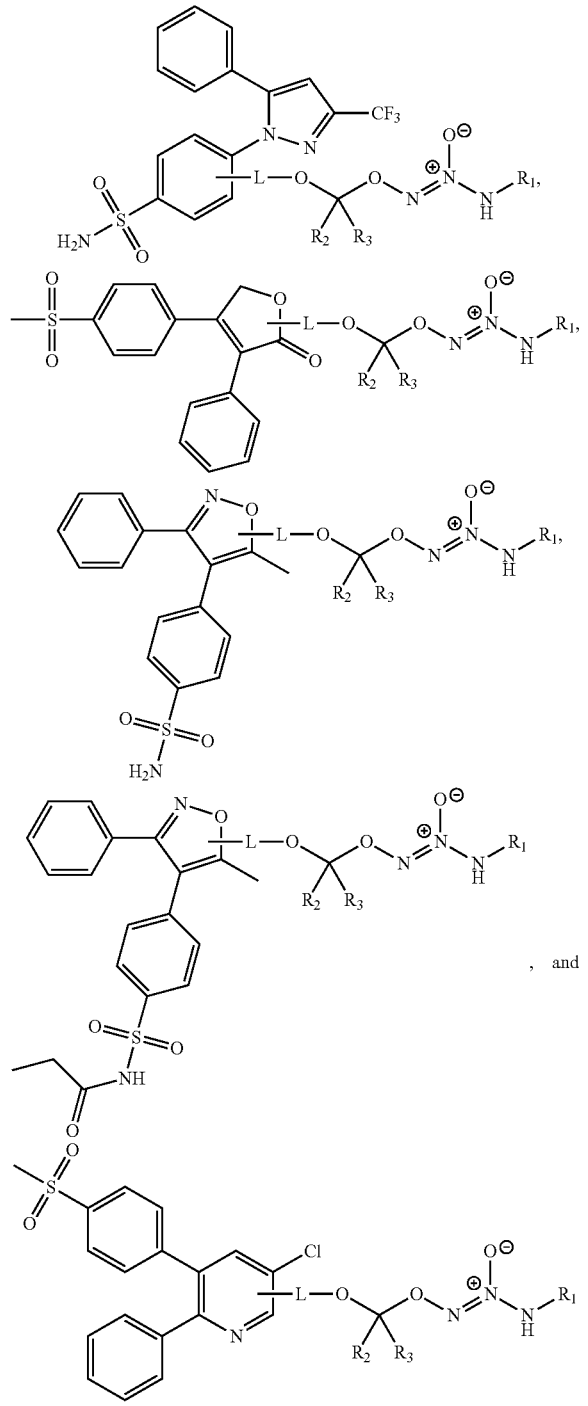

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt of the compound.

65. The kit of any one of clauses 46 to 64, wherein the NSAID is selected from the group consisting of aspirin, ibuprofen, and diclofenac.

66. The kit of any one of clauses 46 to 63, wherein the compound is selected from the group consisting of:

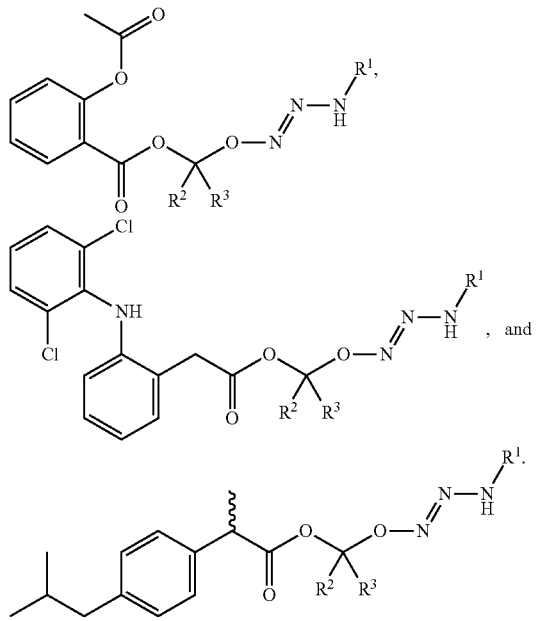

, and

67. The kit of any one of clauses 46 to 63, wherein the NSAID is aspirin.

68. The kit of any one of clauses 46 to 63, wherein the compound or salt is:

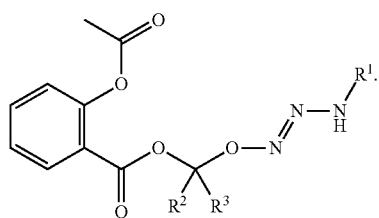

BRIEF DESCRIPTION OF THE DRAWINGS

In FIG. 4A, spectra were collected every 60 s (10-min intervals shown) after dissolving 2 in PBS (pH 7.4) at 37° C., and only loss of the parent compound was observed. In FIG. 4B, the pH was elevated to 12, and scans were collected every 0.5 s (through 2.5 s and 3.5, 5.5, 9.5, and 54.5 shown). In FIG. 4C, porcine liver esterase (20 µL in 3 mL) was added (pH 7.4), and spectra were collected every 10 s. Hydrolysis of 2 ($\lambda_{max}$ 236 nm) to 1 ($\lambda_{max}$ 250 nm) was complete within 40 s (0.067 s$^{-1}$) under these conditions. The rate of decay of 1 in FIG. 4C was comparable to that shown in FIG. 3A (0.0033 s$^{-1}$ vs. 0.0012 s$^{-1}$, respectively). Elevation of the intensity near 200 nm indicated formation of autoxidation products such as nitrite. Deaeration inhibited this peak (data not shown).

DETAILED DESCRIPTION OF THE ILLUSTRATIVE EMBODIMENTS

Figure 1A:
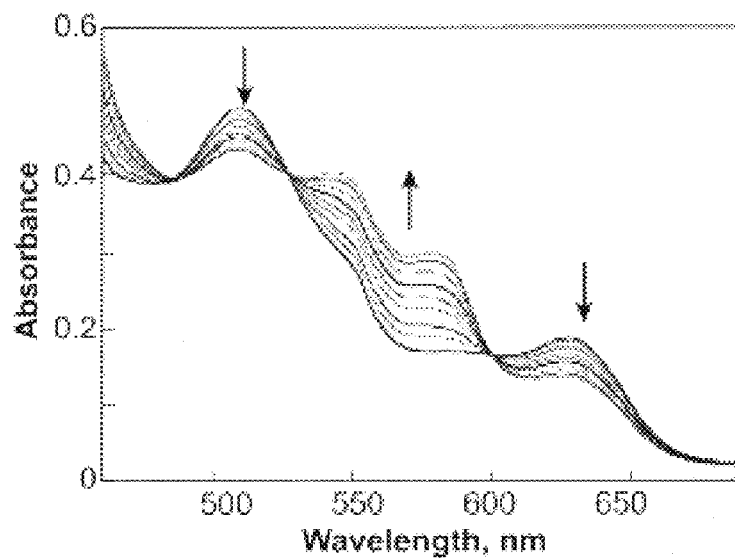
FIGS. 1A and 1B are graphs illustrating the reductive nitrosylation of metMb (50 µM) by (FIG. 1A) IPA/NO, 1 (100 µM), or (FIG. 1B) AcOM-IPA/NO, 2 ($O^2$-(acetoxymethyl) 1-(isopropylamino)diazen-1-ium-1,2-diolate; 100 µM) in an embodiment of the invention. The assay was performed in phosphate buffered saline (PBS), pH 7.4, containing 50 µM DTPA at 37° C. under deaerated conditions and was followed until there were no further spectral changes at 543 and 575 nm (1, 2, 4, 6, 9, 14, 23 and 46 min for 1; 3-107 min in 4- to 10-min intervals shown for 2).

For all of the embodiments described herein, any applicable combination of embodiments is contemplated. Any applicable combination of the embodiments described below is considered to be in accordance with the invention. Any combination of the embodiments described below with the embodiments described in the Summary of Invention section, including the clause list, is considered to be part of the invention.

In one embodiment described herein, a method of inducing DNA damage of a cell is provided. The method comprises the step of administering a compound as described in the instant description to the cell, wherein contacting the cell with the compound induces the DNA damage of the cell.

In another embodiment described herein, a method of binding to a thiol of a cellular protein is provided. The method comprises the step of administering a compound as described in the instant description to a cell comprising the cellular protein, wherein the compound binds to one or more thiols of the cellular protein.

In yet another embodiment described herein, a method of increasing an oxidant level in a cell is provided. The method comprises the step of administering a compound as described in the instant description to the cell, wherein contacting the cell with the compound increases the oxidant level of the cell.

In one embodiment described herein, a method of increasing apoptosis of a population of cells is provided. The method comprises the step of administering a compound as described in the instant description to the population of cells, wherein contacting the compound with the population of cells increases the occurrence of apoptosis in the population of cells.

In another embodiment described herein, a method of decreasing angiogenesis in a population of cells is provided. The method comprises the step of administering a compound as described in the instant description to the population of cells, wherein contacting the compound with the population of cells decreases the occurrence of angiogenesis in the population of cells.

In yet another embodiment described herein, a method of inhibiting metastasis of a cell is provided. The method comprises the step of administering a compound as described in the instant description to the cell, wherein contacting the cell with the compound inhibits the metastasis of the cell.

In one embodiment described herein, a method of modifying a phenotype of a cell is provided. The method comprises the step of administering a compound as described in the instant description to the cell, wherein contacting the cell with the compound modifies the phenotype of the cell.

In another embodiment described herein, a method of decreasing glycolysis in a mammal is provided. The method comprises the step of administering a compound as described in the instant description to the mammal, wherein the compound decreases glycolysis in the mammal.

In yet another embodiment described herein, a method of treating cancer is provided. The method comprises the step of administering a compound as described in the instant description and a therapeutic agent to a mammal, wherein the compound and the therapeutic agent are effective in treating cancer in the mammal.

In some embodiments described herein, a kit is provided. The kit comprises a compound as described in the instant description and a therapeutic agent.

In other embodiments, a kit is provided for the detection of thiols. The kit comprises a compound as described in the instant description and instructions for the detection of one or more thiols in a cellular protein.

In one described embodiment, a method of inducing DNA damage of a cell is provided. The method comprises the step of administering a compound as described in the instant description to the cell, wherein contacting the cell with the compound induces the DNA damage of the cell. As used herein, the term "DNA damage" is an art-recognized term and is used herein to refer to chemical changes to DNA, e.g., damaged (oxidized, alkylated, hydrolyzed, adducted, or cross-linked) bases, single-stranded DNA breaks, and double-stranded DNA breaks. As used herein, the term "contacting" refers to any method in which the compound effects a cell, tissue, or area of interest. The method can utilize a compound of the formula (I) or a pharmaceutically acceptable salt thereof:

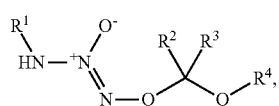

(I)

wherein:

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

$R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$alkylamino, and di-$C_{1-12}$ alkyl-amino; and $R^4$ is —C(=O)$R^5$, wherein $R^5$ is selected from hydrogen, $C_{1-12}$ alkyl, $C_{2-12}$alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or $R^4$ is a non-steroidal anti-inflammatory drug (NSAID) moiety retaining its NSAID activity.

Each of $C_{1-12}$ alkyl, $C_{3-12}$ alkenyl, $C_{3-12}$ alkynyl, $C_{3-8}$ cycloalkyl, aryl, and heteroaryl can be substituted with one or more substituents (e.g., 1 to 5, 1 to 4, 1 to 3, 1 or 2) selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$thioalkoxy, nitro, sulfonato, $C_{1-12}$ acyl, $C_{2-12}$ acyloxy, carboxyl, mercapto, $C_{1-12}$alkoxy-carbonyl, $C_{1-12}$ alkoxy-carbonyloxy, amido, amino, $C_{1-12}$ alkylamino, and di-$C_{1-12}$ alkyl-amino. In some embodiments, one or more substituents are selected from the group consisting of halo, OH, CN, hydroxy-$C_{1-6}$ alkyl, halo-$C_{1-6}$ alkyl, amino-$C_{1-6}$ alkyl, $C_{1-6}$ alkoxy, aryloxy, $C_{1-6}$ thioalkoxy, nitro, sulfonato, $C_{1-6}$ acyl, $C_{2-6}$ acyloxy, carboxyl, mercapto, $C_{1-6}$ alkoxy-carbonyl, $C_{1-6}$ alkoxy-carbonyloxy, amido, amino, $C_{1-6}$ alkylamino, and di-$C_{1-16}$ alkyl-amino. When an aryl or heteroaryl group is substituted with a substituent described herein, a hydrogen on the aryl or heteroaryl ring is replaced with the substituent and this can take place in any of the available hydrogens, e.g., 2, 3, 4, 5, and/or 6-position, if the 1-position is the point of attachment of the aryl group in the compound of the present invention.

In certain embodiments, $R^1$ is optionally substituted $C_{1-12}$ alkyl, optionally substituted alkenyl (e.g., allyl), or optionally substituted $C_{3-8}$ cycloalkyl (e.g., cyclopentyl, cyclohexyl, bicyclo[2.2.1]heptyl) in the compound of formula (I) or a salt thereof. In a preferred embodiment, $R^1$ is optionally substituted $C_{1-12}$ alkyl or $C_{1-4}$ alkyl, e.g., isopropyl or ethyl. In combination with any of the embodiments described herein, $R^2$ and $R^3$ preferably are the same or different and each is selected from the group consisting of hydrogen, $C_{1-12}$ alkyl, aryl, or heteroaryl, each of which, other than hydrogen, is optionally substituted. In combination with any of the embodiments described herein, $R^2$ and $R^3$ are particularly hydrogen.

In certain embodiments, $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino.

In certain embodiments, $R^4$ a non-steroidal anti-inflammatory drug (NSAID) moiety retaining its NSAID activity. The NSAID moiety may be any suitable NSAID moiety. In an embodiment, the NSAID moiety is selected from the group consisting of aspirin, salicylic acid, propionic acid derivatives, acetic acid derivatives, sulphonanilides, licofelone, enolic acid derivatives, fenamic acid derivatives, and selective COX-2 inhibitors. Specific examples of NSAID moieties include, but are not limited to the NSAID is selected from the group consisting of aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxicab, rofecoxib, valdecoxib, parecoxib, lumiracoxib, etoricoxib, nimesulide, licofenac, and niflumic acid.

In any of the above embodiments, $R^2$ and $R^3$ are hydrogen in the compound of formula (I) or a salt thereof and/or $R^1$ is optionally substituted $C_{1-12}$ alkyl and/or $R^4$ is $C(=O)R^5$, wherein $R^5$ is an optionally substituted $C_{1-12}$ alkyl. In a preferred embodiment, the compound of formula (I) is

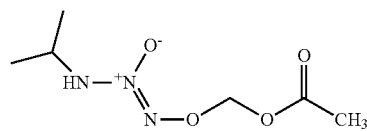

$O^2$-(acetoxymethyl)1-(isopropylamino)diazen-1-ium-1,2-diolate (AcOM-IPA/NO, 2) or a salt thereof.

In an embodiment, the compound of formula (I) or salt thereof is selected from the group consisting of formulas (101)-(115) below, wherein $R^1$, $R^2$, and $R^3$ are as defined above:

(101)
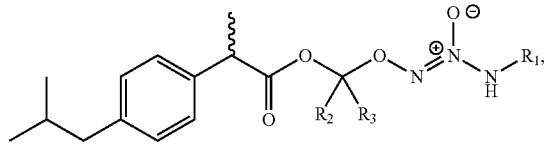

(102)
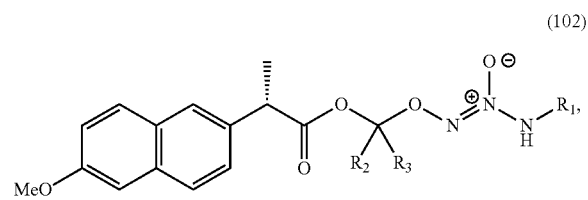

(103)
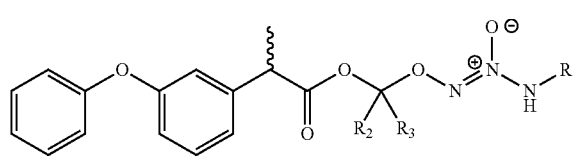

(104)
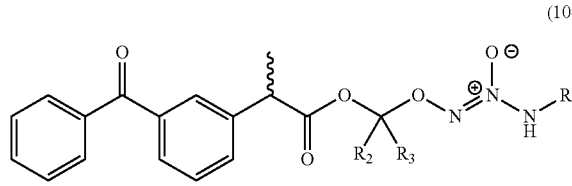

(105)
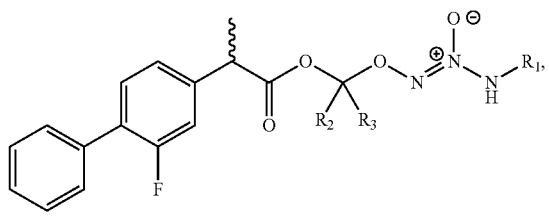

(106)
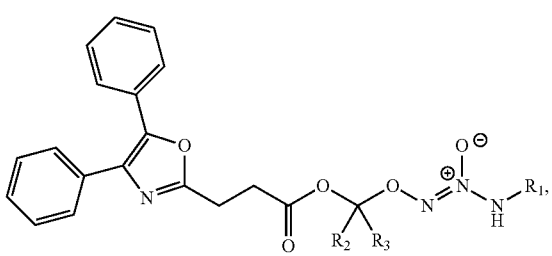

(107)
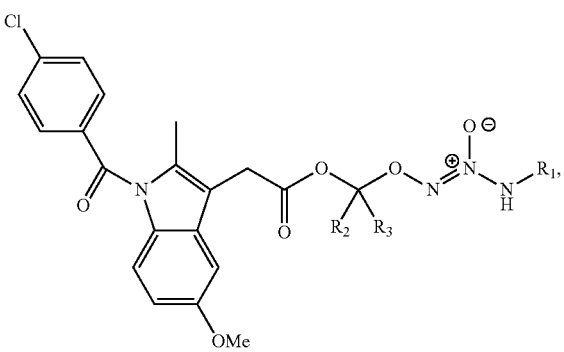

(108)
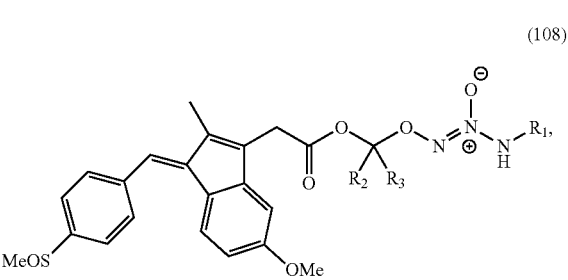

(109)
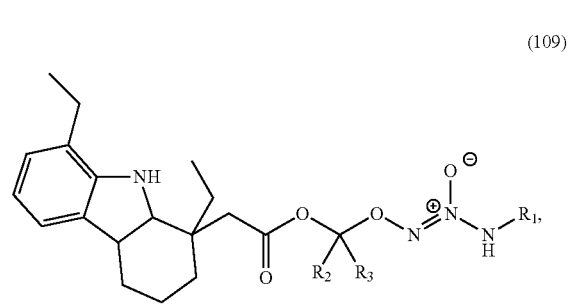

-continued

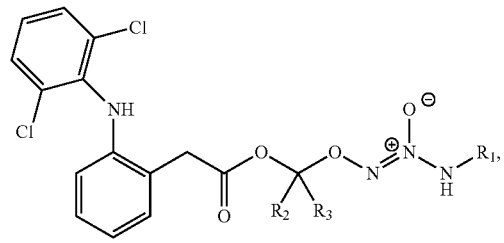
(110)

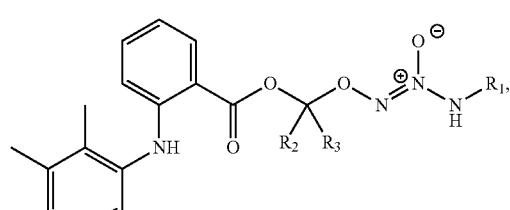
(111)

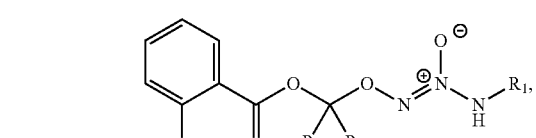
(112)

(113)

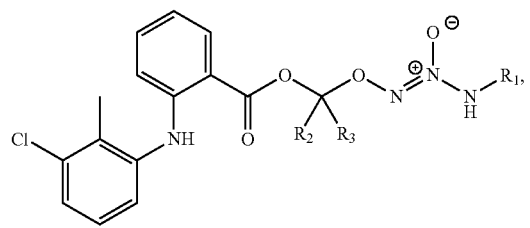
(114)

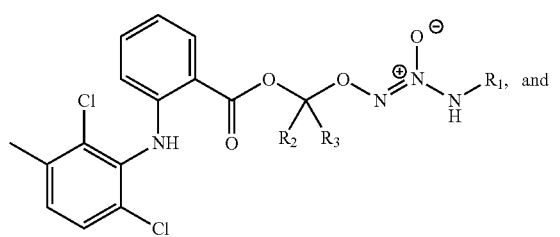
(115)

In an embodiment, the compound of formula (II) or salt thereof is selected from the group consisting of formulas (116)-(125) below, wherein $R^1$, $R^2$, and $R^3$ are as defined above, and wherein L is a linking group selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted arylalkyl, carbonyl, thiocarbonyl, iminocarbonyl, carboxyl, and carbamoyl:

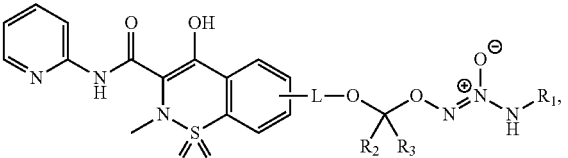
(116)

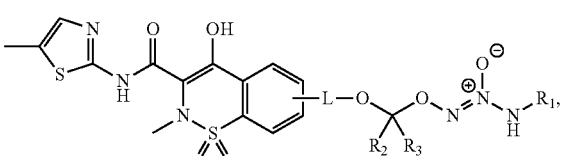
(117)

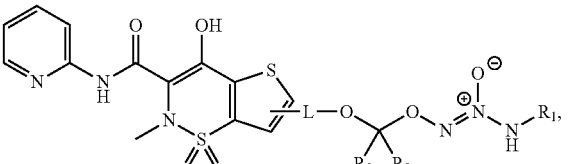
(118)

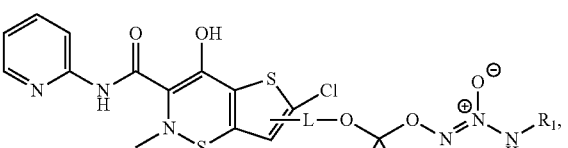
(119)

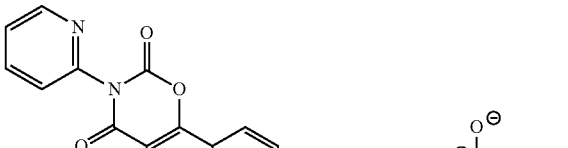
(120)

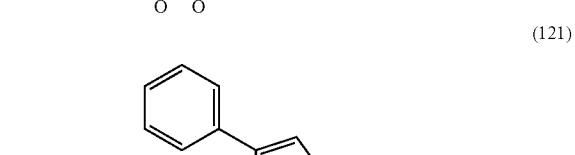
(121)

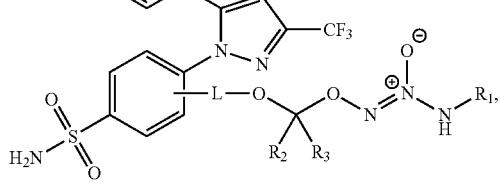

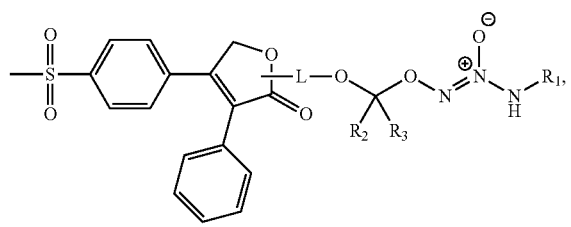

(122)

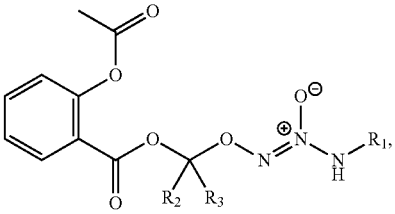

(126)

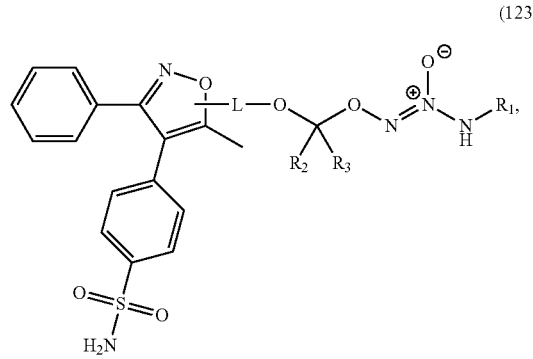

(123)

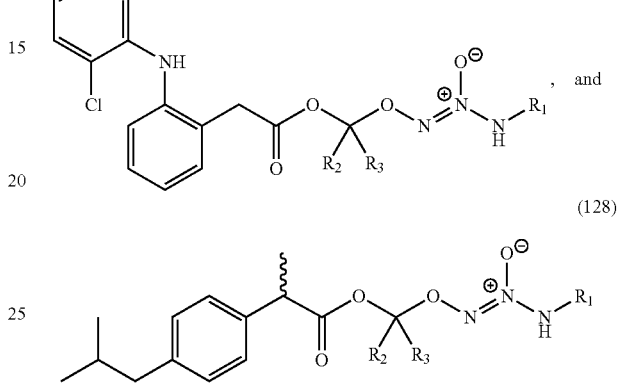

(127)

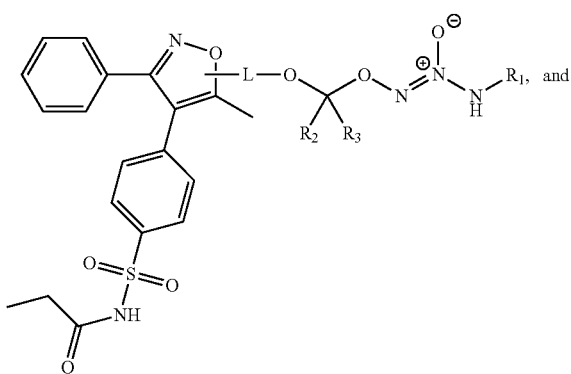

(124)

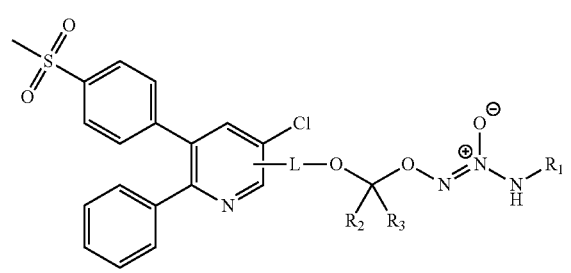

(125)

(128)

Preferably, the NSAID of $R^4$ of the compound or salt of formula (I) is selected from the group consisting of aspirin, ibuprofen, and diclofenac. An especially preferred NSAID is aspirin. In this regard, the compound or salt of formula (I) can be selected from the group consisting of formulas (126)-(128) below, wherein $R^1$, $R^2$, and $R^3$ are as defined above:

In any of the embodiments above, the term "alkyl" implies a straight-chain or branched alkyl substituent containing from, for example, about 1 to about 12 carbon atoms, preferably from about 1 to about 8 carbon atoms, more preferably from about 1 to about 6 carbon atoms. In accordance with an embodiment, the alkyl group is preferably a $C_1$-$C_3$ alkyl. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs, such as in hydroxyalkyl, monohalo alkyl, dihalo alkyl, and trihalo alkyl.

In any of the embodiments above, the term "alkenyl," as used herein, means a linear or branched alkenyl substituent containing from, for example, about 2 to about 12 or about 3 to about 12 carbon atoms, preferably from about 3 to about 8 carbon atoms, more preferably from about 3 to about 6 carbon atoms. In accordance with an embodiment, the alkenyl group is preferably a $C_3$-$C_6$ alkenyl. Examples of alkenyl group include allyl, 1-butenyl, 2-butenyl, 1-pentenyl, 2-pentenyl, 3-pentenyl, 1-hexenyl, and the like. A preferred alkenyl is allyl.

In any of the embodiments above, the term "alkynyl," as used herein, means an alkynyl substituent, linear or branched, containing at least one carbon-carbon triple bond and linear alkynyls contain from, for example, about 3 to about 12 carbon atoms (branched alkynyls are about 4 to about 12 carbons atoms), preferably from about 3 to about 8 carbon atoms (branched alkynyls are preferably from about 4 to about 8 carbon atoms), more preferably from about 3 to about 6 carbon atoms. Examples of such substituents include propynyl, propargyl, n-butynyl, pentynyl, isopentynyl, hexynyl, octynyl, dodecynyl, and the like.

In any of the embodiments above, the term "cycloalkyl," as used herein, means a cyclic alkyl substituent containing from, for example, about 3 to about 8 carbon atoms, preferably from about 5 to about 8 carbon atoms, more preferably from about 5 to about 6 carbon atoms. Examples of such substituents include cyclopropyl, cyclobutyl, cyclopentyl, cyclohexyl, bicyclo[2.2.1]heptyl (e.g., (1s,4s)-bicyclo[2.2.1]heptyl), and the like.

In any of the embodiments above, the term "heterocyclyl" means a stable, saturated, or partially unsaturated monocyclic, bicyclic, and spiro ring system containing 3 to 7 ring members of carbon atoms and other atoms selected from nitrogen, sulfur, and/or oxygen. Preferably, a heterocyclyl is a 5, 6, or 7-membered monocyclic ring and contains one, two, or three heteroatoms selected from nitrogen, oxygen, and/or sulfur. The heterocyclyl may be attached to the parent structure through a carbon atom or through any heteroatom of the heterocyclyl that results in a stable structure. Examples of heterocyclic rings are thiazolinyl, imidazolidinyl, piperazinyl, homopiperazinyl, pyrrolyl, pyrrolinyl, pyrazolyl, pyranyl, piperidyl, and morpholinyl.

In any of the embodiments above, the term "aryl" refers to an unsubstituted or substituted aromatic carbocyclic moiety, as commonly understood in the art, and includes monocyclic, bicyclic, and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ it electrons, according to Hückel's Rule, wherein n=1, 2, or 3.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, thienyl, isothiazolyl, thiazolyl, oxazolyl, isoxazolyl, and oxadiazolyl.

In any of the embodiments above, the term "alkoxy" embraces linear or branched alkyl groups that are attached to divalent oxygen. The alkyl group is the same as described herein. Examples of alkoxy group include methoxy, ethoxy, n-propoxy, isopropoxy, n-butoxy, sec-butoxy, isobutoxy, tert-butoxy, n-pentoxy, isopentoxy, n-hexoxy, and the like. In accordance with an embodiment, the alkoxy group is preferably a $C_1$-$C_3$ alkoxy. The term "thioalkoxy" refers to substituents in which linear or branched alkyl groups are attached to divalent sulfur. The alkyl group is the same as described herein. The term "aryloxy" refers to substituents that have an aryl group attached to divalent oxygen. The aryl group is the same as described herein. Examples of such substituents include phenoxy.

In any of the embodiments above, the term "halo" refers to a halogen selected from the group consisting of fluorine, chlorine, bromine, and iodine, preferably chlorine or bromine.

In any of the embodiments above, the term "amino" refers to —NH$_2$. The term "$C_{1-12}$ alkylamino" refers to a secondary amine substituent with one hydrogen and one $C_{1-12}$ alkyl group directly attached to a trivalent nitrogen atom. The term "di-$C_{1-12}$ alkyl-amino" refers to a tertiary amine substituent with two of the same or different $C_{1-12}$ alkyl groups directly attached to a trivalent nitrogen atom. The $C_{1-12}$ alkyl group is the same as described herein.

In any of the embodiments above, the term "carboxy" refers to the group —C(O)OH. The term "$C_{1-12}$ alkoxycarbonyl" refers to the group —OC(O)R, in which R is a $C_{1-12}$ alkyl group as described herein.

In any of the embodiments above, the terms "$C_1$ acyl" and "$C_{2-12}$ acyl" refer to the groups —C(O)—H and —C(O)—$C_{1-12}$alkyl, respectively. The term "$C_{2-12}$ acyloxy" refers to the group —OC(O)—$C_{1-12}$ alkyl. R is a $C_{1-12}$ alkyl group as described herein.

In any of the embodiments above, the term "amido" refers to the group —C(O)NH$_2$.

In any of the embodiments above, the terms "hydroxyalkyl," "haloalkyl," and "aminoalkyl" refer to an alkyl group, as described herein, that has a hydroxyl, halo, or amino substituent, respectively. The substituent can be on any suitable carbon of the alkyl group (e.g., at the 1-, 2-, 3-, 4-, 5-, 6-, 7-, 8-, 9-, 10-, 11-, or 12-position).

In any of the embodiments above, whenever a range of the number of atoms in a structure is indicated (e.g., a $C_{1-12}$, $C_{1-8}$, $C_{1-6}$, or $C_{1-4}$ etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The compounds of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The invention also includes solvent addition forms ("solvates") of the compounds of the invention. Some compounds have a tendency to trap a fixed molar ratio of solvent molecules in the crystalline solid state, thus forming a solvate. When the compound of formula (I) is placed in a system in which a certain solvent is brought to a vapor form, in some situations, the compound, together with the molecules of the solvent, forms a crystal. The material formed by crystallization of the compound of formula (I) and the solvent in a three-dimensional order is called a solvate herein. The solvent can be associated with a crystalline solid form of a compound of formula (I) in various ways. The interaction can be due to weak binding (e.g., hydrogen bonding, van der Waals, and dipole-dipole) or by entrapment (e.g., liquid inclusion).

A solvate can be formed by a variety of methods, many of which are known in the art. A compound of formula (I) can be combined with one or more solvents by any suitable method (e.g., crystallization, lyophilization, film coating, spray drying, suspension, wetting, grinding, vapor sorption, etc.). For example, a compound of formula (I) can be combined with a particular solvent(s) and heated to boiling. The solution can then be slowly cooled to allow formation of the solvate crystals. Cooling can occur at room temperature or at a reduced temperature (e.g., an ice bath and/or refrigerated conditions). Controlling the temperature can be influential in the formation of solvates. Typically a lower temperature favors solvate formation. The formed solvate can be characterized by analytical methods such as thermogravimetric analysis (TGA), differential scanning calorimetry (DSC) alone or with infrared (IR) and/or mass spectrometry, x-ray powder diffraction, moisture sorption experiments, hot-stage polarized light microscopy, or a combination of these methods. Various techniques to prepare solvates are known in the art. See, e.g., J. Keith Guillory, "Generation of Polymorphs, Hydrates, and Solvates, and Amorphous Solids," *Drugs and the Pharmaceutical Sciences*, 95 (Polymorphism in Pharmaceutical Solids): 183-226 (1999); and Greisser, U., "The Importance of Solvates" in *Polymorphism*, Hilfiker, R., Ed., (Wiley-VCH Verlag GmbH & Co. KGaA: Weinheim, Germany, 2006), pages 211-233.

A solvate means a solvent addition form that contains either stoichiometric or non-stoichiometric amounts of solvent. A stoichiometric solvate implies a fixed, although not necessarily integral, ratio of solvent to compound (e.g., a solvent coordination number of 1, 2, 3, 4, 5, 6, etc.). A preferred solvent coordination number of a stoichiometric solvate is 1. A non-stoichiometric solvate can be an interstitial solid solution or an interstitial co-crystal. The solvent content of a solvate can be any suitable value, including a multiple of the molar compound ratio such that the solvent coordination number is a non-integral number (e.g., 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, etc.). The amount of solvent in the structure generally depends on the partial pressure of the solvent in the environment of the solid and the temperature (Greisser, U., "The Importance of Solvates" in *Polymorphism*, Hilfiker, R., Ed., (Wiley-VCH Verlag GmbH & Co. KGaA: Weinheim, Germany, 2006), pages 211-233).

The solvent can be any suitable solvent, i.e., the solvent is not particularly limited as long as a solvate of the compound of formula (I) can be formed. Solvents usable for solvate formation include water, alcohols, ethers, esters, alkanes, dichloromethane, chloroform, acetone, acetonitrile, toluene, tetrahydrofuran, dimethylformamide (DMF), dimethyl sulfoxide (DMSO), dioxane, and combinations thereof. In some embodiments, the solvate contains a mixture of solvents, such as a combination of two or more of the aforementioned solvents. Preferably the solvent should have relatively low toxicity and can be removed from the compound of formula (I) to a level that is acceptable according to The International Committee on Harmonization (ICH) guidelines ("ICH Q3C Impurities: Guideline for Residual Solvents, International Conference on Harmonization of Technical Requirements for Registration of Pharmaceuticals for Human Use," Geneva, Switzerland, July 1997). Preferred solvents include water, alcohols, ethers, esters, and alkanes. If the solvent is water, the solvate formed is a "hydrate," whereas when the solvent is alcohol, the solvate formed is an "alcoholate." Specific examples of preferred solvents usable for solvate formation include water, $C_{1-4}$ alcohol (e.g., methanol, ethanol, propanol, isopropanol, and n-butanol), $C_{1-4}$ ether (e.g., diethyl ether), an ester of a $C_{1-6}$ (preferably $C_{1-4}$) alkyl acetate (e.g., methyl acetate, ethyl acetate, propyl acetate, and butyl acetate), a $C_{5-7}$ alkane (e.g., pentane, hexane, and heptane), and combinations thereof. Mixed solvates include, for example, water/ethanol, water/methanol, water/acetone, water/hexane, and water/DMF.

Nitric oxide release from the diazeniumdiolated compounds described herein can be determined/detected using known techniques such as those described in U.S. Pat. Nos. 6,511,991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide*, 6(2): 135-41 (2002); and Kitamura et al., "In vivo nitric oxide measurements using a microcoaxial electrode," *Methods Mol. Biol.*, 279: 35-44 (2004), which are incorporated herein by reference. In general, the amount of NO produced can be detected by a chemiluminescence method, electrochemical method, and/or an absorbance method. In addition, nitric oxide assay kits are commercially available.

Angeli's salt and IPA/NO (1) hydrolyze by the following mechanisms. An embodiment of the compound of formula (I) wherein $R^4$ is —C(=O)$R^5$, for example, AcOM-IPA/NO, 2, undergoes hydrolysis to the deprotected form of the compound of formula (I) i.e., $R^1NH$—$N_2O_2^-$ (and formaldehyde and acetate), in the presence of esterase. It was surprisingly discovered, however, that the deprotected form is not detected as an intermediate in the absence of esterase (i.e., uncatalyzed hydrolysis). This unexpected phenomenon is even more evident at an elevated pH. In a specific example of IPA/NO (1) and AcOM-IPA/NO (2), 1 hydrolyzes 100-fold more slowly than 2 at pH 11, but nuclear magnetic resonance (NMR) signals for 1 could not be seen during the rapid hydrolysis of 2 at this pH. By hydrolyzing an order of magnitude slower at physiological pH than 1, 2 generates a correspondingly lower steady-state concentration of HNO, minimizing its dimerization/dehydration to $N_2O$ and making the HNO much more efficiently available to biological targets (e.g., metmyoglobin and glutathione). Thus, this embodiment of the compound of formula (I) generates reliable, controlled fluxes of HNO, such that the compound of formula (I) is a prodrug of HNO for therapeutic uses. Nitroxyl (HNO) release from the compound of formula (I) or a salt thereof can be determined/detected using known techniques and/or by the methods described herein.

ether in the presence of a base such as sodium ethoxide to provide the NO-adduct. The NO adduct can be reacted with for example chloromethylmethylsulfide, which reacts with for example sulfuryl chloride in a solvent such as dichloromethane to provide the chloromethyl intermediate. The chloromethyl intermediate can be reacted with for example a carboxyl group to provide the substituted diazene-1-ium-1,2-diolates.

The invention also provides a pharmaceutical composition comprising (a) the compound of formula (I) or a salt thereof and (b) a pharmaceutically acceptable carrier. In the pharmaceutical compositions described herein, any suitable pharmaceutically acceptable carrier can be used, and such carriers are well known in the art. The choice of carrier will be determined, in part, by the particular site to which the pharmaceutical composition is to be administered and the particular method used to administer the pharmaceutical composition.

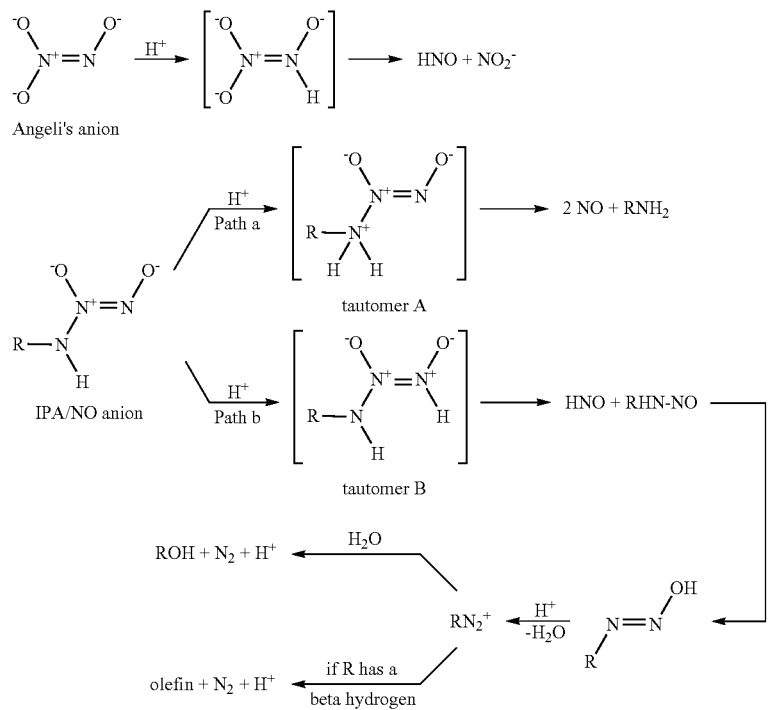

A compound of formula (I) where $R^4$ is $—C(=O)R^5$, or a salt thereof, can be prepared by the following method. An unprotected diazeniumdiolate can be prepared first (i.e., $R^1NH—N_2O_2^-$) by reacting a primary amine of the formula $NH_2R^1$, in which $R^1$ is described herein, with nitric oxide gas. The unprotected diazeniumdiolate can then subsequently be protected with the desired substituted methyl carboxylate (e.g., LG-CR$_2$R$_3$OC(O)(C$_{1-12}$ alkyl), LG-CR$_2$R$_3$OC(O)(C$_{2-12}$alkenyl), LG-CR$_2$R$_3$OC(O)(C$_{2-13}$ alkynyl), LG-R$_2$R$_3$OC(O)(C$_{3-8}$ cycloalkyl), LG-R$_2$R$_3$OC(O)(heterocyclyl), LG-R$_2$R$_3$OC(O)(aryl), LG-R$_2$R$_3$OC(O)(heteroaryl), in which LG is a leaving group (e.g., Br, Cl, etc.)).

Embodiments of the compounds of formula (I) or a salt thereof where $R^4$ is a non-steroidal anti-inflammatory drug (NSAID) moiety retaining its NSAID activity can be synthesized by reaction of amines with NO in a solvent such as Suitable formulations include aqueous and non-aqueous solutions, isotonic sterile solutions, which can contain antioxidants, buffers, bacteriostats, and solutes that render the formulation isotonic with the blood or other bodily fluid of the intended recipient, and aqueous and non-aqueous sterile suspensions that can include suspending agents, solubilizers, thickening agents, stabilizers, and preservatives. In one embodiment, the pharmaceutically acceptable carrier is a liquid that contains a buffer and a salt. The formulation can be presented in unit-dose or multi-dose sealed containers, such as ampoules and vials, and can be stored in a freeze-dried (lyophilized) condition requiring only the addition of the sterile liquid carrier immediately prior to use. Extemporaneous solutions and suspensions can be prepared from sterile powders, granules, and tablets. In one embodiment, the pharmaceutically acceptable carrier is a buffered saline solution.

Further carriers include sustained-release preparations, such as semipermeable matrices of solid hydrophobic polymers containing the active agent, which matrices are in the form of shaped articles (e.g., films, liposomes, or microparticles). Alternatively, a delayed release formulation, including an enteric coating comprising a compound of formula (I) or a salt thereof, can be prepared.

The pharmaceutical composition can include carriers, thickeners, diluents, buffers, preservatives, surface active agents, and the like. The pharmaceutical compositions can also include one or more additional active ingredients, such as antimicrobial agents, anti-inflammatory agents, anesthetics, and the like.

The pharmaceutical composition comprising the compound of formula (I) or a salt thereof can be formulated for any suitable route of administration, depending on whether local or systemic treatment is desired, and on the area to be treated. The pharmaceutical composition can be formulated for parenteral administration, such as intravenous, intraperitoneal, intrathecal, intraarterial, subcutaneous, intramuscular, or intratumoral injection. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier immediately prior to use. Extemporaneous injection solutions and suspensions can be prepared from sterile powders, granules, and tablets of the kind previously described.

The pharmaceutical composition comprising the compound of formula (I) or a salt thereof can be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The pharmaceutical composition also can be administered orally. Oral compositions can be in the form of powders or granules, suspensions or solutions in water and/or non-aqueous media, capsules, pills, sachets, or tablets. Thickeners, flavorings, diluents, emulsifiers, dispersing aids, or binders may be desirable.

If desired, tablets or pills can be coated with a sugar coating, or a gastric or enteric coating agent. The term "enteric coating" means a coating or barrier applied to a dosage form that can control the location in the digestive system where the compound of formula (I) or a salt thereof is absorbed. For example, an enteric coating can be used to protect the drug from the destructive action of the enzymes or low pH environment of the stomach. In certain embodiments, the enteric coated dosage form can be regarded as a type of delayed release dosage form. Enteric coatings work by presenting a surface that is substantially stable at acidic pH, but breaks down at higher pH to allow release of the drug in the intestine.

An enteric coating can comprise an enteric polymer, which is a polymeric substance that when used in an enteric coating, is substantially insoluble and/or substantially stable under acidic conditions exhibiting a pH of less than about 5 and which is substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coating. Enteric polymers can be combined with other pharmaceutically acceptable excipients to either facilitate processing of a coat comprising the enteric polymer or to alter the functionality of the coating.

Additionally, the compound of formula (I) or a salt thereof can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable carriers and their formulations are further described in A. R. Gennaro, ed., *Remington: The Science and Practice of Pharmacy* (19th ed.), Mack Publishing Company, Easton, Pa. (1995).

The compound or a pharmaceutical composition comprising at least one compound of formula (I) or a salt thereof can be administered in or on a device that allows controlled or sustained release of the compound of formula (I) or a salt thereof, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the active agents. The pharmaceutical compositions of the inventive method also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid. Of course, administration of the compound or pharmaceutical composition can be accomplished via any route that efficiently delivers the active agents to the target tissue.

The inventive methods comprise administering an effective amount of a compound of formula (I) or a salt thereof. An "effective amount" means an amount sufficient to show a meaningful benefit in an individual, e.g., reducing the adverse effects of, treatment, healing, prevention, delay of onset, or amelioration of other relevant medical condition(s) associated with a particular disorder. Preferably, one or more symptoms of the disorder are prevented, reduced, or eliminated subsequent to administration of a compound of formula (I) or a salt thereof, thereby effectively treating the disorder to at least some degree.

Effective amounts may vary depending upon the biological effect desired in the individual, condition to be treated, and/or the specific characteristics of the compound of formula (I) or a salt thereof, and the individual. In this respect, any suitable dose of the compound of formula (I) or a salt thereof can be administered to the patient (e.g., human), according to the type of disorder to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or a salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I) or (II) comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

In some embodiments, the DNA damage comprises deamination of one or more base pairs in the cell. As used herein, the term "deamination" is well known in the art and refers to removal of an amine group from a molecule. In other embodiments, the DNA damage comprises cleavage of the DNA.

In certain embodiments, the cell is a cancer cell. In other embodiments, the cancer cell is a proliferating cancer cell. In some embodiments, the cancer cell is located in an oxygenated region of a tumor. In other embodiments, the cancer cell is located in a non-oxygenated region of a tumor.

In one described embodiment, a method of binding to a thiol of a cellular protein is provided. The method comprises the step of administering a compound as described in the instant description to a cell comprising the cellular protein, wherein the compound binds to one or more thiols of the cellular protein. As used herein, the term "binding" is well known in the art and refers to an affinity between two molecules, one of which is a thiol of a cellular protein. In some embodiments, the binding is formed via HNO donation, for example via formation of $RSONH_2$. The embodiments regarding the compound of the formula (I) or a pharmaceutically acceptable salt thereof and the embodiments regarding cell types as described for the methods above also apply to the method of binding to a thiol of a cellular protein.

In one described embodiment, a method of increasing an oxidant level in a cell is provided. The method comprises the step of administering a compound as described in the instant description to the cell, wherein contacting the cell with the compound increases the oxidant level of the cell. As used herein, increasing an oxidant level is associated with increased production of oxidizing species and/or a significant decrease in the effectiveness of antioxidant defenses associated with a cell. The embodiments regarding the compound of the formula (I) or a pharmaceutically acceptable salt thereof and the embodiments regarding cell types as described for the methods above also apply to the method of increasing an oxidant level in a cell.

In one described embodiment, a method of increasing apoptosis of a population of cells is provided. The method comprises the step of administering a compound as described in the instant description to the population of cells, wherein contacting the compound with the population of cells increases the occurrence of apoptosis in the population of cells. As used herein, the term "apoptosis" is well known in the art and refers to a mechanism of programmed cell death. In some embodiments, apoptosis can occur via a caspase signaling cascade. In one embodiment, the caspase is caspase-3. The embodiments regarding the compound of the formula (I) or a pharmaceutically acceptable salt thereof and the embodiments regarding cell types as described for the methods above also apply to the method of increasing apoptosis of a population of cells.

In one described embodiment, a method of decreasing angiogenesis in a population of cells is provided. The method comprises the step of administering a compound as described in the instant description to the population of cells, wherein contacting the compound with the population of cells decreases the occurrence of angiogenesis in the population of cells. As used herein, the term "angiogenesis" is well known in the art and refers to the growth of new blood vessels. The embodiments regarding the compound of the formula (I) or a pharmaceutically acceptable salt thereof and the embodiments regarding cell types as described for the methods above also apply to the method of decreasing angiogenesis in a population of cells.

In one described embodiment, a method of inhibiting metastasis of a cell is provided. The method comprises the step of administering a compound as described in the instant description to the cell, wherein contacting the cell with the compound inhibits the metastasis of the cell. As used herein, the term "metastasis" is well known in the art and refers to the spread of a cancer or disease from one cell to another cell that is not directly connected with the first cell. The embodiments regarding the compound of the formula (I) or a pharmaceutically acceptable salt thereof and the embodiments regarding cell types as described for the methods above also apply to the method of inhibiting metastasis of a cell.

In one described embodiment, a method of modifying a phenotype of a cell is provided. The method comprises the step of administering a compound as described in the instant description to the cell, wherein contacting the cell with the compound modifies the phenotype of the cell. As used herein, the term modifying refers to changing one phenotype to a second phenotype. In one embodiment, an estrogen receptor negative (ER(−)) cell is modified to an estrogen receptor positive (ER(+)) cell. The embodiments regarding the compound of the formula (I) or a pharmaceutically acceptable salt thereof and the embodiments regarding cell types as described for the methods above also apply to the method of modifying a phenotype of a cell.

In one described embodiment, a method of decreasing glycolysis in a mammal is provided. The method comprises the step of administering a compound as described in the instant description to the mammal, wherein the compound decreases glycolysis in the mammal. As used herein, the term "glycolysis" is well known in the art and refers to the metabolic pathway that converts glucose $C_6H_{12}O_6$, into pyruvate, $CH_3COCOO^-+H^+$. As used herein, the term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

In some embodiments, the decrease of glycolysis comprises an inhibition of glyceraldehyde 3-phosphate dehydrogenase (GAPDH) activity. In other embodiments, the inhibition of GAPDH activity is associated with a cancer cell. The embodiments regarding the compound of the formula (I) or a pharmaceutically acceptable salt thereof and the embodiments regarding cell types as described for the methods above also apply to the method of decreasing glycolysis in a mammal.

In one described embodiment, a method of treating cancer is provided. The method comprises the step of administering a compound as described in the instant description and a therapeutic agent to a mammal, wherein the compound and the therapeutic agent are effective in treating cancer in the mammal. As used herein, a "therapeutic agent" is any compound that is used for the treatment of cancer other than the compounds of the formula (I) or pharmaceutically acceptable salts thereof as described in the present disclosure. In one embodiment, the therapeutic agent is tamoxifen. In other embodiments, the therapeutic is any drug known in the art which is cytotoxic, enhances tumor permeability, inhibits tumor cell proliferation, promotes apoptosis, decreases anti-apoptotic activity in target cells, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysins, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vinca alkaloids, such as vincristine, vinblastine, vindesine, vinorelbine and analogs and derivative thereof such as deacetylvinblastine monohydrazide (DAVLBH), colchicine, colchicine derivatives, allocolchicine, thiocolchicine, trityl cysteine, halicondrin B, dolastatins such as dolastatin 10, amanitins such as a amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art recognized drug or toxin.

In another embodiment, the therapeutic agent is selected from a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, everolimus, ispinesib, budesonide, dasatinib, an epothilone, a maytansine, and a tyrosine kinase inhibitor, including analogs and derivatives of the foregoing. In another embodiment, the therapeutic agent is selected illustratively from a vinca alkaloid, a cryptophycin, bortezomib, thiobortezomib, a tubulysin, aminopterin, a rapamycin, such as everolimus or sirolimus, paclitaxel, docetaxel, doxorubicin, daunorubicin, everolimus, α-amanatin, verucarin, didemnin B, geldanomycin, purvalanol A, ispinesib, budesonide, dasatinib, an epothilone, a maytansine, and a tyrosine kinase inhibitor, including analogs and derivatives of the foregoing.

In some embodiments, the cancer is selected from the group consisting of breast cancer, lung cancer, and prostate cancer. In one embodiment, the cancer is breast cancer. In some embodiments, the breast cancer is an estrogen receptor negative (ER(−)) breast cancer.

In other embodiments, the an estrogen receptor positive (ER(+)) breast cancer. In certain embodiments, the cancer is located in an oxygenated region of a tumor. In yet other embodiments, the cancer is located in a non-oxygenated region of a tumor.

In one described embodiment, a kit is provided. The kit comprises a compound as described in the instant description and a therapeutic agent. The embodiments regarding the compound of the formula (I) or a pharmaceutically acceptable salt thereof and the embodiments regarding cell types as described for the methods above also apply to the kits described herein. In one embodiment, the therapeutic agent is tamoxifen.

In another described embodiment, a kit is provided for the detection of thiols. The kit comprises a compound as described in the instant description and instructions for the detection of one or more thiols in a cellular protein. The embodiments regarding the compound of the formula (I) or a pharmaceutically acceptable salt thereof and the embodiments regarding cell types as described for the methods above also apply to the kits described herein.

In another embodiment, the methods, uses, and compositions described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

Example 1

Synthesis of Compounds of Present Disclosure

This example demonstrates a method of synthesis of $O^2$-(acetoxymethyl) 1-(isopropylamino)diazen-1-ium-1,2-diolate (AcOM-IPA/NO) (2) in accordance with an embodiment of the invention.

A solution of bromomethyl acetate (867 mg, 5.67 mmol) in 3 mL of THF was reacted with a slurry of IPA/NO (800 mg, 5.67 mmol, in 10 mL of DMSO) at room temperature. The reaction mixture was stirred overnight whereupon 15 mL of water is added and stirring was continued for another 10 min. The residue was extracted with dichloromethane, washed with 5% sodium bicarbonate, dried over anhydrous sodium sulfate, filtered, and evaporated in vacuo to give a colorless oil. Column chromatography was performed using hexane:acetone (4:1) to give the desired product 2 (880 mg, 81%): UV (ethanol) $\lambda_{max}$ (ε) 240 nm (8.7 mM$^{-1}$ cm$^{-}$); NMR (CDCl$_3$) δ1.19 (d, J=6.4 Hz, 6H), 2.12 (s, 3H), 4.00 (sept, J=6.4 Hz, 1H), 5.75 (s, 2H), 6.25 (d, J=9.1 Hz, 1H); $^{13}$C NMR (CDCl$_3$) δ20.34, 20.81, 49.17, 87.07, 169.42. Anal. Calcd for $C_6H_{13}N_3O_4$: C, 37.69; H, 6.85; N, 21.98. Found: C, 37.77; H, 6.98; N, 21.82.

Example 2

Kinetic Studies of Compounds of Present Disclosure

This example illustrates kinetic studies of AcOM-IPA/NO (2) prepared in Example 1 in accordance with an embodiment of the invention.

The rate constants of decomposition were measured spectrophotometrically by monitoring the decrease in absorbance of peaks at ~240-250 nm characteristic of the diazeniumdiolate functionality. The hydrolysis medium consisted of the metal chelator diethylenetriaminepentaacetic acid (DTPA, 50 μM) in calcium- and magnesium-free Dulbecco's phosphate-buffered saline (PBS, pH 7.4). UV-visible spectroscopy was performed with a Hewlett-Packard 8453 diode-array spectrophotometer equipped with Agilent 89090A thermostat set to 37° C. The spectrophotometer was blanked after warming the cuvette containing buffer at the appropriate pH in the instrument heat block for 5 min. For esterase-containing reactions, porcine liver esterase (20 μL; Sigma; suspension in 3.2 M $(NH_4)_2SO_4$, pH 8) was added to the reaction buffer before blanking. Upon addition of IPA/NO (1) or AcOM-IPA/NO (2) (≤10 μL of stock), the cuvette was capped and inverted to mix. Spectra were collected at 0.5- to 60-s intervals for time periods of 2-120 min or until $A_\infty$<0.05. Kinetic analysis was performed by fitting the data to an exponential decay ($A=\Delta Ae^{-kt}+A_\infty$) using KaleidaGraph v.3.1.

Example 3

Reductive Nitrosylation of Metmyoglobin by Compounds of Present Disclosure

This example illustrates reductive nitrosylation of metmyoglobin by AcOM-IPA/NO (2) prepared in Example 1 in accordance with an embodiment of the invention.

To determine whether the products of hydrolyzing 2 include HNO, a method of trapping it with metmyoglobin (metMb) according to Equation 1 was established. This reductive nitrosylation reaction was followed spectrophotometrically by monitoring the decrease in metMb absorbance at 502 nm and the simultaneous increases in the peaks at 543 and 575 nm for MbNO.

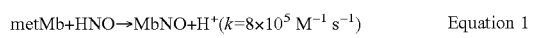

$$\text{metMb} + \text{HNO} \rightarrow \text{MbNO} + \text{H}^+ \quad (k=8\times10^5 \text{ M}^{-1} \text{ s}^{-1}) \qquad \text{Equation 1}$$

Reductive nitrosylation of ferric myoglobin (metMb) to nitrosyl myoglobin (MbNO) by 1 or 2 was monitored in a quartz cuvette in assay buffer at 37° C. Formation of HNO was further examined by quenching with GSH, which does not interact directly with low concentrations of NO. To maintain deaerated conditions, all solutions were transferred using gas-tight Hamilton syringes, and the reaction buffer was sparged with ultra-high purity argon at the rate of 1 min for each mL of buffer. Aliquots (2-3 mL) were removed by Hamilton syringe and transferred to an argon-flushed, graded seal quartz cuvette (Spectrocell; Oreland, Pa.) stoppered with a Suba-Seal septum (Sigma-Aldrich). The buffer within the cuvette was again gently bubbled with argon for 5 min. In a separate stoppered vial, a small amount of horse heart myoglobin was purged with argon for 15 min while in an ice bath and then dissolved with deaerated buffer. An aliquot of metMb (>1 mM stock; $A_{502}$=10.2 mM$^{-1}$ cm$^{-1}$) was added by syringe, as were aliquots of GSH (approximately 100×; 250 μM final) as appropriate. The reaction was initiated by introducing a small volume of stock diazeniumdiolate solution (1 in 10 mM NaOH, 2 in methanol, kept on ice; 100 μM final) to the metMb (50 μM final) solution. Spectra were collected at 30- to 60-s intervals for 60-90 min or until $A_{543}$ and $A_{575}$ reaches stable values. The concentration of MbNO was determined spectrophotometrically ($A_{543}$=11.6 mM$^{-1}$ cm$^{-1}$; $A_{575}$=10.5 mM$^{-1}$ cm$^{-1}$ (Antonini and Brunori, Frontiers Biol, 21, 19 (1971)); or in case of incomplete conversion $A_{575}$=5.2 mM$^{-1}$ cm$^{-1}$; $A_{575}$=6.7 mM$^{-1}$ cm$^{-1}$).

Figure 1B:
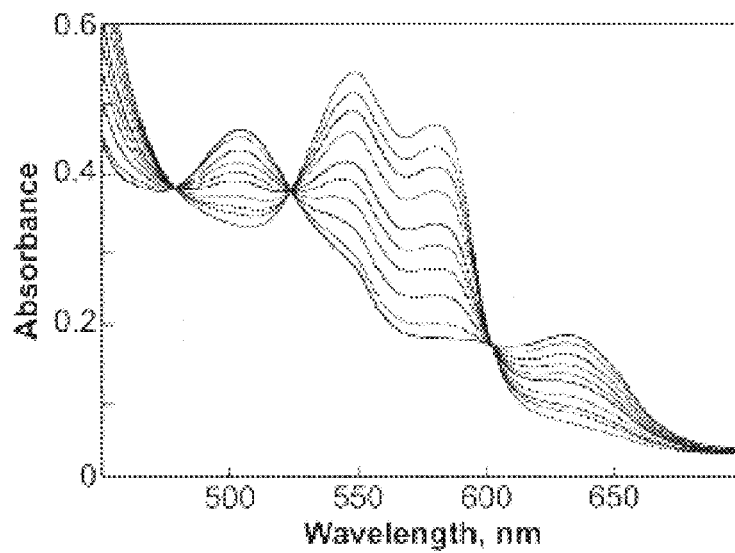

As shown in FIGS. 1A and 1B, both 1 (FIG. 1A) and 2 (FIG. 1B) at 100 μM concentration converted 50 μM metMb to MbNO, but 2 did so more efficiently, the yields being approximately 25 μM and 47 μM out of a possible 50 μM, respectively.

Figure 2A:
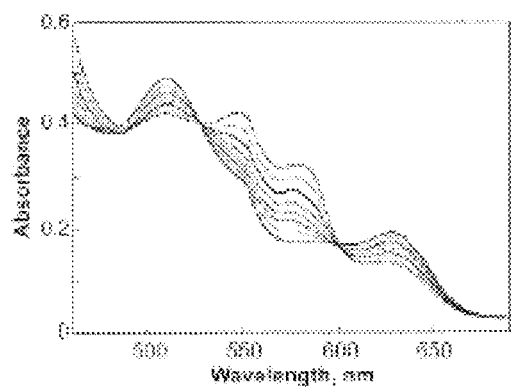
FIGS. 2A-D are graphs illustrating the effect of glutathione (GSH) on the reductive nitrosylation of metMb (50 µM) by (FIG. 2A) 1 (100 µM), (FIG. 2B) 2 (100 µM), (FIG. 2C) DEA/NO (50 µM), or (FIG. 2D) Angeli's salt (100 µM). The assay was performed in PBS (pH 7.4) containing 50 µM DTPA and 250 µM GSH at 37° C. under deaerated conditions over 1 h at 30-s cycles for 1 and 1.8 h at 30-s intervals for 2. Scans were plotted in FIG. 2A at 2, 4, 6, 9, 14, 23 and 56 min for 1. Scans were plotted in FIG. 2B at 0.5 and 60 min for 2. Scans were plotted in FIG. 2C at 1-min intervals to 8 min and then at 11, 14, 18, 23, 28 and 40 min. Scans were plotted in FIG. 2D at 500 s, when the decomposition of Angeli's salt was complete, and at 60 min, respectively.
Figure 2B:
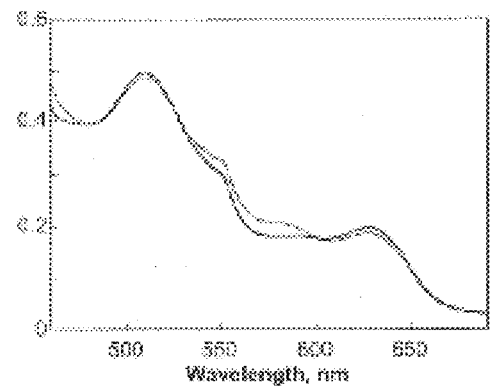
Figure 2C:
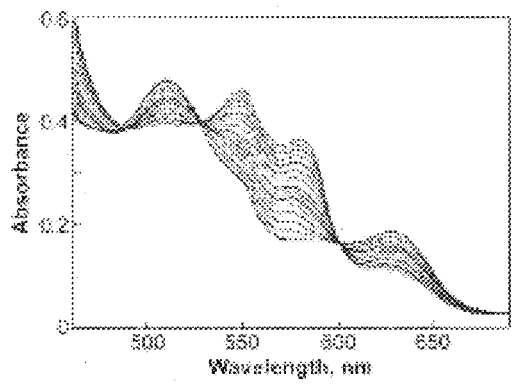
Figure 2D:
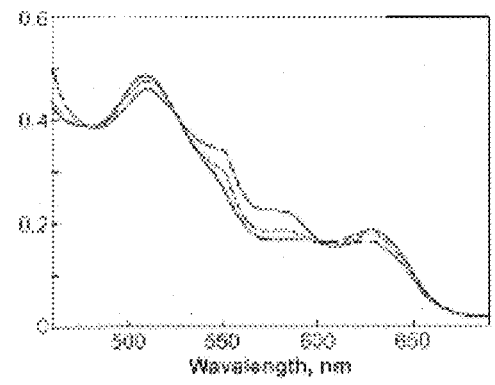

To confirm the production of nitroxyl in the spontaneous hydrolysis of 2, the reactions described above were repeated but in the presence of excess glutathione (GSH). GSH reacts 10-fold more rapidly than metMb with HNO but does not interact appreciably with low concentrations of NO. As seen in FIG. 2B, under deaerated conditions GSH inhibited reductive nitrosylation by 2 as expected based on the respective rate constants. Interestingly, GSH enhanced the formation of MbNO during the hydrolysis of 1 under these conditions (FIG. 2A). It was speculated that this was because 1 hydrolyzes to produce both HNO and NO. In deaerated solution, the NO coordinated weakly with metMb to form metMbNO, which was then reduced by GSH to MbNO (Reichenbach et al, *Nitric Oxide*, 5, 395-401 (2001)). FIG. 2A shows spectral changes comparable to those observed when the "pure" NO donor DEA/NO is hydrolyzed in the presence of both metMb and GSH (FIG. 2C). In contrast, the reaction of 2 with metMb in the presence of GSH was similar to that of the "pure" HNO donor Angeli's salt (FIG. 2D), confirming that 2 is similar to Angeli's salt in its HNO-generating ability.

Example 4

Analysis of Products Formed During Hydrolysis of Compounds of Present Disclosure This example illustrates the analysis of products formed during hydrolysis of $O^2$-(acetoxymethyl) 1-(isopropylamino)diazen-1-ium-1,2-diolate (AcOM-IPA/NO) (2) in accordance with an embodiment of the invention.

In addition to HNO measurements as described above by reductive nitrosylation of metmyoglobin, NO was quantified by chemiluminescence assay, $N_2O$ by gas chromatography, and nitrite ion by the Griess assay.

Organic products of the hydrolysis of 1 and 2 were quantified by integrating their NMR spectra. For pH 7.4, 3.9 mM solutions in 0.1 M phosphate buffer were employed. For pH 11, 4.9 mM solutions of 1 and 2 in 50 mM sodium carbonate were studied. Samples were run on a Varian Inova 400 MHz NMR with a Dell Precision 390 workstation. The samples were run at 37° C. and water suppression was achieved by using the preset pulse sequence. Peaks were identified by comparison with authentic standards.

Authentic propene was produced as a reference for the identification of this gas as a product of the reactions by the following procedure. Isopropylamino methyl carbamate was dissolved in dichloromethane and extracted with an equivalent volume of 1 M hydrochloric acid. A solution of sodium nitrite in water was added gradually. The bottom yellow-green layer as separated, dried over sodium sulfate, and concentrated under vacuum. A portion of the resulting oil (~5 μL) was dissolved in 10% sodium deuteroxide in $D_2O$ and allowed to decompose for 1 h. The NMR spectrum exhibited signals corresponding to methanol, isopropanol, starting carbamate, and a small (presumably saturating) concentration of propene. Its methyl group signals appeared as a doublet of triplets (δ1.70 and 1.72, J=1.5 and 6.5 Hz) identical to those observed in the hydrolysis of 1 and 2.

Compound 1 produced both NO and HNO on spontaneous hydrolysis at neutral pH. Surprisingly, the total amount of NO detected on hydrolyzing 2, a compound of formula (I), under the same conditions while purging gases formed in the reaction into an NO-specific chemiluminescence detector, was less than 1% of theoretical yield.

Figure 3A:
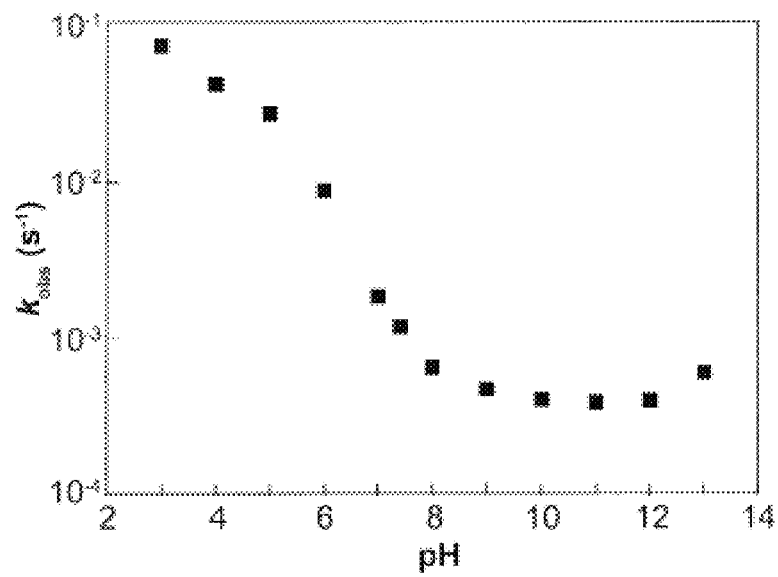
FIGS. 3A and 3B are graphs illustrating the pH-dependence of the rate constant of decomposition of (FIG. 3A) 1 (100 or 200 µM) and (FIG. 3B) 2 (100 µM) at 37° C. in PBS containing 50 µM DTPA measured at 250 nm (mean±SEM, n≥3).
Figure 3B:
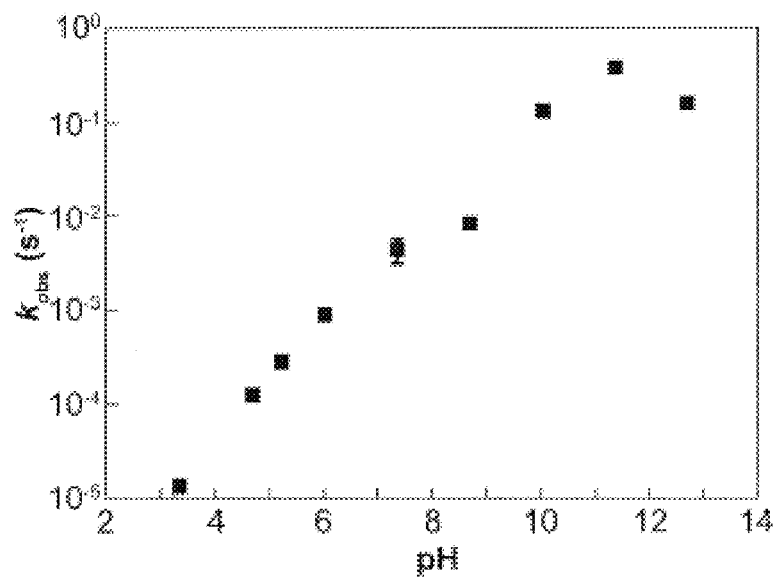

To gain insight into the mechanistic origins of this unexpected finding, the pH/rate profiles of the diazeniumdiolates 1 and 2 were explored. As previously established and shown in FIG. 3A, hydrolysis of 1 slowed as the pH was increased from 3 to 10, with a small increase in rate thereafter. This was the opposite of the results with 2, whose hydrolysis rate was essentially first order in hydroxide ion concentration between pH 5 and 11 (FIG. 3B).

Figure 4A:
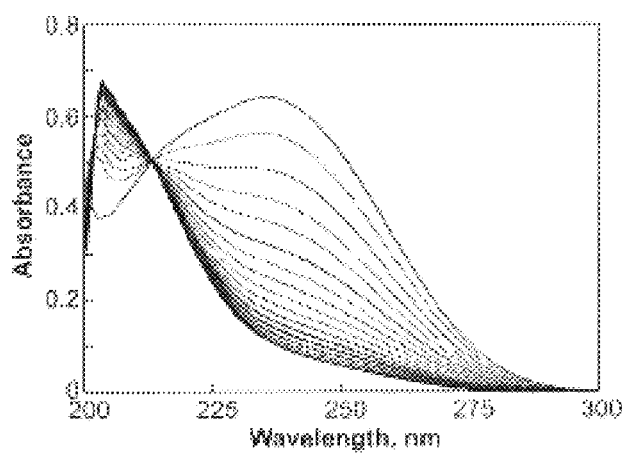
FIGS. 4A-C are graphs illustrating spontaneous hydrolysis (FIGS. 4A and 4B) and esterase-catalyzed hydrolysis (FIG. 4C) of 2 in an embodiment of the invention.
Figure 4B:
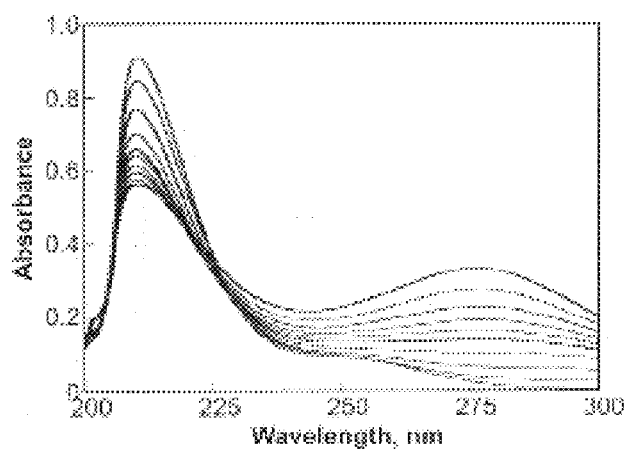

At and above pH 8, the rate of decomposition of 2 exceeds that of 1 (FIG. 3B versus FIG. 3A), indicating a mechanism involving more than simple hydrolysis of 2 to 1. Correspondingly, ultraviolet absorbance at 250 nm due to 1 was not observed in the spontaneous hydrolysis of 2 at pH 7.4 (FIG. 4A). Of further importance, there was a shift in ultraviolet maximum for 2 from $\lambda_{max}$ 236 nm to $\lambda_{max}$ 278 nm as the pH is raised to 12. This result is consistent with ionization of the NH bond (FIG. 4B).

Figure 4C:
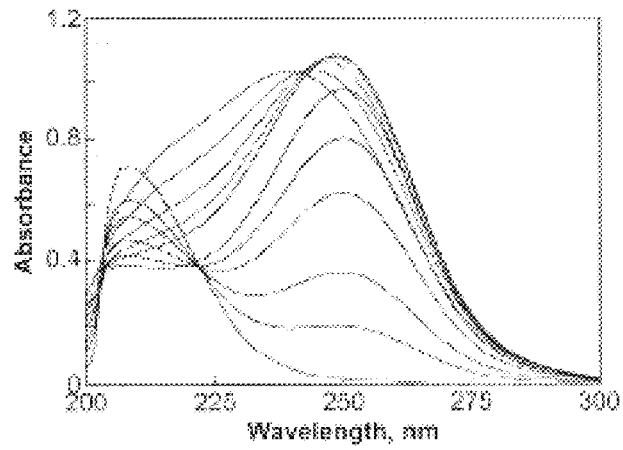

In contrast to simple buffer solutions, 1 is an observable intermediate in the hydrolysis of 2 when active esterase is present. As shown in FIG. 4C, the 250-nm peak for 1 dominated the spectrum within a short time after adding the enzyme to 2 in 0.1 M phosphate at pH 7.4. Additional studies confirmed that the esterase did not affect the stability of 1 or the ability of metMb and GSH to trap the hydrolytically produced HNO.

Consistent with the HNO/NO yield data, complete dissociation of 1 in pH 7.4 buffer showed it to generate similar amounts of isopropylamine and isopropanol, with essentially saturating concentrations of propene also being seen by NMR. In contrast, methyl peaks attributable to the amine border on undetectable in NMR spectra when 2 was hydrolyzed.

Differences in time course as well as stoichiometry in the alkaline hydrolysis of 1 and 2 also matched the expectation based on the HNO/NO yield and rate data. Ionic 1 hydrolyzed slowly at pH 11, and isopropylamine was not detected among the products, which is consistent with the spectral findings described above. Compound 2, on the other hand, completely dissociated within 5 min at 37° C. in a pH 11 carbonate buffer. Peaks for formaldehyde and acetate ion were seen in addition to those for the carbocation-derived alcohol and alkene. However, the amine was undetectable.

Without wishing to be bound by any theory, one way to rationalize the absence of free 1 as a hydrolysis product is that base-induced removal of the N—H proton of 2 generated intermediate ion 3', which might be expected to undergo 1-4 acyl migration via cyclic intermediate 4' as shown in the following scheme. Expulsion of formaldehyde from 4' could give 5', which could then fragment with N—N bond cleavage to produce diazoate ion 6' and acylnitroso derivative 7'. Aliphatic diazoates are known progenitors of "hot" carbenium ions that can indiscriminately alkylate ambient nucleophiles (such as water to produce the corresponding alcohol) with cogeneration of an equivalent of dinitrogen, and acylnitroso compounds such as 7' are known to hydrolyze to HNO with the derived carboxylate as by-product.

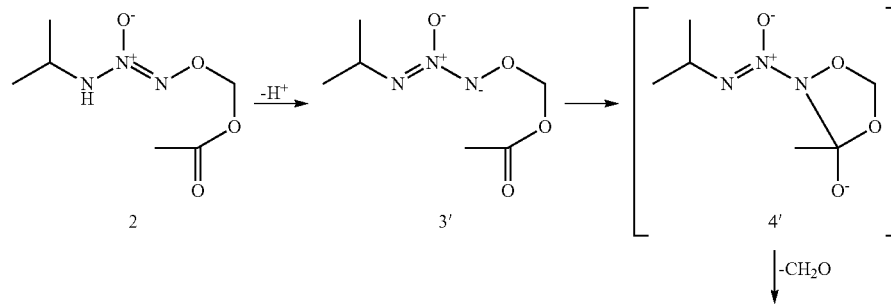

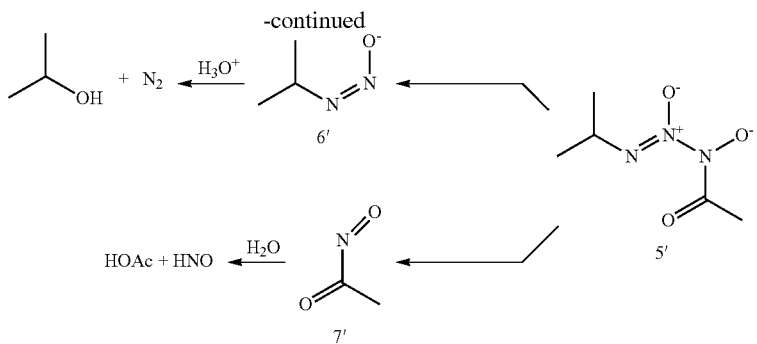

Example 5

Method of Synthesis of an Embodiment of Formula (I)

This example demonstrates a method of synthesis of an embodiment of formula (I) wherein R4 is an NSAID moiety: O2-(Acetylsalicyloyloxymethyl)-1-(N-isopropylamino)-diazen-1-ium-1,2-diolate (IPA/NO-Aspirin; Compound 4). This example also demonstrates a method of synthesis of O2-(Acetylsalicyloyloxymethyl)-1-(N,N-Diethylamino)-diazen-1-ium-1,2-diolate (DEA/NO-Aspirin; Compound 8). IPA/NO-Aspirin 4 and DEA/NO-Aspirin 8 were synthesized via the following Scheme.

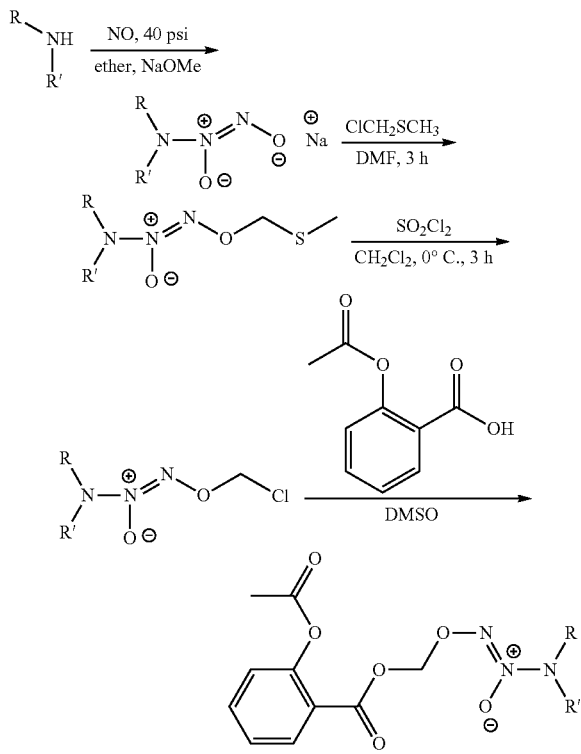

DEA/NO-Aspirin: R = R' = Et
IPA/NO-Aspirin: R = isopropyl; R' = H

$O^2$-Sodium 1-(N-Isopropylamino)diazen-1-ium-1,2-diolate (1)

This compound was synthesized as described previously, Drago et al. and Margo et al. both supra $^1$H NMR (500 MHz, CDCl$_3$): δ 0.98 (d, J=6.5 Hz, 6H, CH$_3$), 4.06 (m, J=6.5 Hz, 1H, CH), 6.067 (s, 1H, NH). $^{13}$C NMR (500 MHz, CDCl$_3$): δ 21.343 (CH$_3$), 47.691 (CH).

$O^2$-(Methylthiomethyl)-1-(N-Isopropylamino)diazen-1-ium-1,2-diolate

Chloromethyl methyl sulfide (1.93 mL, 23.38 mmol) was added to a slurry solution of Na$_2$CO$_3$ (1.24 g, 11.69 mmol) in DMF (50 mL) at room temperature. Reaction mixture was stirred for 2 min before sodium salt of IPA/NO (3.297 g, 23.38 mmol) was added and stirring was continued for 3 h. Reaction mixture was quenched by addition of ethyl acetate (70 mL), which was then filtered and subsequently washed with 10% NaCl solution (5×40 mL). The organic layer was then dried over sodium sulfate and evaporated to obtain the crude product, which was further purified on flash column (20:80:EA:Hexane) to obtain (780 mg, 18.6%) of light yellow oil. 1H NMR (400 MHz, CDCl$_3$): δ 1.22 (d, J=6.5 Hz, 6H, CH$_3$), 4.06 (dq, J=6.5, 15.6 Hz, 1H, CH), 6.05 (d, J=9.1 Hz, 1H, NH), 5.24 (s, 2H, CH$_2$), 2.28 (s, 3H, CH$_3$). $^{13}$C NMR (500 MHz, CDCl$_3$): δ14.7 (SCH$_3$), δ19.96-20.006 (CH$_3$), δ48.789 (CH), δ78 (CH$_2$SCH$_3$). IR (NaCl): 3286, 3014, 2964, 1580, 1414, 1308, 1018, 976 (isopropyl amine portion and CH$_3$SCH$_2$ portion), 1170, 1133 (N=N—O). UV: ε($\lambda_{213\ nm}$)=54.2 mM$^{-1}$ cm$^{-1}$, ($\lambda_{246\ nm}$)=7.24 mM$^{-1}$ cm$^{-1}$.

$O^2$-(Chloromethyl)-1-(N-Isopropylamino)diazen-1-ium-1,2-diolate

A solution of (O$^2$-(methylthiomethyl)-1-(N-isopropylamino)diazen-1-ium-1,2-diolate) (0.76 g, 4.25 mmol) dissolved in dichloromethane (17 mL) was cooled to −78° C. Then sulfuryl chloride (5 mL of 1.0 M solution in CH$_2$Cl$_2$, 4.67 mmol) was added drop-wise with stirring at 4° C. and the completion of the reaction was monitored by TLC. After 2 h, the reaction mixture was filtered and evaporated to yield yellow oil which was then used immediately for the next step without further purification. $^1$H NMR (500 MHz, CDCl$_3$): δ1.22 (d, J=6.5 Hz, 6H, CH$_3$), 4.02 (m, J=6.5 Hz, 1H, CH), 6.23 (s, 1H, NH), 5.8 (s, 2H, CH$_2$). $^{13}$C NMR (500 MHz, CDCl$_3$): δ20.393 (CH$_3$), 649.373 (CH), 679.254 (CH$_2$Cl).

$O^2$-(Acetylsalicyloyloxymethyl)-1-(N-isopropylamino)-diazen-1-ium-1,2-diolate Aspirin (765 mg, 4.25 mmol) was dissolved in DMSO (2 mL). Triethylamine (0.6 mL, 4.25 mmol) was then added and the reaction mixture was stirred for 50 min at room temperature. Then a solution of $O^2$-(chloromethyl)-1-(N-isopropylamino)diazen-1-ium-1,2-diolate in DMSO (2 mL) was added drop wise to the reaction mixture. The reaction mixture was stirred for 15 h and after completion of the reaction; it was quenched with ethyl acetate (40 mL). The organic layer was washed with saturated NaHCO$_3$ solution (5×40 mL), dried over sodium sulfate and then evaporated to obtain the crude product. Further purification was performed by column chromatography (22% Ethyl Acetate: Hexane) to obtain IPA/NO-aspirin (460 mg, 37.8%) as viscous white oil. $^1$H NMR (500 MHz, CDCl$_3$): δ1.16 [d, J=6.5 Hz, 6H, (CH3)2], 2.33 (s, 3H, COCH3), 3.98 (dq, J=6.5, 15.6 Hz, 1H, CH), 5.94 (s, 2H, OCH2O), 6.16 (d, J=9.25 Hz, 1H, NH), 7.1 (dd, J=8 Hz, 1 Hz, phenyl H-3), 7.3 (td, J=3 Hz, 1 Hz, phenyl H-5), 7.6 (td, J=3.5 Hz, 1.5 Hz, phenyl H-4), 8.04 (dd, J=8 Hz, 1.5 Hz, phenyl H-6). $^{13}$C NMR (500 MHz, CDCl$_3$): δ20.872 (COCH3), 21.4 [(CH3)$_2$], 49.65 (CH), 88.164 (CH2), 122.59 (aromatic Cl), 124.34 (aromatic C3), 126.5 (aromatic C5), 132.5 (aromatic C6), 135.01 (aromatic C4), 151.479 (aromatic C2), 163.177 (C=O), 170.04 (OC=OCH3). IR: 3286, 3014 (C—H aromatic), 2923 (C—H aliphatic), 1739 (CO2), 1602 (CO2), 1247, 1190 (N=N—O) cm$^{-1}$. Elemental analysis (Cl3H17N3O6): C=50.16; H=5.50; N=13.50 (theoretical), C=49.92; H=5.42; N=13.42 (experimental), MS (LCQ, ESI ionization method): 334.1 (MNa$^+$ peak), UV: ε($\lambda_{240\ nm}$)= 7.87 mM$^{-1}$ cm$^{-1}$.

$O^2$-Sodium 1-(N,N-Diethylamino)diazen-1-ium-1,2-diolate

Diethylamine (10 mL, 0.05 mol) and sodium methoxide in methanol (12 mL in 25% methanol, 0.05 mol) was added to diethyl ether (150 mL) at room temperature. This reaction mixture was then flushed with argon for 10 min and then exposed to nitric oxide (40 psi) for 24 h. The solid precipitate formed was filtered and washed with diethyl ether to obtain $O^2$-Sodium 1-(N,N-Diethylamino)diazen-1-ium-1,2-diolate (7.2 g, 0.046 mol, 92.9%) as white solid. $^1$H NMR (500 MHz, CDCl$_3$): δ0.95 [t, J=7.0 Hz, 6H, (CH$_3$)$_2$], 2.9 (q, 4H, CH$_2$). $^{13}$C NMR (500 MHz, CDCl$_3$):

$O^2$-(Methylthiomethyl)-1-(N,N-Diethylamino)diazen-1-ium-1,2-diolate

To a mixture of sodium carbonate (2.391 g, 22.56 mmol) and DMF (50 mL) was added chloromethyl methyl sulfide (1.862 mL, 22.56 mmol) and the reaction mixture was stirred at room temperature for 5 min. Then DEA/NO (3.5 g, 22.56 mmol) was added to the reaction mixture and stirring was continued for 3 h. The reaction mixture was quenched by addition of 70 mL ethyl acetate and filtered. The organic layer was washed with 10% NaCl solution (5×40 mL), dried over sodium sulfate and evaporated to obtain the crude product, which was further purified by silica gel column chromatography (20:80=EA: Hexane) to give (2.6 g, 59.6%, Rf=0.48) a light yellow oil. $^1$H NMR (500 MHz, CDCl$_3$): δ1.09 (t, J=7 Hz, 6H, CH$_3$), 2.21 (s, 3H, SCH$_3$), 3.1 (q, J=7 Hz, CH$_2$), 5.274 (s, 2H, CH$_2$). $^{13}$C NMR (500 MHz, CDCl$_3$): δ11.477 [(CH$_3$)$_2$], 15.118 (CH$_3$), 48.465 [(CH$_2$)$_2$], 78.322 (OCH$_2$S).

$O^2$-(Chloromethyl)-1-(N,N-Diethylamino)diazen-1-ium-1,2-diolate

O-methylthiomethyl DEA/NO (2.1 g, 10.87 mmol) dissolved in DCM (120 mL) and the reaction mixture was cooled to 0° C. Sulfuryl chloride (0.883 mL, 10.87 mmol) was then added slowly to the reaction mixture using a dropping funnel. The completion of the reaction mixture was monitored by TLC. The reaction mixture was filtered and evaporated, which was then used for next step without further purification. $^1$H NMR (500 MHz, CD$_3$CN): δ1.1 (t, J=7 Hz, 6H, CH$_3$), 3.3 (q, J=7 Hz, 4H, CH$_2$), 5.97 (s, 2H, CH$_2$). $^{13}$C NMR (500 MHz, CD$_3$CN): δ11.676 (CH$_3$), 48.522 (CH$_2$), 80.946 (CH$_2$Cl).

$O^2$-(Acetylsalicyloyloxymethyl)-1-(N,N-Diethylamino)-diazen-1-ium-1,2-diolate

To a solution of O-acetylsalicylic acid (1.865 g, 10.35 mmol) in DMSO (20 mL), triethylamine (1.455 ml, 10.35 mmol) was added and the reaction mixture was stirred for 30 min at room temperature. O-Chloromethyl DEANO (1.880 g, 10.35 mmol) was then dissolved in DMSO (20 mL) and added to the reaction mixture drop-wise. After 8 h, the reaction was quenched with ethyl acetate (70 mL). The organic layer was washed with 10% NaCl solution 5 times and evaporated to get the crude product. The crude product was purified using column chromatography (30% ethyl acetate-hexane) to obtain 2.2 g (65.1%) of pure product. $^1$H NMR (500 MHz, CDCl$_3$): δ1.08 [t, J=4.5 Hz, 6H, (CH$_3$)$_2$], 2.33 (s, 3H, COCH3), 3.2 (q, J=7 Hz, 4H, CH$_2$), 5.995 (s, 2H, OCH2O), 7.09 (dd, J=1, 8 Hz, phenyl H-3), 7.3 (td, J=1, 7.5 Hz, phenyl H-5), 7.6 (td, J=1, 8 Hz, phenyl H-4), 8.03 (dd, J=1, 8 Hz, phenyl H-6). $^{13}$C NMR (500 MHz, CDCl$_3$): δ11.45 [(CH$_3$)$_2$], 20.994 (COCH3), 48.002 [(CH$_2$)$_2$], 87.905 (CH$_2$), 122.076 (aromatic C1), 123.985 (aromatic C3), 126.0 (aromatic C5), 131.597 (aromatic C6), 134.521 (aromatic C4), 151.119 (aromatic C2), 162.528 (C=O), 169.556 (OC=OCH3). Elemental analysis (Cl3H17N3O6): C=51.69; H=5.89; N=12.92 (theoretical), C=51.49; H=5.13; N=12.73 (experimental), MS (LCQ, ESI ionization method): 348.1 (MNa$^+$ peak).

Example 6

Kinetic Profile of NO and HNO Release from HNO-Releasing Aspirin (IPA/NO-Aspirin) and NO-Releasing Aspirin (DEA/NO-Aspirin)

This example demonstrates the kinetic profile of NO and HNO release from HNO-releasing aspirin (IPA/NO-aspirin) and NO-releasing aspirin (DEA/NO-aspirin).

The newly synthesized HNO-releasing aspirin (IPA/NO-aspirin, 4) and NO-releasing aspirin (DEA/NO-aspirin, 8) were evaluated for the kinetic profile of NO and HNO release in buffer and cells. Both NSAID modified compounds (4 and 8) were found to be relatively stable in phosphate buffer pH 7.4 for several hours.

Example 7

Release of HNO and NO from HNO-Releasing Aspirin (IPA/NO-Aspirin) and NO-Releasing Aspirin (DEA/NO-Aspirin)

This example demonstrates the release of HNO and NO from HNO-releasing aspirin (IPA/NO-aspirin) and NO-releasing aspirin (DEA/NO-aspirin).

The release of NO was evaluated using an NO specific electrode. The NO electrode was stabilized in phosphate buffer pH 7.4 containing 2% serum. Compounds 4 and 8 in DMSO were added and the NO signal was measured. The experiment was repeated in the presence of 1 mM sodium ferricyanide.

100 μM of compound 8 readily released NO in the presence of 2% serum while 100 μM of compound 4 showed significantly lower NO production. Since there is no direct method for detection of HNO, 1 mM ferricyanide solution was used, which converts HNO to NO that can then be detected using NO electrode.

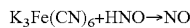

$$K_3Fe(CN)_6 + HNO \rightarrow NO$$

In spite of the faster decomposition kinetics of compound 4, the amount of NO detected is half of compound 8. This is due to self consumption of HNO due to dimerization ($k = 8 \times 10^6 M^{-1} s^{-1}$) and reaction of HNO with NO ($k = 6 \times 10^6 M^{-1} s^{-1}$) (Shafirovich et al., PNAS 99: 7340-7345 (2002)) (Table 1).

TABLE 1

|  | [NO]pA |
|---|---|
| IPA/NO-Aspirin | 1000 |
| IPA/NO-Aspirin (+Ferricyanide) | 2100 |
| DEA/NO-Aspirin | 4600 |
| DEA/NO-Aspirin (+Ferricyanide) | 5000 |

The reaction of metmyoglobin (metMb) with HNO was used for detection of HNO. 4 on reaction with metMb in the presence of 2% guinea pig serum under physiological conditions underwent reductive nitrosylation, thereby indicating production of HNO. The release profile from both 4 and 8 was also studied using oxymyoglobin (oxyMb), which reacts with both NO and HNO. HNO production from 4 was further verified by reaction of oxyMb with 4 in the presence of 1 mM glutathione (GSH), a HNO scavenger.

Detection of HNO was also carried out using the chemiluminescence method in, 1 mM ferricyanide solution. Again 4 showed both NO and HNO release while 8 shows NO release.

Example 8

Exemplary Cell Culture Methods

For examples utilizing cell culture methods, the following procedure was instituted. Human breast adenocarcinoma cells (MDA-MB-231, MCF-7 and MDA-MB-468; American Type Culture Collection, Manassas, Va.) were grown as monolayers in RPMI 1640 (Invitrogen, Carlsbad, Calif.) supplemented with 10% FBS (Hyclone, Thermo Fisher Scientific Inc., Waltham, Mass.), penicillin (50 units $mL^{-1}$) and streptomycin (50 mg $mL^{-1}$; Life Technologies, Inc., Grand Island, N.Y.). Non-tumorigenic, human breast epithelial cells (MCF-10A; American Type Culture Collection) and HUVECs (Cell Applications, Inc., San Diego, Calif.) were grown as monolayers in endothelial growth media (Lonza Inc., US-Allendale, N.J. or Cell Applications, Inc., San Diego, Calif.). Cells were seeded at a density of $1 \times 10^6$ cells per 100 $cm^2$ culture dish and were incubated at 37° C. in 5% $CO_2$ at 80% relative humidity. Single-cell suspensions were obtained by trypsinization (0.05% trypsin/EDTA, Invitrogen, Carlsbad, Calif.). MDA-MB-231 cells stably transfected with green fluorescent protein (GFP) and G418 antibiotic resistance gene were a generous gift from Dr. Aldona Karaczyn from the Maine Medical Center Research Institute, Scarborough, Me. MDA-MB-231-GFP cells were grown as described for MDA-MB-231 cells with the addition of 418 antibiotics (100 mg $mL^{-1}$) to ensure vector presence.

Example 9

Exemplary Mouse Tumor Model Methods

For examples utilizing mouse tumor model methods, the following procedure was instituted. Analysis of tumor growth was carried out using protocols approved by the Committee on the Ethics of Animal Experiments of the National Cancer Institute (RBB-144) and adhered with the recommendations in the United States National Research Council's "Guide for the Care and Use of Laboratory Animals," the United States Public Health Service's "Guide for the Care and Use of Laboratory Animals" and the "Policy on Humane Care and Use of Laboratory Animals". The vivarium was maintained at 23° C. on a 12 h light/12 h dark cycle with ad libitum access to food and water. Nude mice (n=40) under general anesthesia were implanted with $7.5 \times 10^5$ MDA-MB-231 cells transfected with GFP by injection underneath the fourth left mammary gland. Prior to implantation, pedal withdrawal and eyelid reflexes were examined to ensure that mice were under stage III of anesthesia. At 14 days post-inoculation, the mice were randomly divided into four groups and treated by daily injection of equimolar doses (10 μL of 100 mM stock) of aspirin (9.00 mg $kg^{-1}$), IPA/NO-aspirin (15.8 mg $kg^{-1}$) or DEA/NO-aspirin (16.3 mg $kg^{-1}$) or with vehicle (DMSO). After five weeks, the tumor size was measured using in vivo fluorescent imaging for quantification of the GFP tag. In brief, mice were under general anesthesia throughout the whole body imaging process, and GFP signals were captured and quantified in an Xenogen IVIS 100 Imaging System according to the manufacturer's protocol. To assess metastasis in the brain, the animals were subsequently sacrificed following the approved method and guidelines.

Example 10

Effects of Compound Embodiments in Cancer Models

Effect of NONO-Aspirin Prodrugs on Cell Viability

Figure 5A:
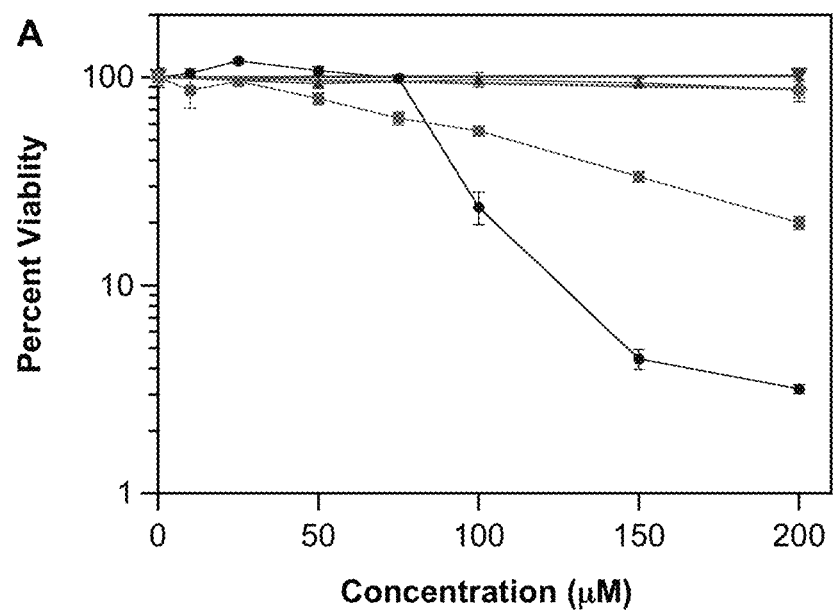
FIG. 5 shows the effect of NONO-aspirin prodrugs (10-200 µM), aspirin (50-200 µM) or parent diazeniumdiolates (200 µM) on the viability of A) MDA-MB-231, B) MDA-MB-468, C) MCF-7 or D) MCF-10A cells. Cells were treated for 48 h at 37° C., and cell survival was determined using the MTT (3-(4,5-dimethylthiazol-2-yl)-2,5-diphenyltetrazolium bromide) assay. Figures are representative of three trials with data plotted as mean percentage versus untreated cells±SD of the four replicates per plate). Vehicle (DMSO or 10 mM NaOH) was added as a control to otherwise untreated cells.
Figure 5B:
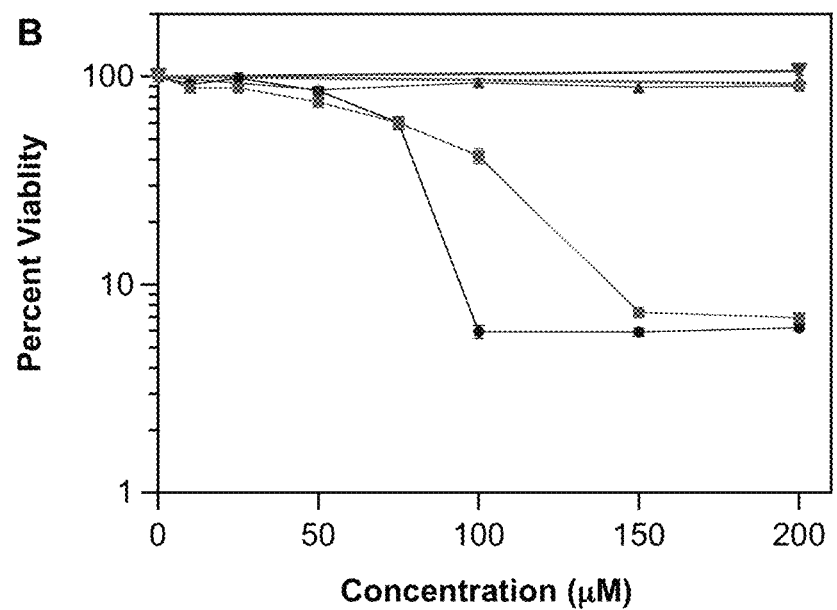
Figure 5C:
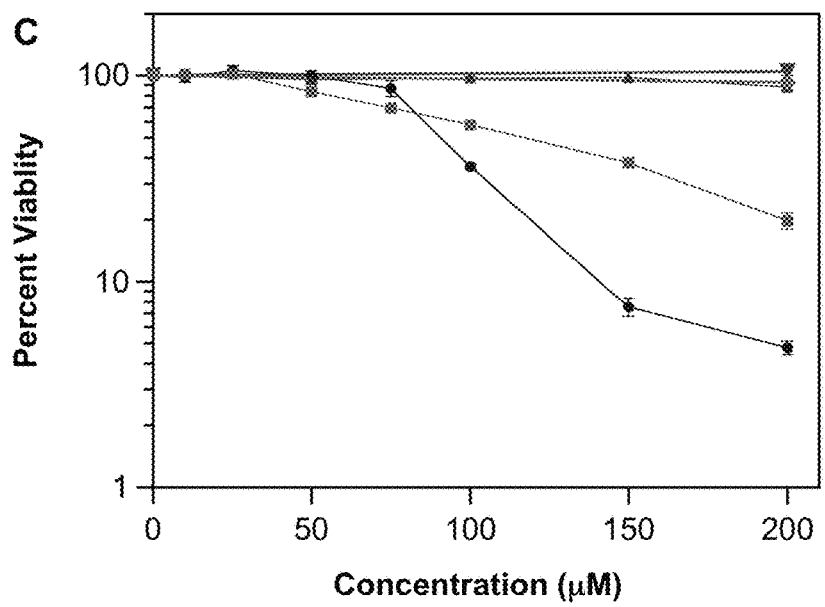

While the cytotoxicity of both aspirin and ionic diazeniumdiolates in various cancer cells lines is low ($IC_{50} > 1$ mM), NO-NSAIDs and related constructs significantly inhibit growth of cultured cancer cells as well as xenografts in mouse models. IPA/NO-aspirin and DEA/NO-aspirin have been shown to selectively reduce proliferation of lung carcinoma cells ($IC_{50}$ values of 100 μM) compared to normal endothelial cells. In this example, the impact of IPA/NO-aspirin and DEA/NO-aspirin was assessed compared to aspirin or the parent diazeniumdiolate on proliferation of four human breast cell lines: MDA-MB-231 (ER(−)) adenocarcinoma), MDA-MB-468 (ER(−) adenocarcinoma), MCF-7 (ER(+) adenocarcinoma) and MCF-10A (non-tumorigenic, immortalized human breast epithelial cells). NONO-aspirin prodrugs have been shown to be metabolized in cultured cells in less than 10 hours. After 48 hours, the reduction in viability by each prodrug was comparable in all three breast adenocarcinoma lines, regardless of sensitivity to estrogen (FIG. 5A-5C, Table 1), and was similar to that observed previously in lung carcinoma cells and by clonogenic assay.

TABLE 1

Values are mean ± SD for three trials, except for MCF-10A cells, which did not reach a 50% reduction at 200 µM.

| cell line | IPA/NO-aspirin | DEA/NO-aspirin |
|---|---|---|
| MDA-MB-231 | 92 ± 1 | 102 ± 10 |
| MDA-MB-468 | 81 ± 2 | 90 ± 4 |
| MCF-7 | 93 ± 2 | 122 ± 3 |
| MCF-10A | >200 | >200 |

Figure 5D:
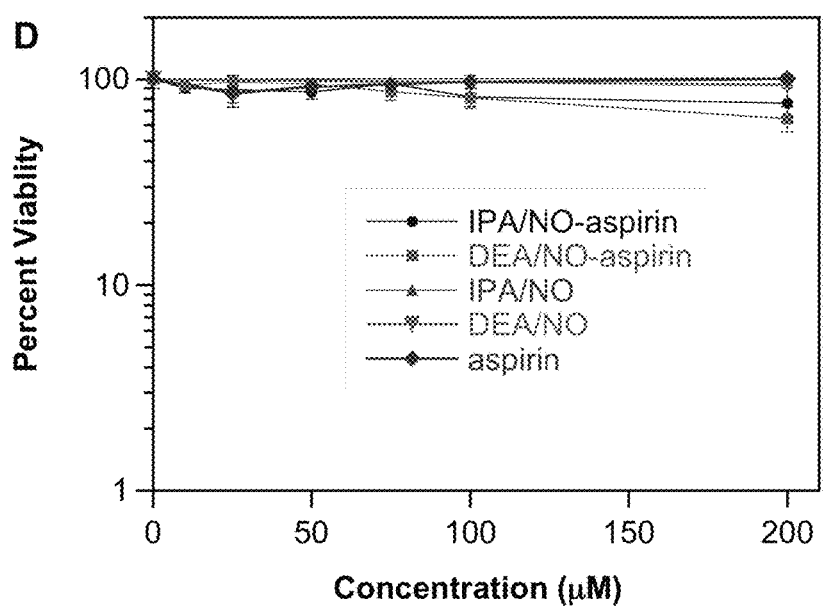

Cancer cells appear to generally be more sensitive to IPA/NO-aspirin compared to the NO-donating analogue. The lack of an effect on nonmalignant epithelial cells at up to 200 µM (FIG. 5D) supports a cancer-dependent response. The precursors did not impact viability at concentrations below 200 µM, suggesting that the prodrug itself may be involved or that concomitant delivery of NO or HNO may lead to chemosensitization.

Effect of NONO-Aspirin Prodrugs on Growth of MDA-MB-231 Xenografts

Figures 6A, 6B, 6C:
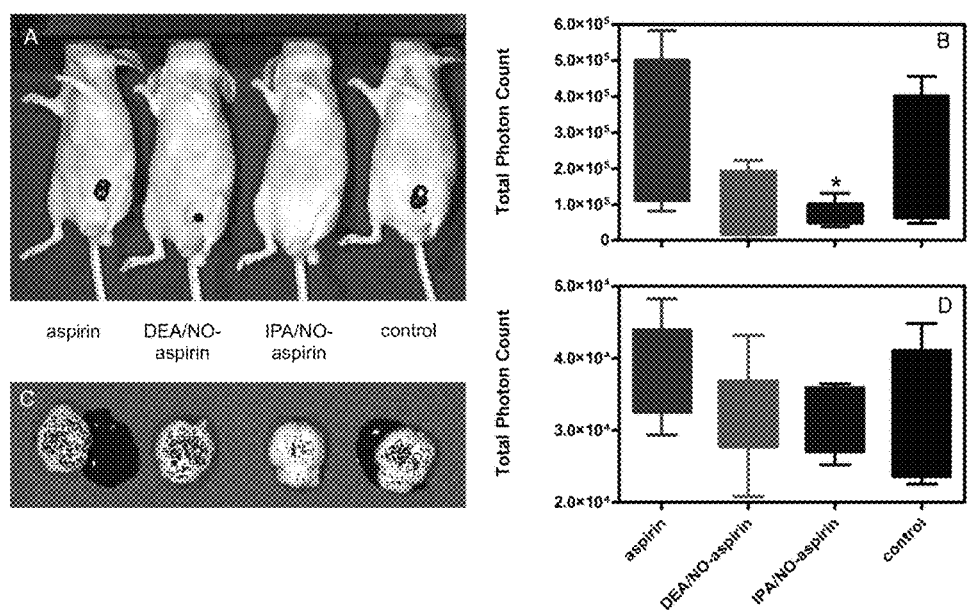
FIG. 6 shows the effect of NONO-aspirin prodrugs or aspirin in nude mice implanted with 7.5×10$^5$ MDA-MB-231 cells stably transfected with GFP. The cells were allowed to grow for 14 d, and the animals (40) were randomly divided into four groups (control, aspirin, IPA/NO-aspirin or DEA/NO-aspirin). Treated groups were injected daily with equimolar doses of DEA/NO-aspirin or IPA/NO-aspirin (16 mg kg$^{-1}$) or aspirin (9 mg kg$^{-1}$)) or with DMSO for the next five weeks. Tumor size was then measured using in vivo fluorescent imaging for quantification of the GFP tag: A) qualitative image of individual animals, B) quantitative analysis of fluorescence intensity at the primary tumor site, C) qualitative image of individual brains, D) quantitative analysis of fluorescence intensity due to metastasis to the brain. *p<0.001 vs. control.

In addition, the effects of the NONO-aspirin prodrugs on one of the ER(−) lines were evaluated due to the more aggressive nature of this type of breast cancer. The chemotherapeutic effect of IPA/NO-aspirin and DEA/NO-aspirin was investigated in xenografts of GFP-transfected MDA-MB-231 cells, which allow noninvasive monitoring of tumor size. At the conclusion of two weeks of tumor growth and five weeks of treatment, aspirin did not significantly decrease the size of the primary tumor compared to the control (FIG. 6A, 6B). A substantial, although not statistically significant, reduction in fluorescence intensity was observed for DEA/NO-aspirin. Although masses were visible, upon preliminary examination they appeared to be primarily fibrotic tissue. Treatment with IPA/NO-aspirin led to both a significant decrease in fluorescence intensity and tumor mass. This suggests that the HNO-donating derivative not only is effective at inhibiting tumor progression but also is tumoricidal.

Fukuto et al. previously performed a similar study on the impact of HNO on MDA-MB-231 xenograft growth in SCID mice. The HNO donor was Angeli's salt ($Na_2N_2O_3$), which is the most commonly used HNO donor in biological studies and is of the diazeniumdiolate class. Like IPA/NO, Angeli's salt decomposes spontaneously with a short half-life (~4 min) under physiological conditions. Treatment with Angeli's salt led to some inhibition of tumor growth at both 17 and 50 mg $kg^{-1}$ compared to control. This is consistent with the discovery that extracellular decomposition of ionic diazeniumdiolates is less effective than intracellular delivery by derivatized analogues.

Since MDA-MB-231 cells have a propensity to form metastatic tumors, the effect of the prodrugs was also studied on metastasis to the brain. While IPA/NO-aspirin and DEA/NO-aspirin both decreased metastasis compared to aspirin and untreated controls, the results were not statistically significant (FIG. 6C, 6D).

Since nitration of GFP is known to reduce fluorescence intensity, the impact of HNO and NO on the GFP signal in MDA-MB-231-GFP cells during 48 hours of growth was investigated to ensure that the reduction in signal in FIG. 6 was not due to a chemical modification or modulation of GFP transcription. Over this period, fluorescence intensity increased, suggesting that cells were proliferating, and fluorescence intensity was not significantly impacted by the presence of 50 µM IPA/NO or 75 µM DEA/NO compared to NaOH control. This indicates that the reduction in signal in FIG. 6 was a result of tumor regression as a function of exposure to the prodrugs.

Example 11

Methods of Inducing DNA Damage Using Compound Embodiments

Figures 7A, 7B, 7C, 7D:
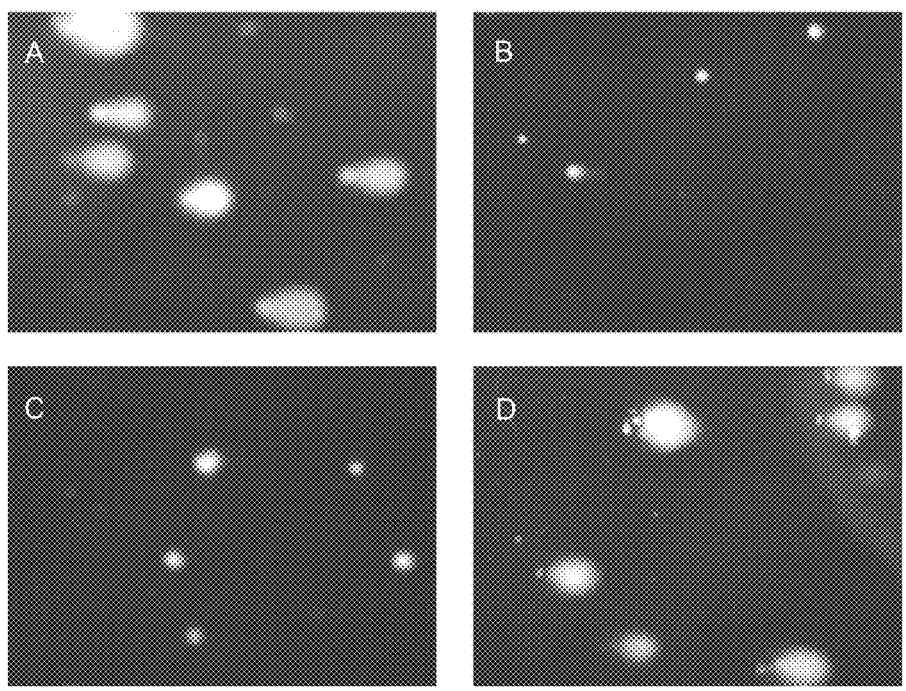
FIG. 7 shows the effect of the NONO-aspirin prodrugs on DNA damage in MDA-MB-231 cells as determined using the Comet assay after 8 h at 37° C.: A) 50 µM IPA/NO-aspirin, B) 75 µM DEA/NO-aspirin, C) 0.1% DMSO or D) 100 µM $H_2O_2$.
Figure 8:
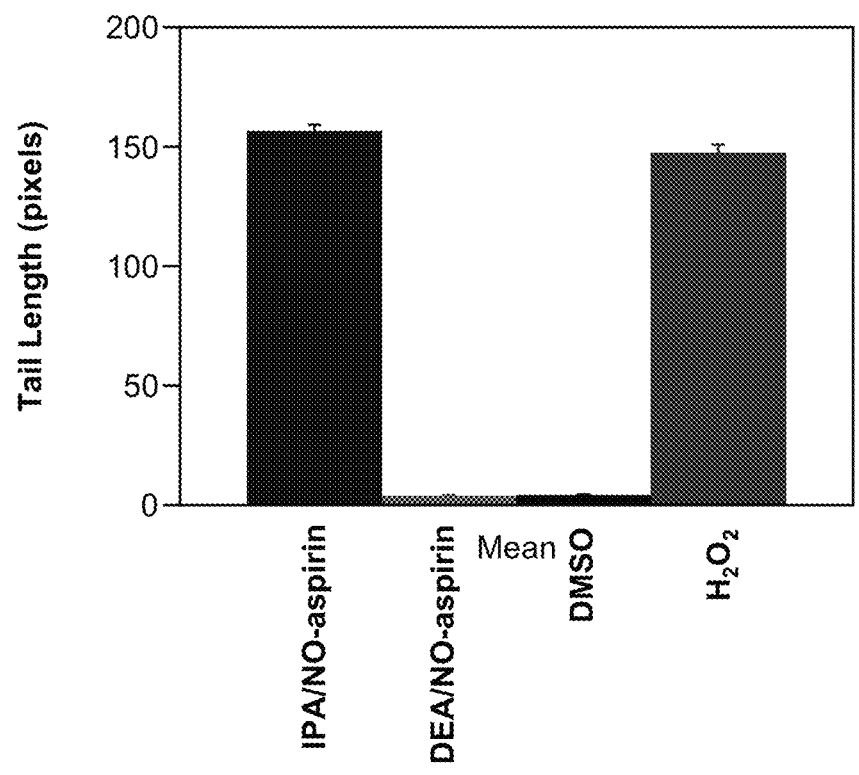
FIG. 8 shows the effect of the NONO-aspirin prodrugs on DNA damage in MDA-MB-231 cells as determined using the Comet assay after 8 h at 37° C.: 50 µM IPA/NO-aspirin, 75 µM DEA/NO-aspirin, 0.1% DMSO or 100 µM H2O2. Tail length: mean±SEM, n≥150.

Autoxidation of both NO and HNO leads to species that are capable of damaging DNA. Conversion of NO to $N_2O_3$ can induce mutations through base deamination) while the product of the reaction of HNO with $O_2$ can oxidize and cleave DNA. To investigate the possibility of RNS-induced DNA damage as a mechanism of cytotoxicity, the effect of the NONO-aspirin prodrugs was studied with the alkaline Comet assay in MDA-MB-231 cells. After 8 hours, the damage induced by treatment with 50 µM IPA/NO-aspirin was significant (FIG. 7A) and similar to the $H_2O_2$ positive control (FIG. 7C). Exposure instead to 75 µM DEA/NO-aspirin (FIG. 7B) did not differ from the DMSO-treated negative control (FIG. 7D). A quantitative comparison is shown in FIG. 8. These data are consistent with the DCF study that intracellular delivery of HNO can induce substantial oxidative modifications. This may be an important factor in the observed enhanced cytotoxicity of IPA/NO-aspirin. In particular, IPA/NO-aspirin is able to damage DNA (FIG. 7) including inducing double strand breaks, in a manner similar to radiation therapy and chemotherapies such as doxorubicin.

Example 12

Methods of Inducing Thiol Binding Using Compound Embodiments

This example examined the underlying mechanism for the observed cancer-dependent response and the higher sensitivity of cancer cells to the HNO-donating adduct. A first consideration when comparing the effects of HNO to those of NO is the known difference in biotargets. HNO primarily interacts with thiols and ferric complexes while NO readily associates with ferrous complexes and other free radicals. Both HNO and NO can target and post-translationally modify crucial cellular proteins, especially those containing thiols. Direct association of HNO with thiols leads to irreversible modification. NO does not directly interact with thiols, but reaction with reactive oxygen species (ROS) can lead to nitrosating species. The reaction of HNO or NO with $O_2$ forms more deleterious species, but the autoxidation product of HNO is more cytotoxic and is capable of cleaving double strand DNA.

In addition to interacting with specific chemical targets, HNO donors have been shown to enhance apoptosis and suppress angiogenesis in breast cancer cells. However, the mechanisms for these effects are currently unresolved. To evaluate the mechanism of action involved in cell death, the effects of our NONO-aspirin prodrugs, typically near or below the $IC_{50}$ values, was studied on metabolism, ROS and reactive nitrogen species (RNS) levels, DNA damage and apoptotic markers, angiogenesis and metastasis.

Figures 9A, 9B:
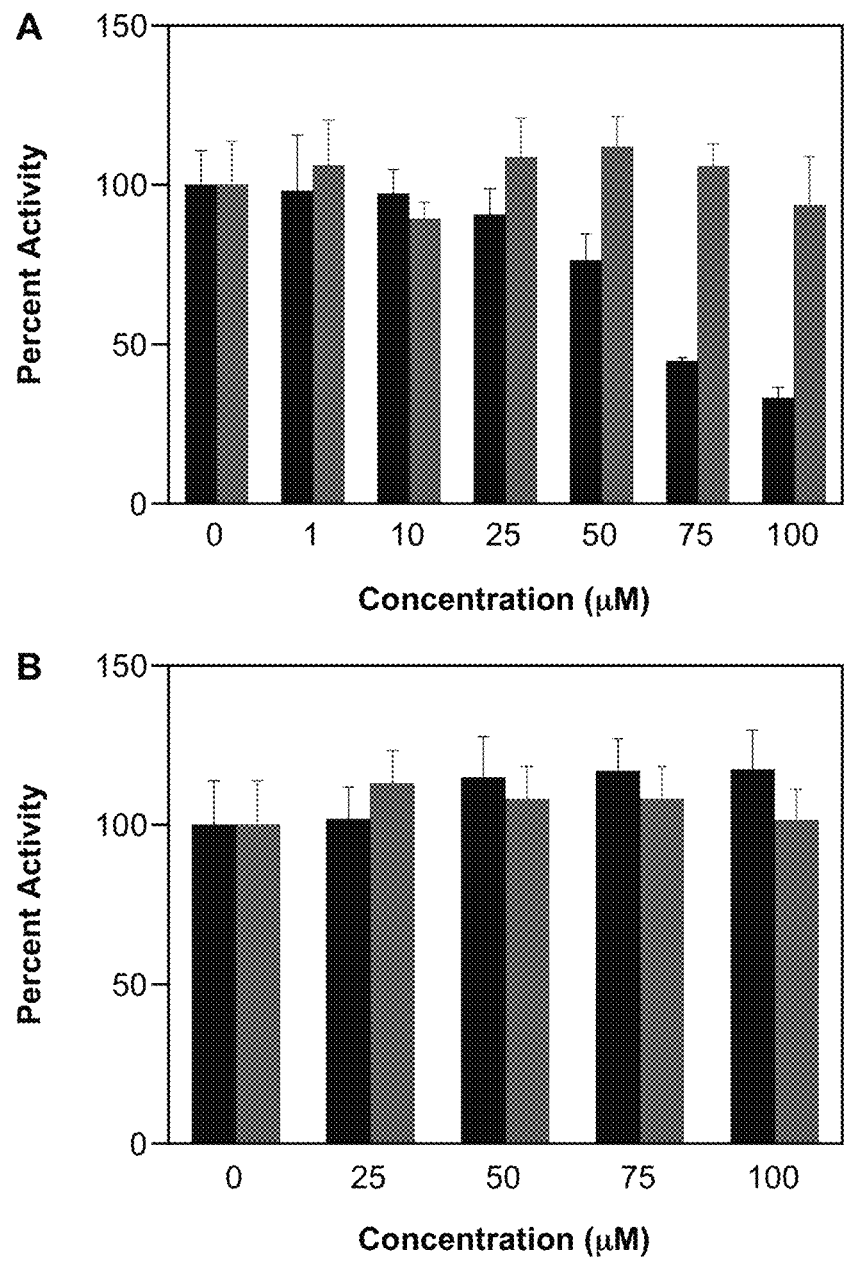
FIG. 9 shows the effect of NONO-prodrugs on inhibition of GAPDH in A) MDA-MB-231 or B) MCF-10A cells. The cells were treated with varied concentrations (0, 25, 50, 75, 100 µM) of IPA/NO-aspirin (blue) or DEA/NO-aspirin (green) for 1 h at 37° C. GAPDH activity was assessed by measuring fluorescence intensity at 570 nm. Data are plotted as mean±SD (n=3).

As shown in FIG. 9, HNO can reduce glycolysis by inhibiting GAPDH activity through direct binding to a critical thiol. The capacity to inhibit tumor proliferation in both normoxic and hypoxic regions would be a significant advantage in cancer therapy. The direct binding of HNO to thiols can also lead to disruption of PARP-dependent DNA repair pathways (FIG. 10) and activation of caspase-3 (FIG. 11), suggesting multiple O2-independent mechanisms to induction of apoptosis by IPA/NO-aspirin.

Example 13

Methods of Increasing Oxidant Levels Using Compound Embodiments

Redox active species can modify proteins, DNA and lipids through oxidative, nitrosative and nitrative mechanisms. Redox induced stress is a result of uncontrolled modification of biomolecules once natural cellular defenses, such as the antioxidant system, are overwhelmed. Accumulation of damage can lead to cell death and tissue injury. Redox active species also function as signaling molecules, through modification of individual targets that elicit specific biological responses, such as protection against or response to chemical stress. For example, high levels of NO lead to phosphorylation and stabilization of p53, suggesting a role for NO in cell cycle regulation, DNA repair and apoptosis. Redox active oxygen and nitrogen species can also interact to lead to responses unique to either reactant.

Figure 12:
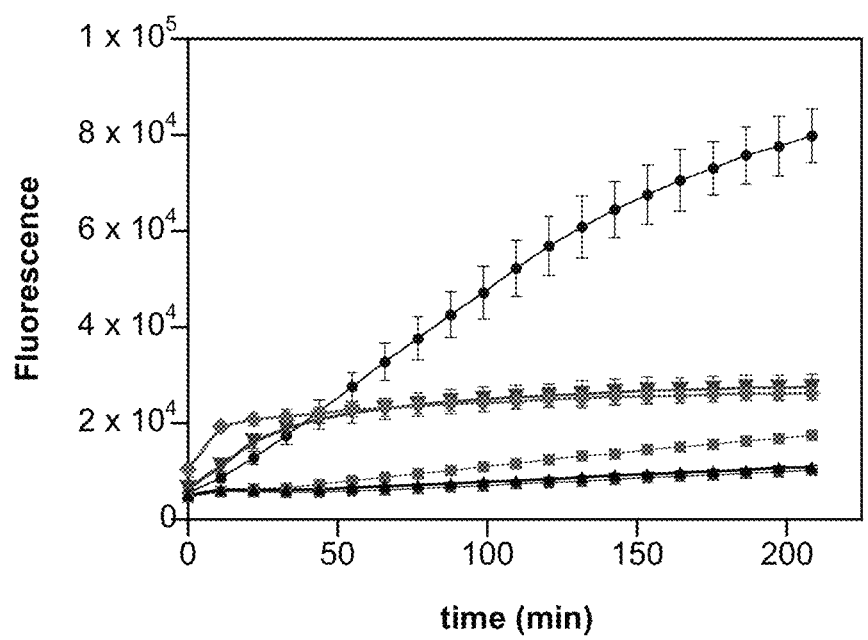
FIG. 12 shows the effect of NONO-aspirin prodrugs, aspirin or parent diazeniumdiolates (100 µM) on oxidation of DCF in MDA-MB-231 cells. DCF loaded cells were treated with IPA/NO-aspirin (blue), DEA/NO-aspirin (green), IPA/NO (magenta), DEA/NO (brown), aspirin (red) or DMSO (0.1%; black) at 37° C., and the fluorescence at 535 nm was measured in a time-dependent manner. Data are plotted as mean±SD (n=4).

Oxidation of 2',7'-dichlorofluorescein (DCF) to fluorescein is a convenient indictor of the level of oxidants in cells. In all three breast cancer lines, a significant increase in fluorescence intensity was observed upon exposure of IPA/NO-aspirin (FIG. 12; MDA-MB-231 shown as the representative example). Both IPA/NO and DEA/NO also oxidized DCF, but to a much reduced extent. In contrast, aspirin was ineffective compared to control while DEA/NO-aspirin had minimal impact.

These data demonstrate that uptake and esterase-mediated cleavage of the prodrugs are significant and that intracellular delivery was more effective at modifying cellular targets than extracellular decomposition. In A549 cells, IPA/NO-aspirin decomposition was apparently complete in approximately 3 hours while DEA-NO-aspirin was about three times longer-lived. Here, it is clear that IPA/NO-aspirin has substantial capacity to induce oxidative modifications.

Example 14

Methods of Modifying Apoptosis, Angiogenesis, and Metastasis Using Compound Embodiments Upregulation of COX-2 levels in tumor cells, leading to elevated levels of prostaglandin $E_2$ ($PGE_2$) can be an important factor in cancer progression by increasing metastasis, cell proliferation and angiogenesis and reducing immune response and apoptosis. Both NONO-aspirin prodrugs have been shown to decrease the level of $PGE_2$. In this example, the impact of the prodrugs on apoptosis, angiogenesis and metastasis was investigated.

Apoptosis is a biological process that is critical for normal development and tissue homeostasis. Mutations leading to dysfunction in apoptosis can lead to the uncontrolled cell proliferation that is inherent to cancer. Apoptosis is tightly controlled both genetically and by post-translational modifications. NO is an important regulator of apoptosis and shows a concentration-dependent effect on induction of both pro- and anti-apoptotic signaling pathways based on cell type and cellular redox status. For example, NO activates the tumor suppressor p53. Although HNO has been shown to increase apoptosis, the mechanism is not resolved. DNA damage is one of the principle triggers of programmed cell death, leading to elimination of impaired cells. Thus, accumulation of DNA damage as shown in FIG. 7 may contribute, but like NO, HNO may also activate apoptotic pathways. Here, we examined the effect of the NO-aspirin prodrugs on the apoptotic markers caspase-3 and cleaved PARP and on p53 stabilization.

Figures 11A, 11B:
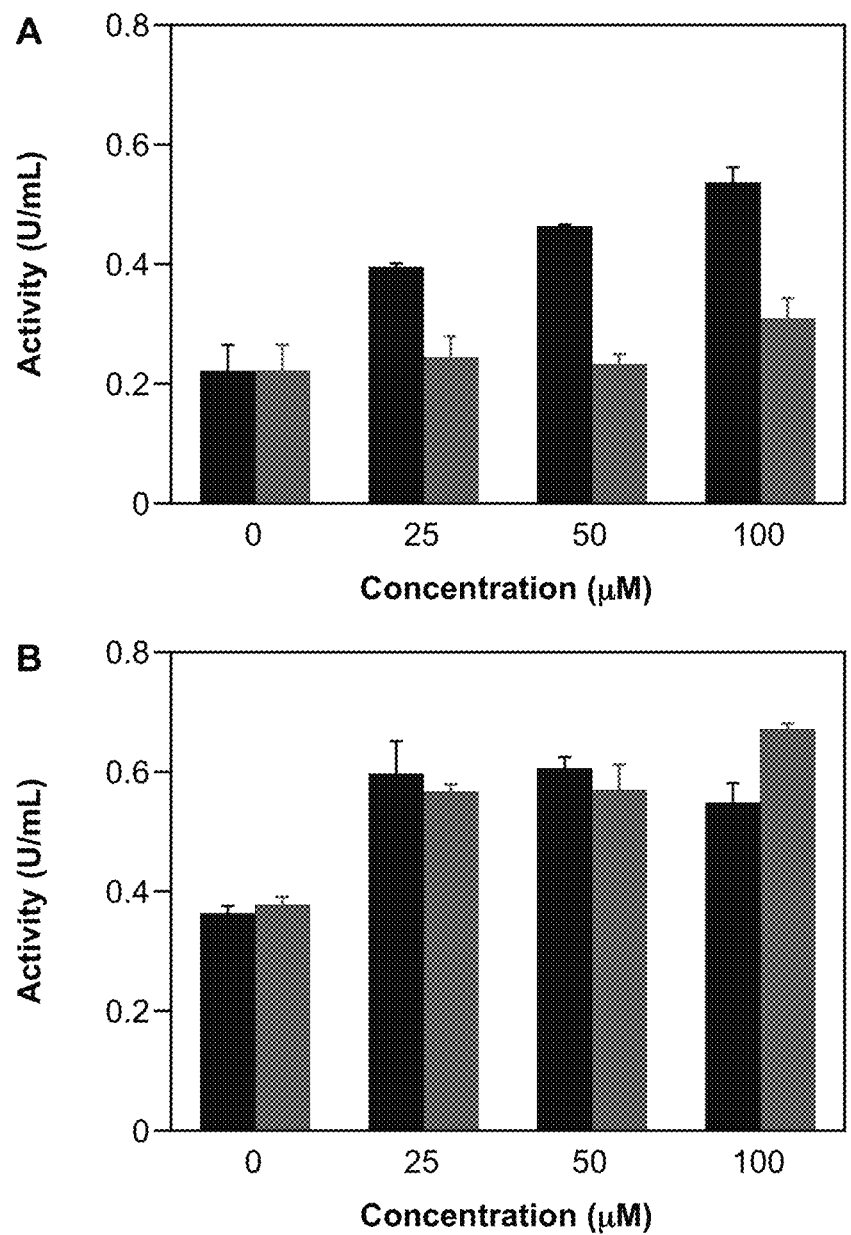
FIG. 11 shows the effect of NONO-aspirin prodrugs on caspase-3 activity of A) MDA-MB-231, B) MDA-MB-468 or C) MCF-7 cells. The cells were treated with various concentrations (0, 25, 50, 100 µM) of IPA/NO-aspirin (blue) or DEA/NO-aspirin (green) for 24 h at 37° C. Caspase-3 activity was determined by recording the fluorescence ($\lambda_{ex}$ 485 nm, $\lambda_{em}$ 535 nm) of the product formed by cleavage of the substrate, N-Ac-DEVD-N'-MC-R11. Data are plotted as mean±SD (n=3).
Figure 11C:
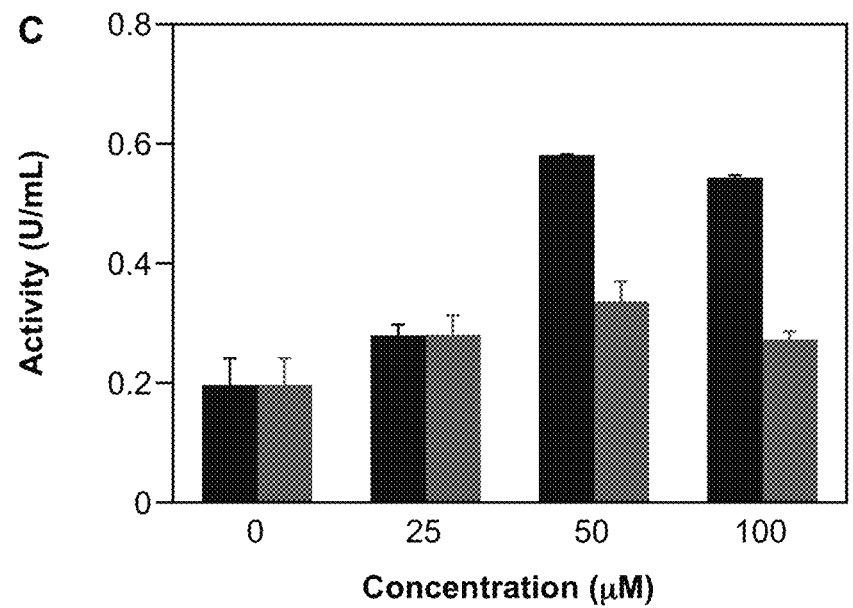

Caspases are cysteine-aspartate proteases that can trigger apoptosis through a signaling cascade. Caspase-3 is an effector protease that has active cysteine residues that are susceptible to S-nitrosation. The impact of this modification has been variously reported to lead to reversible inhibition and to activation. IPA/NO-aspirin activated caspase-3 in all three breast cancer lines, with somewhat varied sensitivity (FIG. 11). The effect of exposure to DEA/NO-aspirin was more modest in MDA-MB-231 and MCF7 cells.

As an important component of the DNA repair machinery, the PARP family of nuclear enzymes is a major target in the design of anti-cancer agents. PARP is activated by DNA strand breaks and catalyzes the transfer of ADP-ribose to nuclear proteins. When cells are undergoing apoptosis, the DNA repair mechanism is halted by cleavage of PARP, a downstream target of caspase-3. As a zinc finger protein, PARP is a target for RNS. The inhibitory effect of the HNO donor Angeli's salt and of DEA/NO on PARP activity has been determined in caspase-3 null MCF-7 cells. The inhibitory effect was rapid, but required rather high concentrations of donor.

Figure 10:
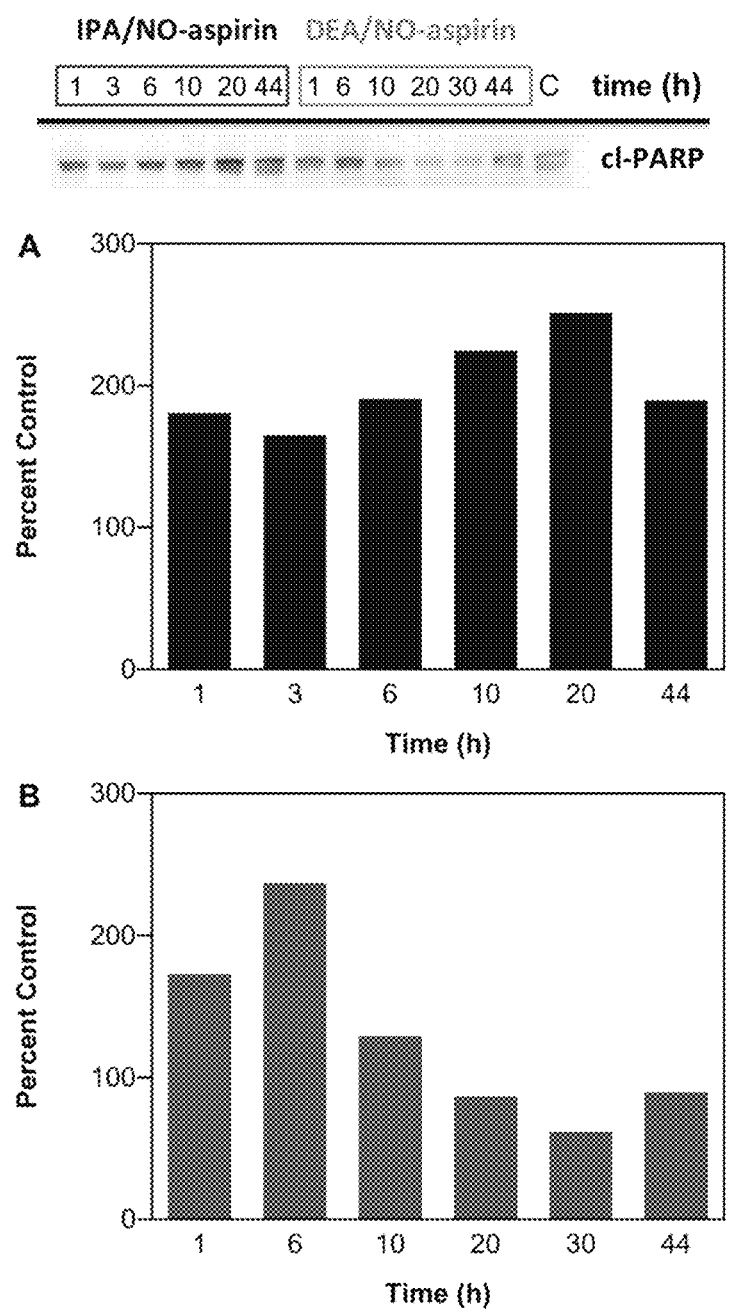
FIG. 10 shows the effect of NONO-aspirin prodrugs on PARP cleavage in MDA-MB-231 cells. The cells were treated with 50 µM IPA/NO-aspirin (blue) or 75 µM DEA/NO-aspirin (green), respectively at 37° C., and protein was collected at various time points (1-44 h). Lanes 1-6 (20 µg of protein): IPA/NO-aspirin at 1, 3, 6, 10, 20, 44 h; Lanes 6-12: DEA/NO-aspirin at 1, 6, 10, 20, 30, 44 h; Lane 15: control. Cleaved PARP levels at different time points were quantified by Western blot with respect to control, which was treated as 100%. HPRT was used as the loading control.
Figure 13:
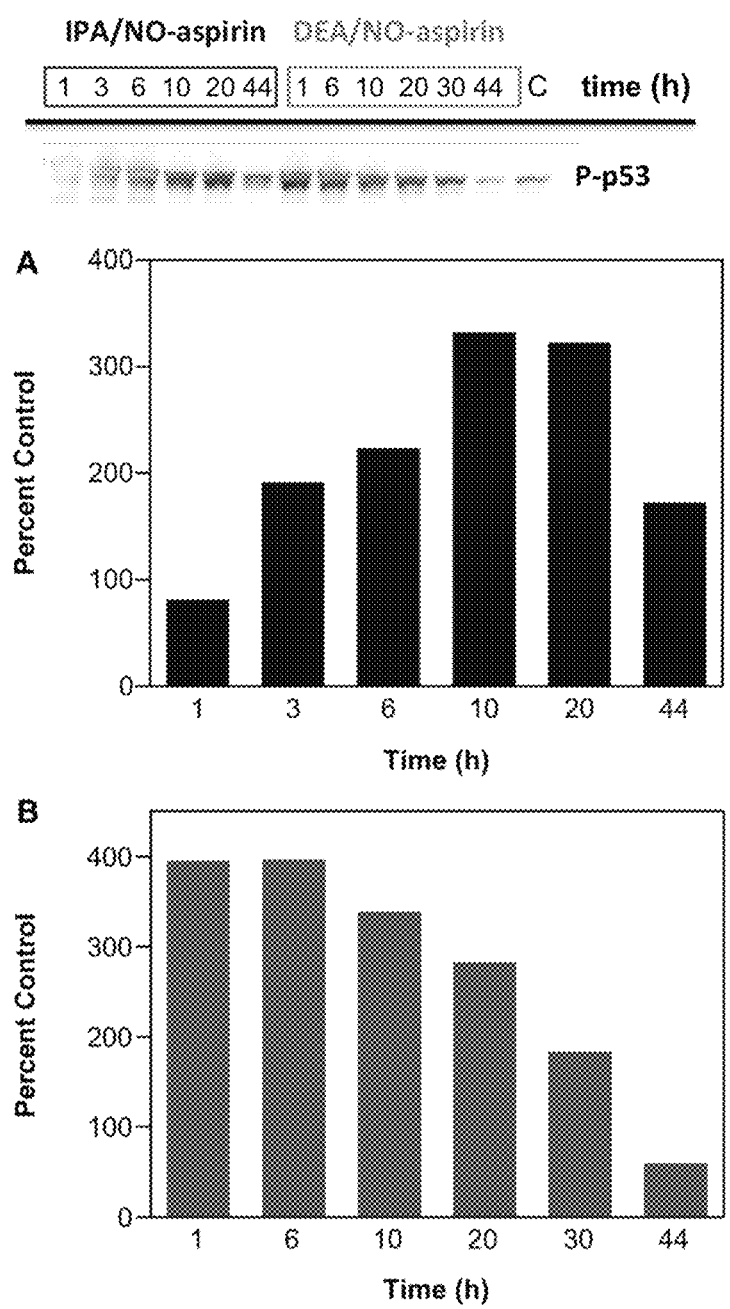
FIG. 13 shows the effect of NONO-aspirin prodrugs on p53 phosphorylation in MDA-MB-231 cells. The cells were treated with 50 µM IPA/NO-aspirin (blue) or 75 µM DEA/NO-aspirin (green), respectively at 37° C., and protein was collected at various time points (1-44 h). P-p53 was quantified by Western blot. Lanes 1-6 (20 µg of protein): IPA/NO-aspirin at 1, 3, 6, 10, 20, 44 h; Lanes 6-12: DEA/NO-aspirin at 1, 6, 10, 20, 30, 44 h; Lane 15: control. p-P53 protein at different time points was quantified by Western blot with respect to control, which was treated as 100%. HPRT was used as loading control.

Preliminary analysis in MDA-MB-231 cells indicates that IPA/NO-aspirin increases the level of cleaved PARP in a longer-term fashion while sensitivity to DEA/NO-aspirin was relatively short-lived (FIG. 10). A similar time sensitivity was observed for phosphorylation of p53 (FIG. 13). Since a number of chemotherapies and radiation therapy are based on inducing DNA damage in cancer cells, inhibition of PARP by HNO donors may increase the efficacy of these treatments. Furthermore, IPA/NO-aspirin is able to not only induce DNA damage but also to impede DNA repair.

Figure 18:
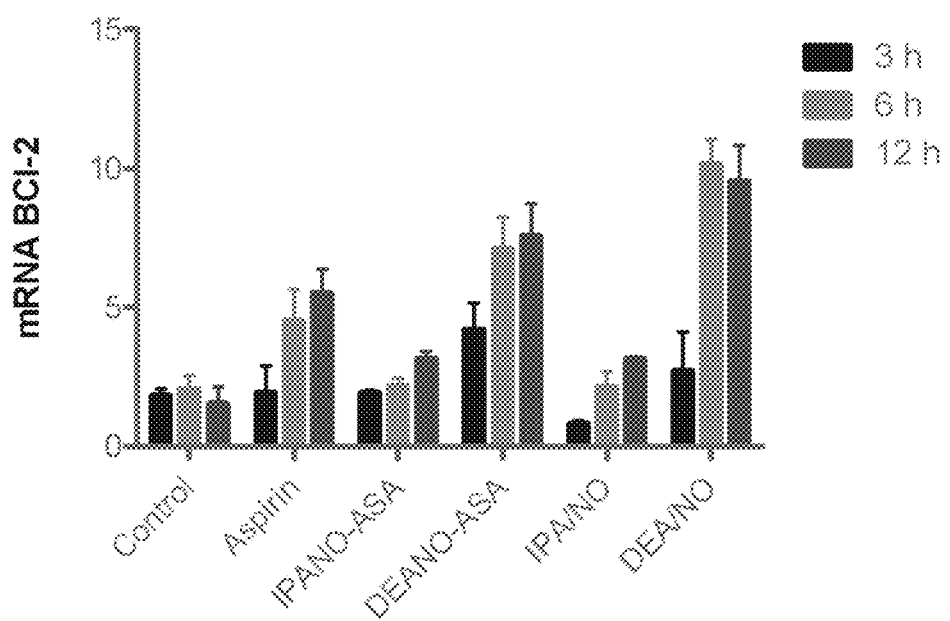
FIG. 18 shows the effect of various embodiments on the induction of BCL-2 expression, thus inhibiting apoptosis.

In addition, both NO and aspirin induce BCL-2 expression and, thus, inhibits apoptosis. Furthermore, HNO does not affect BCL-2 levels, but IPA/NO-aspirin inhibits the aspirin effect (FIG. 18).

Angiogenesis promotes tumor progression by initiating recruitment of blood vessels to supply nutrients and oxygen to growing cancer cells. Angiogenesis also plays an important role in development of metastatic tumors at secondary sites. NO impacts tumor growth in a concentration-dependent manner with low levels promoting cell survival, migration, proliferation and angiogenesis and higher fluxes causing vascular cell growth arrest and cell death. A high concentration of the HNO donor Angeli's salt inhibited angiogenesis in mouse tumor specimens, decreased serum vascular endothelial growth factor (VEGF) levels and inhibited hypoxia-inducible factor (HIF) 1α in human breast cancer cells.

Figure 14:
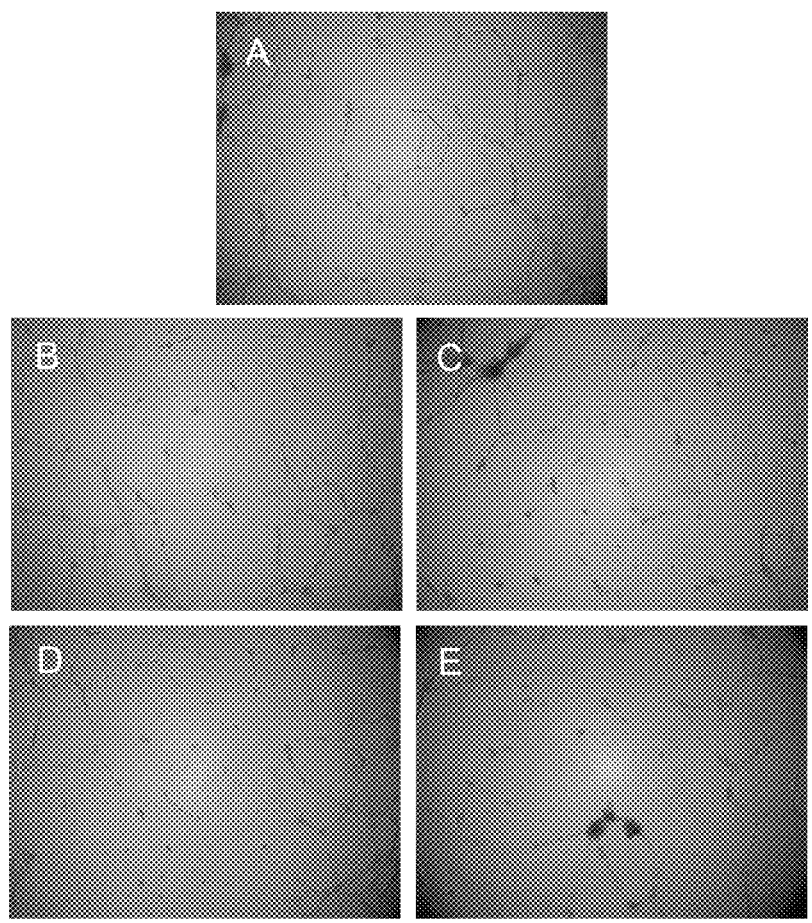
FIG. 14 shows the effect of NONO-aspirin prodrugs on inhibition of angiogenesis in HUVECs. Cells in Matrigel were treated with A) DMSO, B) 1 µM or C) 10 µM IPA/NO-aspirin, D) 1 µM or E) 10 µM DEA/NO-aspirin at 37° C., and the extent of tube formation was measured after 12 h using a microscope.
Figure 15:
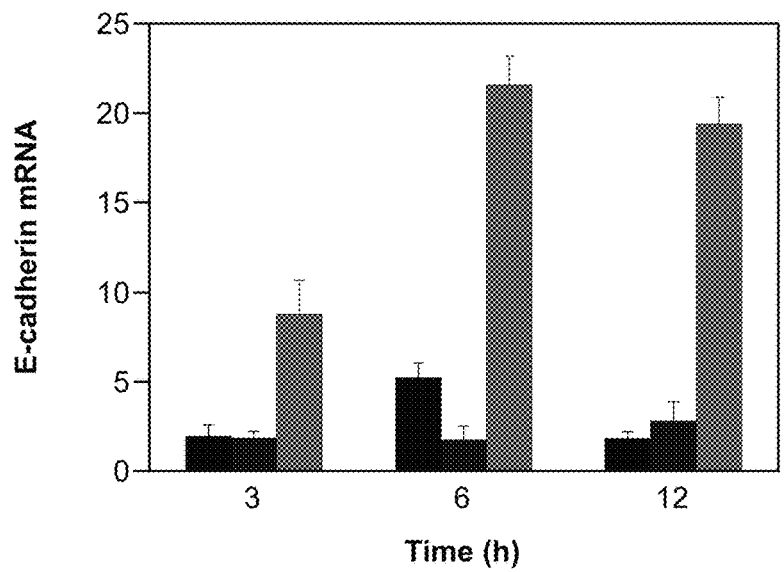
FIG. 15 shows the effect of NONO-aspirin prodrugs on E-cadherin expression in MDA-MB-231 cells. The cells were treated with vehicle (black) or 100 µM IPA/NO-aspirin (blue) or DEA/NO-aspirin (green) for 3, 6 or 12 h at 37° C. Relative mRNA expression was measured using RT-PCR techniques. E-cadherin mRNA were quantified with respect to control (1).
Figure 16:
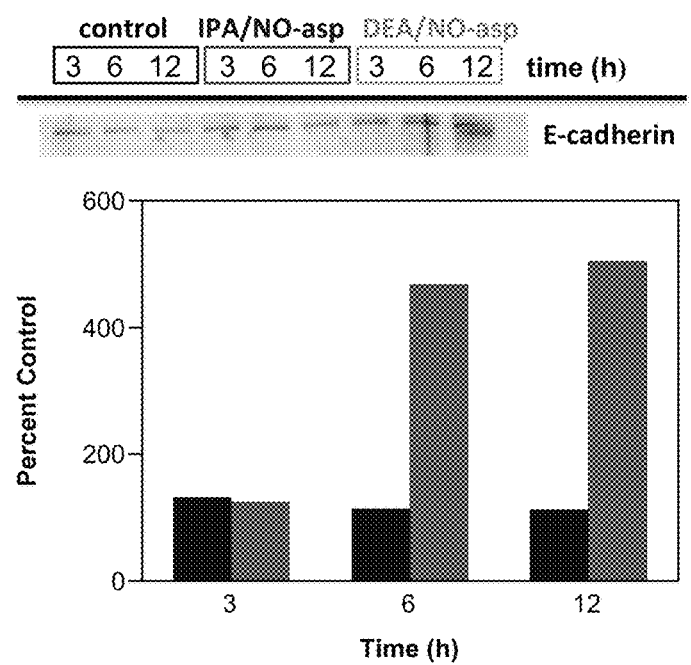
FIG. 16 shows the effect of NONO-aspirin prodrugs on E-cadherin expression in MDA-MB-231 cells. The cells were treated with vehicle (black) or 100 µM IPA/NO-aspirin (blue) or DEA/NO-aspirin (green) for 3, 6 or 12 h at 37° C. Protein expression was measured using Western blot techniques. E-cadherin protein levels were quantified with respect to control (100%).
Figure 19:
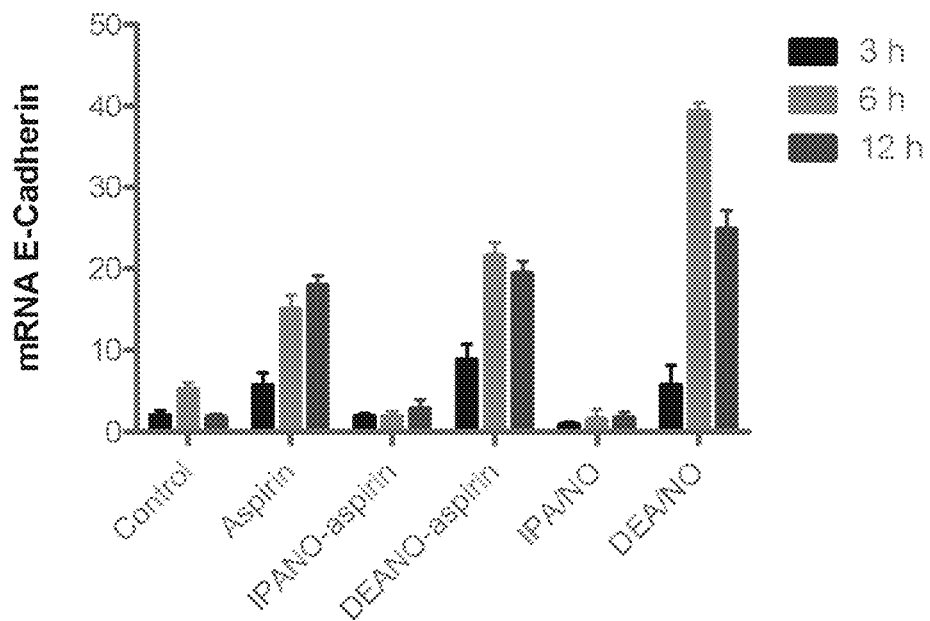
FIG. 19 shows the effect of various embodiments on the induction of E-cadherin, leading to reduced metastasis.

The impact of the NONO-aspirin prodrugs on tube formation in HUVECs after 12 hours treatment was examined as a measure of angiogenesis. Both IPA/NO-aspirin and DEA/NO-aspirin reduced angiogenesis as compared to control even at 1 (FIG. 14). We previously determined that neither IPA/NO-aspirin or DEA/NO-aspirin are appreciably cytotoxic toward HUVECs Epithelial cadherin (E-cadherin) is calcium-dependent, membrane-associated cellular adhesion glycoprotein. Loss of E-cadherin-mediated cellular adhesion is a prerequisite for invasion and metastasis of tumor cells. NO is an endogenous mediator of endothelial cell migration. NO also has been shown to promote the growth, invasion and metastasis of murine mammary tumors. However, the effect of HNO on metastasis has not been studied. IPA/NO-aspirin does not show any significant change in E-cadherin levels, suggesting that the reduced metastasis apparent in FIG. 6 is a result of either activation of a different pathway or an effect at the primary tumor. In contrast, DEA/NO-aspirin did increase E-cadherin expression in a time-dependent manner at both the mRNA (FIG. 15 and FIG. 19) and protein levels (FIG. 16). This can result in a reversal of tumor cells from an invasive, mesenchymal, to a benign, epithelial phenotype.

The observed reduction in $PGE_2$ levels by IPA/NO-aspirin may be in part responsible for the observed antiangiogenic (FIG. 14) and antimetastatic effects (FIG. 6). Accordingly, IPA/NO-aspirin offers a single compound route to multifaceted targeting of cancer progression and recurrence mechanisms while maintaining a high safety profile.

The NO donor DEA/NO-aspirin lacks the DNA damaging effect of IPA/NO-aspirin and cannot directly lead to modification of thiols. In fact much of the antiproliferative effects of NO are $O_2$-dependent through formation of nitrosative intermediates. However, DEA/NO-aspirin also was selectivity cytotoxic toward cancer cells, and showed a decrease in angiogenesis (FIG. 14) and inhibition of metastasis (FIG. 6 and FIG. 15). It is not clear at this time if any of the effects of DEA/NO-aspirin are cGMP-dependent, but intracellular delivery will increase specificity. Since some cancer cells can produce NO via NOS, the impacts of intracellular production of NO by DEA/NO-aspirin require further investigation Example 15

Methods of Modifying Cell Phenotype Using Compound Embodiments

Figure 20:
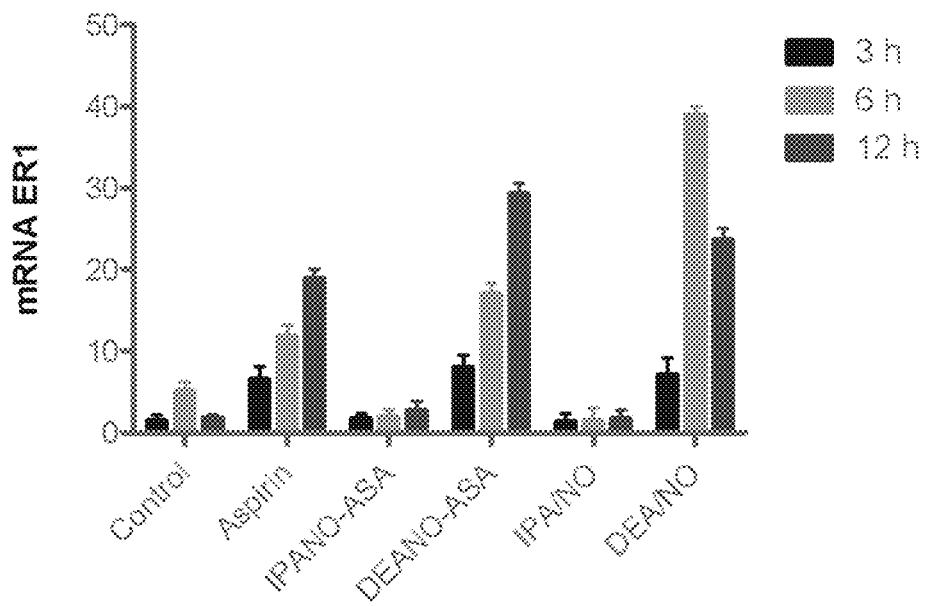
FIG. 20 shows the effect of various embodiments on the mRNA of ER1, demonstrating that ER-α levels can be increased in ER-α(−) cells, resulting in a change to a less aggressive genotype.

Both NO and aspirin increases ERα levels in ER-α(−) cells, thus modifying the phenotype of the cells to a less aggressive genotype. As shown in FIG. 20, HNO does not appear to affect ER-α levels, but IPA/NO-aspirin is shown to inhibit the aspirin effect.

Example 16

Methods of Decreasing Glycolysis Using Compound Embodiments

GAPDH is a critical glycolytic enzyme that can play an important role in cancer therapy as solid tumors often utilize glycolytic pathways even during normoxia to meet their energy requirements. Thus, inhibition of GAPDH can diminish ATP availability for tumor cells. GAPDH is also involved in initiation of apoptosis and in DNA repair. IPA/NO-aspirin inhibited GAPDH activity in a concentration (FIG. 9A) and time-dependent-manner in MDA-MB-231 cells through direct binding to a critical thiol. In contrast, IPA/NO-aspirin did not affect GAPDH activity in MCF-10A cells (FIG. 9B), indicating that this protein may play a role in the selective cytotoxicity of IPA/NO-aspirin toward carcinogenic cell lines. At up to 100 DEA/NO-aspirin was not inhibitory in either cell line.

Example 17

Methods of Treating Cancer with Combination Therapies Using Compound Embodiments In this example, a 3-(4,5-dimethylthiazol-2-yl)-2,5-diphenyltetrazolium bromide (MTT)viability assay was used to evaluate combination therapy to on the cytotoxicity of cancer cells using compound embodiments. Furthermore, in this example, AcOM-CPA/NO was used as the exemplary compound. AcOM-CPA/NO has the following structure:

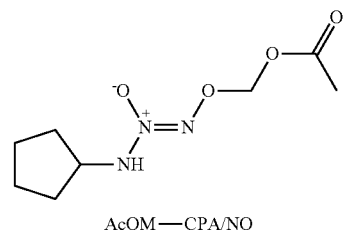

AcOM—CPA/NO

Cells were plated at 8,000-10,000 cells per well in a 96-well plate and grown overnight. Cells were treated with different concentrations (10-100 μM) of AcOM-CPA/NO or control (ethanol, <0.1% by volume) for 48 hours. Thereafter, 10 μL of 5 mg/mL MTT was added to each well, and the plate was incubated for 1 hour at 37° C. After removal of the media, 100 μL of DMSO was added to each well, and the absorbance was recorded at 550 nm. Growth inhibition is reported as the percentage of the corresponding control. Figures are representative data sets, each from n≥3 individual experiments. For analysis of combined effects of AcOM-CPA/NO with tamoxifen, cells were treated with 10 μM tamoxifen, 75 μM of AcOM-CPA/NO, or a combination for 48 hours.

NO releasing donor compounds may increase the cytotoxicity of cancer drugs such as cisplatin, melphalan, and doxorubicin toward cancer cells. Such analysis has not been reported for HNO donors. Thus, the potential of using AcOM-CPA/NO in combination with tamoxifen for targeting ER-breast cancer was evaluated.

Tamoxifen is used clinically worldwide in treatment of early and advanced stages of ER+ breast cancer and is also prescribed as a chemopreventive agent for women who are at high risk of developing breast cancer. Tamoxifen exerts its anticancer properties by competing with estrogen for binding to the estrogen receptor, which is crucial for breast cancer cell proliferation. Successful application of tamoxifen to a broader population of breast cancer patients requires development of effective therapeutic approaches in targeting more aggressive hormone-insensitive breast cancer patients.

Figure 17:
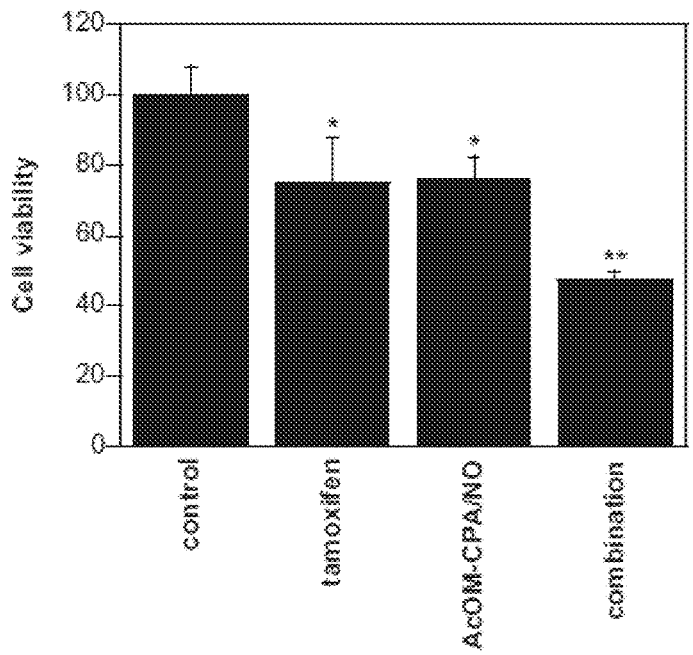
FIG. 17 shows the effects of tamoxifen (10 µM), AcOM-CPA/NO (75 µM), or a combination thereof on the viability of MDA-MB-231 cells (mean+/−SD, n≥3; *, p<0.05 vs. control, **, p<0.01 vs. control).

MB-231 cells were used for evaluating the combinatory potential of AcOM-CPA/NO with tamoxifen. FIG. 17 shows the surviving fractions of MB-231 cells treated with tamoxifen (10 μM) or AcOM-CPA/NO (75 μM) with 76+/−13 and 75+/−6% viability, respectively. Co-administration of tamoxifen and AcOM-CPA/NO reduced cell viability to 47+/−3%. Since tamoxifen and HNO will likely have different molecular targets, this method will provide multiple pathways to impact cell survival in combination. Moreover, long term, combined usage may lower occurrence of resistance compared to individual treatment.

What is claimed is:

1. A method of treating breast cancer, said method comprising the step of administering a combination of a therapeutically effective amount of:
   (i) a tumor-targeted drug and
   (ii) a therapeutic agent selected from the group consisting of a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, everolimus, ispinesib, budesonide, dasatinib, an epothilone, a maytansine, and tamoxifen,
to a subject in need of such a treatment, wherein said tumor-targeted drug is a compound of the formula (I) or a pharmaceutically acceptable salt thereof:

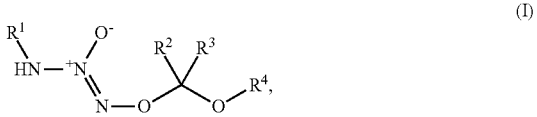

wherein:
- $R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;
- $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and
- $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

wherein the compound of the formula (I) or pharmaceutically acceptable salt and the therapeutic agent are effective in treating cancer in the mammal.

2. The method of claim 1, wherein the therapeutic agent is tamoxifen.

3. The method of claim 1, wherein the breast cancer is an estrogen receptor negative (ER(−)) breast cancer.

4. The method of claim 1, wherein $R^1$ is optionally substituted $C_{1-12}$ alkyl, optionally substituted $C_{3-12}$ alkenyl, or optionally substituted $C_{3-8}$ cycloalkyl.

5. The method of claim 1, wherein $R^2$ and $R^3$ are the same or different and each is hydrogen, $C_{1-12}$ alkyl, aryl, or heteroaryl, each of which, other than hydrogen, is optionally substituted.

6. The method of claim 1, wherein $R^2$ and $R^3$ are hydrogen.

7. The method of claim 1, wherein $R^1$ is isopropyl.

8. The method of claim 1, wherein $R^4$ is —C(=O)$R^5$, wherein $R^5$ is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino.

9. The method of claim 1, wherein $R^5$ is an optionally substituted $C_{1-12}$ alkyl.

10. The method of claim 1, wherein the compound of formula (I) is

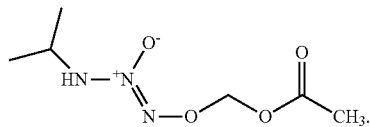

11. The method of claim 1, wherein the tumor-targeted drug is selected from the group consisting of:

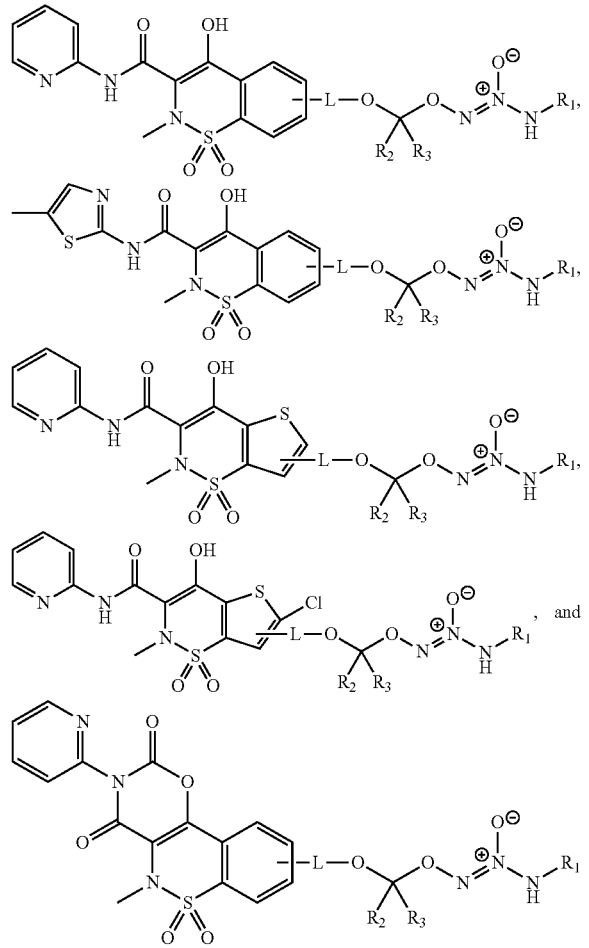

wherein:
- L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;
- $R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt thereof.

12. The method of claim 1, wherein the tumor-targeted drug is selected from the group consisting of:

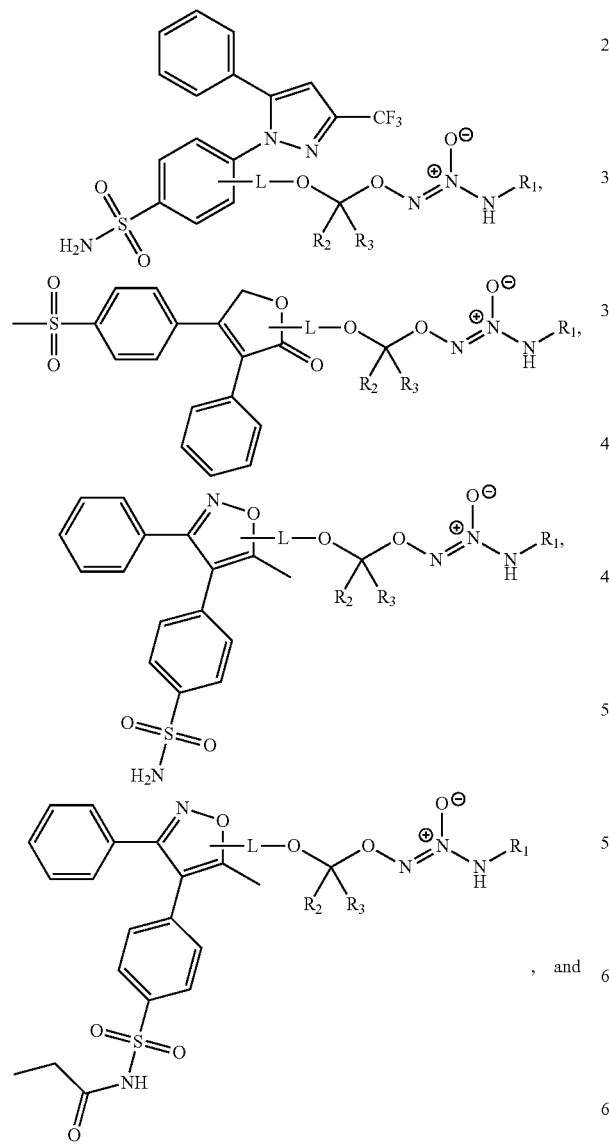

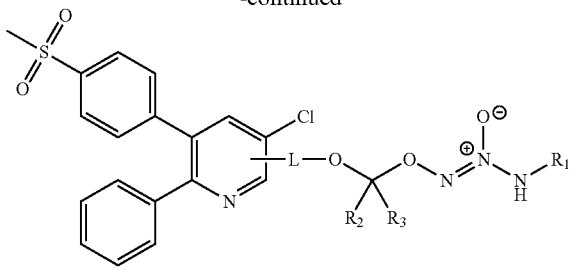

wherein:

L is a linking group selected from the group consisting of alkyl, alkenyl, alkynyl, cycloalkyl, cycloalkylalkyl, aryl, arylalkyl, carbonyl, thiocarbonyl, iminocarbonyl, carboxyl, and carbamoyl;

$R^1$ is selected from $C_{1-12}$ alkyl, $C_{3-12}$ alkenyl, $C_{3-12}$ alkynyl, $C_{3-8}$ cycloalkyl, and heterocyclyl, each of which is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino; and $R^2$ and $R^3$ are the same or different and each is selected from hydrogen, $C_{1-12}$ alkyl, $C_{2-12}$ alkenyl, $C_{2-12}$ alkynyl, $C_{3-8}$ cycloalkyl, heterocyclyl, aryl, and heteroaryl, each of which, other than hydrogen, is optionally substituted with one or more moieties selected from the group consisting of halo, OH, CN, hydroxy-$C_{1-12}$ alkyl, halo-$C_{1-12}$ alkyl, amino-$C_{1-12}$ alkyl, $C_{1-12}$ alkoxy, aryloxy, $C_{1-12}$ thioalkoxy, nitro, sulfonato, $C_{1-12}$ acyl, $C_{2-12}$ acyloxy, carboxyl, mercapto, $C_{1-12}$ alkoxy-carbonyl, $C_{1-12}$ alkoxy-carbonyloxy, amido, amino, $C_{1-12}$ alkylamino, and di-$C_{1-12}$ alkyl-amino;

or a pharmaceutically acceptable salt thereof.

13. The method of claim 1, wherein the tumor-targeted drug is selected from the group consisting of:

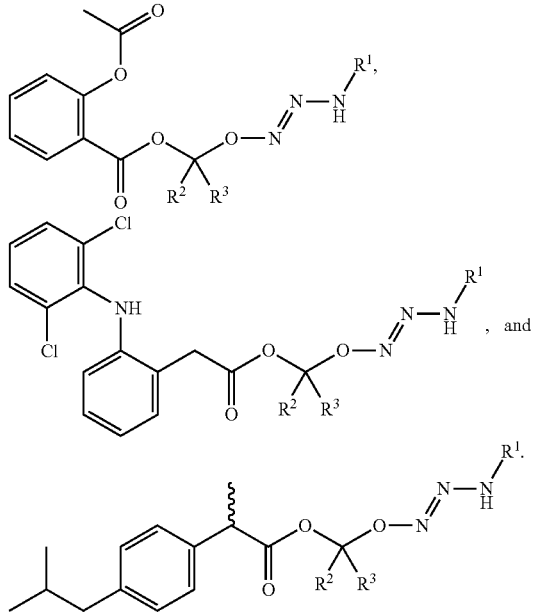

14. The method of claim 1, wherein the tumor-targeted drug is of the formula:
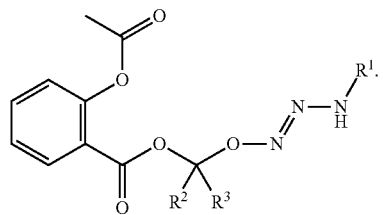
or a salt thereof.